(12) United States Patent
Deprez et al.

(10) Patent No.: US 8,338,599 B2
(45) Date of Patent: Dec. 25, 2012

(54) COMPOUNDS HAVING A POTENTIATING EFFECT ON THE ACTIVITY OF ETHIONAMIDE AND USES THEREOF

(75) Inventors: Benoît Deprez, Lille (FR); Nicolas Willand, Lille (FR); Bertrand Dirie, Marcq-en-Baroeul (FR); Patrick Toto, Lille (FR); Vincent Villeret, Wannebecq (BE); Camille Locht, Brussels (BE); Alain Baulard, Templeuve (BE)

(73) Assignees: Institut Pasteur de Lille, Lille (FR); Centre National de la Recherche Scientifique, Paris (FR); Universite de Lille 2, Universite du Droit et de la Sante, Lille (FR); Institut National de la Sante et de la Recherche Medicale (Inserm), Paris (FR)

( * ) Notice: Subject to any disclaimer, the term of this patent is extended or adjusted under 35 U.S.C. 154(b) by 727 days.

(21) Appl. No.: 12/306,333

(22) PCT Filed: Jul. 4, 2007

(86) PCT No.: PCT/FR2007/001138
§ 371 (c)(1),
(2), (4) Date: Aug. 14, 2009

(87) PCT Pub. No.: WO2008/003861
PCT Pub. Date: Jan. 10, 2008

(65) Prior Publication Data
US 2011/0136823 A1    Jun. 9, 2011

(30) Foreign Application Priority Data
Jul. 4, 2006    (FR) .................................... 06 06088

(51) Int. Cl.
*A61K 31/454*    (2006.01)
*A61K 31/496*    (2006.01)
*A61P 31/04*    (2006.01)
*A61P 31/08*    (2006.01)

(52) U.S. Cl. .................. 544/367; 514/254.03; 514/326; 546/209; 546/210

(58) Field of Classification Search ................. 544/367; 514/254.03, 326; 546/209, 210
See application file for complete search history.

(56) References Cited

FOREIGN PATENT DOCUMENTS

| EP | 1 604 989 A1 | 12/2005 |
|---|---|---|
| FR | 2 275 458 A1 | 1/1976 |
| WO | WO 00/20414 A1 | 4/2000 |
| WO | WO 03/093297 A | 11/2003 |
| WO | WO 2005/061489 A1 | 7/2005 |

(Continued)

OTHER PUBLICATIONS

International Search Report and Written Opinion from International Application PCT/FR2007/001138, filed Jul. 4, 2007.

(Continued)

*Primary Examiner* — Savitha Rao
(74) *Attorney, Agent, or Firm* — Alston & Bird LLP

(57) ABSTRACT

The present invention relates to the use of compounds with a potentiating effect on the activity of antibiotics that are activatable via the EthA enzymatic pathway, for the preparation of a medicament for preventing and/or treating mycobacterial infections such as tuberculosis and leprosy, to pharmaceutical compositions comprising them in combination with an antibiotic that is activatable via the EthA pathway, to compounds having a potentiating effect on the activity of antibiotics that are activatable via the EthA enzymatic pathway, to pharmaceutical compositions comprising them and to their use as medicaments, especially medicaments for preventing and/or treating mycobacterial infections such as tuberculosis and leprosy.

9 Claims, 2 Drawing Sheets

A

B

C

FOREIGN PATENT DOCUMENTS

| | | |
|---|---|---|
| WO | WO 2006/036395 A2 | 4/2006 |
| WO | WO 2006/060424 A2 | 6/2006 |
| WO | WO 2006/065601 A2 | 6/2006 |
| WO | WO 2006/067532 A1 | 6/2006 |

OTHER PUBLICATIONS

Database CA [Online]; Chemical Abstracts Service, Columbus, Ohio, US; Matsumoto, Takahiro et al.: "Preparation of piperidinecarboxamides and piperazinecarboxamides as fatty acid amide hydrolase (FAAH) inhibitors"; XP002427080, 2006.

Databse CA [Online] Chemical Abstracts Service, Columbus, Ohio, US; Bessis, Anne-Sophie et al: "Preparation of piperdine derivatives as modulators of metabotropic glutamate receptors (mGluR5)"; XP002427081.

Poulain, R. F. et al: "Parallel synthesis of 1,2,4-oxadiazoles from carboxylic acids using an improved, uronium-based, activation"; Tetrahedron Letters, 42(8), 1495-1498 CODEN: TELEAY; ISSN: 004-4039, 2001, XP002427070, 2005.

Raimundo, Brian C. et al: "Integrating Fragment Assembly and Biophysical Methods in the Chemical Advancement of Small-Molecule Antagonists of IL-2: An Approach for Inhibiting Protein-Protein Interactions"; Journal of Medicinal Chemistry, 47(12), 3111-3130 CODEN: JMCMAR; ISSN: 0022-2623, 2004, XP002348124.

Database CA [Online] Chemical Abstracts Service, Columbus, Ohio, US; Williams, John P. et al: "A solution-phase combinatorial synthesis of selective dopamine D4 ligands", XP002427082, 2001.

SEQUENCE LISTING

<160> NUMBER OF SEQ ID NOS: 4

<210> SEQ ID NO 1
<211> LENGTH: 24
<212> TYPE: DNA
<213> ORGANISM: Artificial
<220> FEATURE:
<223> OTHER INFORMATION: Amorce PCR O-270

<400> SEQUENCE: 1
cggtcatgga tccacgctat caac                24

<210> SEQ ID NO 2

```
<211> LENGTH: 21
<212> TYPE: DNA
<213> ORGANISM: Artificial
<220> FEATURE:
<223> OTHER INFORMATION: Amorce PCR O-271

<400> SEQUENCE: 2
ctgactggcc gcggaggtgg t                                              21

<210> SEQ ID NO 3
<211> LENGTH: 21
<212> TYPE: DNA
<213> ORGANISM: Artificial
<220> FEATURE:
<223> OTHER INFORMATION: Amorce PCR O-343

<400> SEQUENCE: 3
tttccgtgtc gcccttattc c                                              21

<210> SEQ ID NO 4
<211> LENGTH: 21
<212> TYPE: DNA
<213> ORGANISM: Artificial
<220> FEATURE:
<223> OTHER INFORMATION: Amorce PCR O-344

<400> SEQUENCE: 4
ccactcgtgc acccaactga t                                              21
```

COMPOUNDS HAVING A POTENTIATING EFFECT ON THE ACTIVITY OF ETHIONAMIDE AND USES THEREOF

CROSS REFERENCE TO RELATED APPLICATIONS

This application is a national stage application filed under 35 U.S.C. 371 of International Application No. PCT/FR2007/001138, filed Jul. 4, 2007, which claims priority from French Application No. 06/06088, filed Jul. 4, 2006.

FIELD AND BACKGROUND OF THE INVENTION

The present invention relates to the use of compounds with a potentiating effect on the activity of antibiotics that are activatable via the EthA enzymatic pathway, for the preparation of a medicament for preventing and/or treating mycobacterial infections such as tuberculosis and leprosy, to pharmaceutical compositions comprising them in combination with an antibiotic that is activatable via the EthA pathway, to compounds having a potentiating effect on the activity of antibiotics that are activatable via the EthA enzymatic pathway, to pharmaceutical compositions comprising them and to their use as medicaments, especially medicaments for preventing and/or treating mycobacterial infections such as tuberculosis and leprosy.

Tuberculosis kills two million people per year worldwide. The AIDS epidemic and the emergence of antibiotic multiresistant strains have contributed toward worsening the impact of this disease, which is considered by the World Health Organization as being responsible for an increasingly dangerous worldwide epidemic, and as being a worldwide health emergency. The WHO estimates that, between 2000 and 2020, close to one billion people will be infected with the tuberculosis *bacillus* and about 200 million of them will develop the disease, which may lead to the death of 35 million people if no improvements are made in controlling or treating this infection.

An increasing number of *Mycobacterium tuberculosis* strains are characterized at the present time by multidrug resistance to the first-line antibiotics isoniazid (INH) and rifampicin (RIF). These antibiotics have a high therapeutic index (the therapeutic index of an active principle is the ratio of the therapeutic dose to the toxic dose) and should thus be replaced with second-line antibiotics to which the strains are not resistant, but which have the drawback of having a lower therapeutic index.

Among these second-line antibiotics, ethionamide(2-ethyl thioisonicotinamide: ETH, Trescatyl; CAS number 536-33-4) has been commonly used clinically for more than 35 years mainly in the treatment of pulmonary and extrapulmonary tuberculoses (*Mycobacterium tuberculosis*), and secondarily for treating infections with atypical mycobacteria (*Mycobacterium kansasii*) and leprosy (*Mycobacterium leprae*). ETH is a prodrug that needs to be activated in order for its antibacterial activity to be able to be exerted. The activation of ethionamide is performed by a specific mycobacterial enzyme, the enzyme EthA, which is a flavin monooxygenase of Baeyer-Villiger type. In its normal physiological state, the mycobacterium synthesizes little EthA enzyme, which limits the activation of the prodrug and is reflected by low sensitivity of the bacterium toward this antibiotic. Recently, the mechanism of expression of the gene encoding EthA was elucidated by Baulard et al. (Baulard A. et al., J. Biol. Chem., 2000, 275(36) 28326-28331) and Engohang-Ndong et al. (Engohang-Ndong et al., Mol. Microbiology, 2004, 51(1), 175-188). Expression of the ethA gene is placed under the control of an adjacent gene: the ethR gene. The ethR gene encodes a protein, EthR, which binds to a target DNA sequence upstream of the ethA gene sequence. On binding to the ethA gene promoter, the EthR protein acts as a transcription repressor for this gene. By genetically inactivating the ethR gene, hypersensitivity of the mycobacterium to ethionamide is observed (Baulard et al., 2000, cited previously; Engohang-Ndong et al., 2004, cited previously), due to the non-repression of ethA transcription.

ETH is an antibiotic that is known to greatly inhibit the biosynthesis of mycolic acids, which are essential constituents of the mycobacterial wall. Its presumed target is the enzyme enoyl-AcpM reductase (InhA). Its administration in therapeutically effective doses, generally 10 mg/kg/day (Johnson et al., J. Pharm. Pharmacol., 1967, 19, 1-9) leads, however, to adverse side effects such as liver toxicity, mental impairment (psychoses, anxiety, depression), intestinal disorders, and ocular and auditive impairment (Reynolds J E F et al., 1989, Martindale, the extra pharmacopoeia, $29^{th}$ ed. London, The Pharmaceutical Press, 562-563). Its use is, however, common in developing countries for the treatment of patients who relapse as a result of infection with strains of *M. tuberculosis* that are resistant to first-line antibiotics, or for treating patients suffering from lepromatous leprosy, as a replacement for clofazimine.

There is therefore a certain advantage in developing a technical solution for reducing the dose of ETH, and thereby its adverse side effects, while at the same time maintaining or improving its therapeutic efficacy.

With this aim, it has already been envisioned to potentiate the activity of ETH by combining it with a particular compound. Thus, international patent application WO 2005/047 538 describes a process for identifying EthR repressor inhibitors, and also chemical compounds having this effect. Said patent application cites, various compounds in this respect, among which is especially hexadecyl octanoate. The activity of this compound was also studied in the article by Frénois F. et al., Molecular Cell, 2004, 16, 301-307. However, given the length of its carbon chain, hexadecyl octanoate is a compound having very low bioavailability. Moreover, it is not active on live mycobacteria.

In addition, the pathway for activation of the prodrugs by EthA has also been recently illustrated for thiacetazone (Qian L, et al., Chem. Res. Toxicol. 2006, 19, 443-449), and indirectly for isoxyl (DeBarber A E, et al., Proc. Natl. Acad. Sci. USA, 2000, 97, 9677-82). Any compound capable of interfering with the EthA activation pathway should thus allow the action of these prodrugs to be potentiated.

The Inventors thus set themselves the aim of providing compounds that are easier to formulate than hexadecyl octanoate and that can be used in combination with ETH in order to potentiate its activity. This type of medicament might contain, in addition to the compounds forming the subject of the present invention, smaller doses of ETH, while at the same time maintaining efficacy that is at least equivalent to that of a medicament containing only ETH.

SUMMARY OF THE INVENTION

This objective is achieved by the compounds of formula (I) that will be described hereinbelow, and that may be used for preventing and/or treating bacterial and preferably mycobacterial infections.

A first subject of the present invention is thus the use of at least one compound of formula (I) below:

$$A\text{-}L\text{-}B \quad (I)$$

in which:
the unit A is connected to L via at least one covalent bond and is chosen from the groups of formula (II) below:

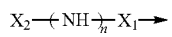
(II)

in which:
the arrow indicates the point of attachment of the covalent bond connecting $X_1$ to L, said bond involving at least one carbon atom of the group $X_1$ and a carbon, nitrogen or oxygen atom of the group L, n is an integer equal to 0 or 1, when n=1, $X_1$ represents a group chosen from $C_2$-$C_5$ alkyl chains; it being understood that a carbon atom of the group $X_1$ is engaged in the covalent bond connecting $X_1$ to —NH—, when n=0, $X_1$ represents a cyclic mononitrogen or dinitrogen group chosen from piperidine, piperazine, pyrrolidine and tetrahydropyridine, it being understood that the covalent bond connecting $X_1$ to $X_2$ involves a ring nitrogen atom of the group $X_1$;

$X_2$ is chosen from the groups of formulae (IIIa) to (IIIc) below:

(IIIa)

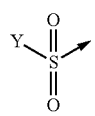
(IIIb)

(IIIc)

in which:
the arrow indicates the point of attachment of the covalent bond between $X_2$ and —NH— when n=1 or between $X_2$ and $X_1$ when n=0, $X_3$ is O or S, Y represents a group -$(T)_p$-$(CH_2)_m$—$R_1$ in which:
p and m, independently of each other, are integers equal to 0 or 1;
T is chosen from O, NH and $CH_2$; and
$R_1$ is chosen from a hydrogen atom; a linear or branched $C_2$-$C_4$ alkyl radical; a linear or branched $C_2$-$C_4$ haloalkyl radical; a $C_2$-$C_4$ alkene radical; a $C_2$-$C_4$ alkyne radical; a linear or branched $C_2$-$C_4$ alkoxy radical; a ($C_2$-$C_4$)alkylcarboxylic group; a cyano group; a saturated or unsaturated $C_3$-$C_6$ hydrocarbon-based radical optionally substituted with a $C_1$-$C_4$ alkyl radical or with a methylene bridge; an azido group; a benzyloxy group; an aromatic or heteroaromatic ring optionally substituted with one or more substituents chosen from a halogen atom and an amino, linear or branched $C_1$-$C_4$ alkyl, $C_1$-$C_4$ alkoxy or cyano group; or a triazole ring which is unsubstituted or substituted, in position 4, with a trimethylsilyl group or a group chosen from the compounds of formula (IV) below:

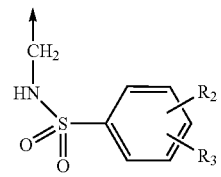
(IV)

in which:
the arrow represents the point of attachment of the compound of formula (IV) to $X_2$ via a covalent bond, $R_2$ and $R_3$, which may be identical or different, represent a hydrogen atom, a halogen atom preferably chosen from chlorine, iodine and fluorine, a $C_1$-$C_4$ alkyl group or a nitro group; when $R_2$ and $R_3$ are adjacent, they may also form a methylenedioxy group or, together with the carbon atoms of the benzene ring on which they are borne, a 6-membered carbon-based or heterocarbon-based ring, said ring being optionally substituted with a di($C_1$-$C_4$)alkylamino radical or a trifluoroacetyl radical;

the unit B is connected to L via at least one covalent bond and is chosen from aromatic hydrocarbon-based rings, polyaromatic hydrocarbon-based rings, monocyclic heteroaromatic rings containing at least one heteroatom chosen from S, O and N, saturated or unsaturated $C_3$-$C_7$ hydrocarbon-based rings, saturated or unsaturated $C_3$-$C_7$ heterocycles, and a benzothiazolyl group; said rings and said group possibly being unsubstituted or substituted with one or more substituents chosen from halogen atoms, linear or branched $C_1$-$C_4$ alkyl radicals, linear or branched $C_1$-$C_4$ alkoxy radicals, a methylenedioxy group, linear or branched $C_1$-$C_4$ haloalkyl radicals, linear or branched $C_1$-$C_4$ haloalkyloxy radicals and an amino group which is unsubstituted or substituted with one or two benzyl groups;

L represents a group that provides the bond between the two units A and B and is chosen from unsaturated 5-membered heterocycles comprising from 1 to 4 heteroatoms chosen from N, O and S, it being understood that when $R_1$ represents a linear or branched $C_2$-$C_4$ alkyloxy group and when p=1, then T is chosen from NH and $CH_2$;

for the manufacture of a medicament for preventing and/or treating bacterial and preferably mycobacterial infections.

According to the invention, the following definitions apply:
aromatic ring: any flat ring compound with conjugated pi bonds, in which each ring atom comprises a p orbital, said p orbitals overlapping,
polyaromatic ring: any cyclic compound resulting from the fusion of at least two aromatic rings as defined above.
halogen atom: any bromine, chlorine, fluorine or iodine atom.

When n=1 and when $X_1$ represents a $C_2$-$C_5$ alkyl chain, this chain is preferably chosen from ethane, propane, butane and pentane chains.

When $X_2$ represents a group of formula (IIIa), this group is then preferably a group in which $X_3$ represents O, Y represents a group -$(T)_p$-$(CH_2)_m$—$R_1$ in which p=0, m=1 and $R_1$ represents an azido or thiophenyl group that is unsubstituted or substituted with one or more halogen atoms.

Among the groups of formula (II) hereinabove, mention may be made of those in which:

n=1, $X_1$ represents a $C_2$-$C_5$ alkyl chain and $X_2$ represents a group of formula (IIIa), in which $X_3$ represents O or S, Y is a group -$(T)_p$-$(CH_2)_m$—$R_1$ in which p=1 and T represents an oxygen atom, m=1 and $R_1$ represents a linear or branched $C_2$-$C_4$ alkyl radical;

n=0, $X_1$ represents piperidine or pyrrolidine and $X_2$ represents a group of formula (IIIa) in which $X_3$ represents O or S, Y is a group -$(T)_p$-$(CH_2)_m$—$R_1$ in which p=1 and T represents an oxygen atom, m=0 and $R_1$ represents a linear or branched $C_2$-$C_4$ alkyl radical;

n=0, $X_1$ represents piperidine or piperazine and $X_2$ represents a group of formula (IIIa) in which $X_3$ represents O or S, Y is a group -$(T)_p$-$(CH_2)_m$—$R_1$ in which p=0, m=1 and $R_1$ represents an azido group, a cyano group or a heteroaromatic ring, preferably thiophene or triazole;

n=0, $X_1$ represents piperidine or piperazine and $X_2$ represents a group of formula (IIIa) in which $X_3$ represents O or S, Y is a group -$(T)_p$-$(CH_2)_m$—$R_1$ in which p=0 or 1 with T=$CH_2$, m=1 and $R_1$ represents a saturated $C_3$-$C_7$ hydrocarbon-based ring;

n=0, $X_1$ represents piperidine or piperazine and $X_2$ represents a group of formula (IIIa) in which $X_3$ represents O or S, Y is a group -$(T)_p$-$(CH_2)_m$—$R_1$ in which p=0, m=0 and $R_1$ represents a t-butyloxy radical or a benzyloxy group;

n=0, $X_1$ represents piperidine or piperazine, and $X_2$ represents a group of formula (IIIa) in which $X_3$ represents O or S, Y is a group -$(T)_p$-$(CH_2)_m$—$R_1$ in which p=0 or 1, m=1 and $R_1$ represents a triazole ring substituted with a compound of formula (IV) in which:

i) $R_2$ and $R_3$ represent a hydrogen atom, ii) $R_2$ represents a hydrogen atom and $R_3$ represents a halogen atom or a methyl radical, preferably in the para position relative to the sulfonamide function, iii) $R_2$ represents a nitro group in the ortho or meta position relative to the sulfonamide function and $R_3$, in the para position relative to the sulfonamide function, represents a hydrogen or halogen atom;

iv) $R_2$ and $R_3$, in the ortho and meta positions, form a benzene ring optionally substituted with a dimethylamino group;

v) $R_2$ and $R_3$, in the meta and para positions, form a piperidino ring in which the nitrogen atom is substituted with a trifluoroacetyl radical.

When the unit B is an aromatic hydrocarbon-based ring, said ring is preferably chosen from phenyl and phenyl substituted with one or more halogen atoms and/or one or more groups chosen from methyl, t-butyl, trifluoromethyl, trifluoromethyloxy, methyloxy, dibenzylamino and methylenedioxy groups.

When the unit B is a heterocycle, said ring is preferably chosen from thiophene, furan, 2-pyridine, aminothiazole and benzothiazole rings.

When the unit B is a saturated hydrocarbon-based ring, it preferably represents a cyclopropane.

According to the invention, the unit B is preferably chosen from phenyl, thiophenyl, furyl, 2 amino-(1-3)thiazol-5-yl, 2-pyridyl, 3-pyridyl, 4-pyridyl, 4'-t-butylphenyl, 4'-trifluoromethylphenyl, 2',3'-methylenedioxyphenyl, 4'-fluorophenyl, 2'-methyl-3'-chlorophenyl, 2'-trifluoromethyl-5'-fluorophenyl, 2'-trifluoromethyloxyphenyl, 2',5'-difluorophenyl, 2'-chlorophenyl, 2'-methyl-oxyphenyl, cyclopropanyl and benzothiazolyl groups.

According to one particularly preferred embodiment of the invention, the unit B is chosen from thiophenyl, phenyl, fluorophenyl, aminothiazolyl, benzothiazolyl and 2-pyridyl groups.

According to the invention, when L represents an unsaturated 5-membered heterocycle, it is preferably chosen from oxadiazole, triazole, isoxazole, imidazole, thiadiazole, pyrrole, tetrazole, furan, thiophene, pyrazole and thiazole rings.

As compounds of formula (I) used in accordance with the invention, mention may be made in particular of:

a) the compounds corresponding to formula (I-a) below:

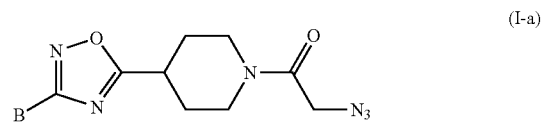

(I-a)

in which the unit B is chosen from the groups of formulae (B-1) to (B-21) below:

(B-1)

(B-2)

(B-3)

(B-4)

(B-5)

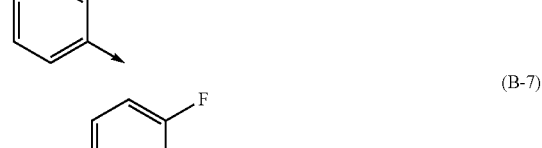

(B-6)

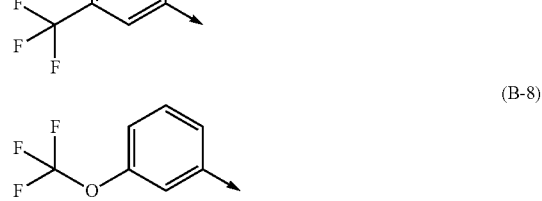

(B-7)

(B-8)

-continued
(B-9) 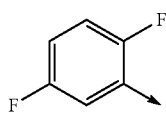
(B-10) 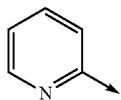
(B-11) 
(B-12) 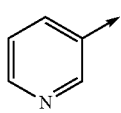
(B-13) 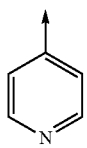
(B-14) 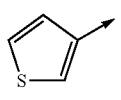
(B-15) 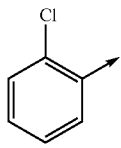
(B-16) 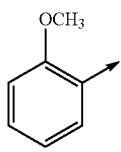
(B-17) 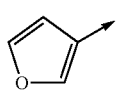
(B-18) 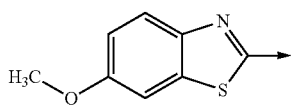
(B-19) 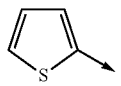
(B-20) 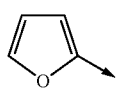
(B-21) 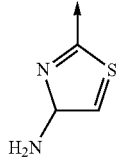
b) the compounds corresponding to formula (I-b) below:
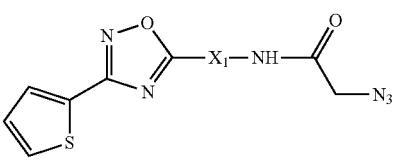
(I-b)
in which $X_1$ is chosen from the groups of formulae ($X_1$-1) to ($X_1$-4) below:
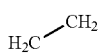
($X_1$-1)
($X_1$-2)
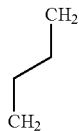
($X_1$-3)
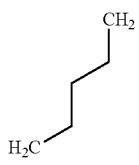
($X_1$-4)
c) the compounds corresponding to formula (I-c) below:
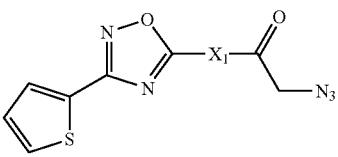
(I-c)
in which $X_1$ is chosen from the groups of formulae ($X_1$-5) to ($X_1$-10) below:
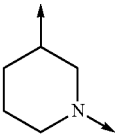
($X_1$-5)
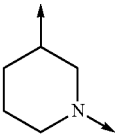
($X_1$-6)
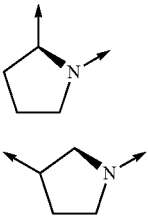
($X_1$-7)

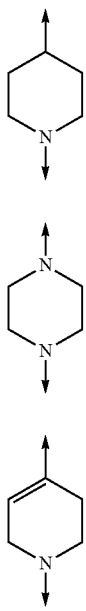
(X₁-8)
(X₁-9)
(X₁-10)
d) the compounds corresponding to formula (I-d) below:
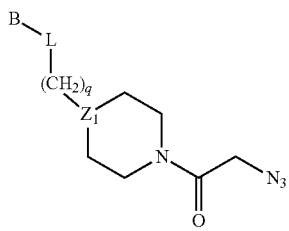
(I-d)
in which:
the unit B is a thiophenyl, phenyl, aminothiazolyl, benzothiazolyl or 2-pyridyl group,
L is a heterocycle chosen from the rings of formulae (L-1) to (L-25) below:
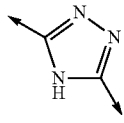 (L-1)
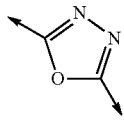 (L-2)
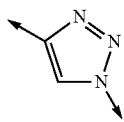 (L-3)
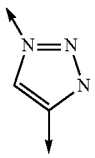 (L-4)
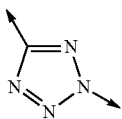 (L-5)
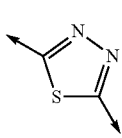 (L-6)
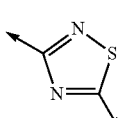 (L-7)
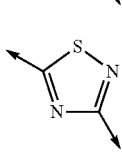 (L-8)
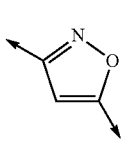 (L-9)
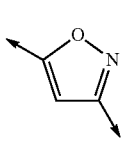 (L-10)
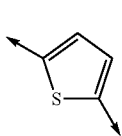 (L-11)
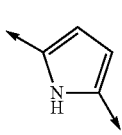 (L-12)
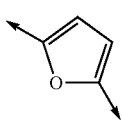 (L-13)
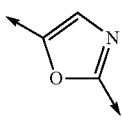 (L-14)
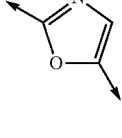 (L-15)

-continued (L-16)

(L-17)

(L-18)

(L-19)

(L-20)

(L-21)

(L-22)

(L-23)

(L-24) and (L-25)

q is an integer equal to 0 or 1, and
$Z_1$ represents a carbon or nitrogen atom, it being understood that when $Z_1$ is a carbon atom, then q=0;
e) the compounds corresponding to formula (I-e) below:

(I-e)

in which $X_2$ is chosen from the groups ($X_2$-1) to ($X_2$-23) below:

($X_2$-1)

($X_2$-2)

($X_2$-3)

($X_2$-4)

($X_2$-5)

($X_2$-6)

($X_2$-7)

($X_2$-8)

($X_2$-9)

($X_2$-10)

($X_2$-11)

($X_2$-12)

($X_2$-13)

13

-continued

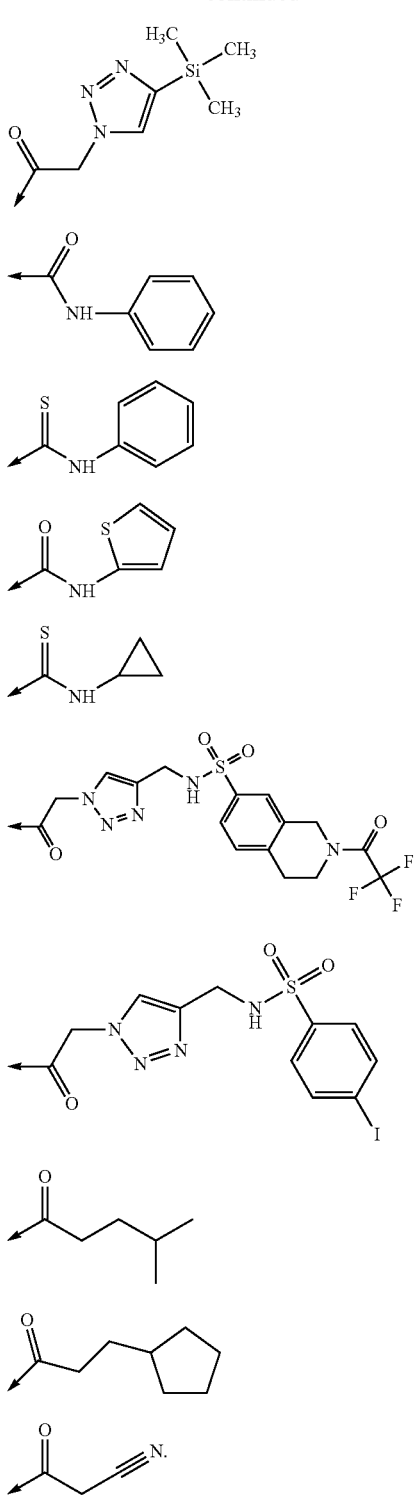

(X₂-14)
(X₂-15)
(X₂-16)
(X₂-17)
(X₂-18)
(X₂-19)
(X₂-20)
(X-21)
(X-22)
(X-23)

Among the compounds of formula (I-d) hereinabove, those in which the unit B represents a thiophenyl group are particularly preferred.

As compounds of formula (I) in accordance with the invention, mention may be made of:
2-azido-1-[4-(3-thiophen-2-yl[1,2,4]oxadiazol-5-yl)piperid-1-yl]ethanone (illustrated by formula (I-1) in Example 2 hereinbelow);

14

2-azido-1-[4-(3-cyclopropyl[1,2,4]oxadiazol-5-yl)piperid-1-yl]ethanone (compound 14);
2-azido-1-[4-(3-pyrid-2-yl[1,2,4]oxadiazol-5-yl)piperid-1-yl]ethanone (compound 13):
2-azido-1-{4-[3-(3-chloro-2-methylphenyl)[1,2,4]oxadiazol-5-yl]piperid-1-yl}-ethanone (compound 6);
2-azido-1-[4-(3-pyrid-3-yl[1,2,4]oxadiazol-5-yl)piperid-1-yl]ethanone;
2-azido-1-{4-[3-(2-fluoro-5-trifluoromethylphenyl)[1,2,4]oxadiazol-5-yl]piperid-1-yl}ethanone;
2-azido-1-{4-[3-(2,5-difluorophenyl)[1,2,4]oxadiazol-5-yl]piperid-1-yl}ethanone (compound 7);
2-azido-1-{4-[3-(2-methoxyphenyl)[1,2,4]oxadiazol-5-yl]piperid-1-yl}ethanone (compound 11);
2-azido-1-{4-[3-(2-chlorophenyl)[1,2,4]oxadiazol-5-yl]piperid-1-yl}ethanone (compound 10);
2-azido-1-[4-(3-phenyl[1,2,4]oxadiazol-5-yl)piperid-1-yl]ethanone (compound 4);
2-azido-1-{4-[3-(3-trifluoromethoxyphenyl)[1,2,4]oxadiazol-5-yl]piperid-1-yl}-ethanone;
2-azido-1-{4-[3-(4-tert-butylphenyl)[1,2,4]oxadiazol-5-yl]piperid-1-yl}ethanone (compound 9);
2-azido-1-{4-[3-(4-trifluoromethylphenyl)[1,2,4]oxadiazol-5-yl]piperid-1-yl}-ethanone (compound 8);
2-azido-1-[4-(3-benzo[1,3]dioxol-5-yl[1,2,4]oxadiazol-5-yl)piperid-1-yl]ethanone (compound 12);
2-azido-1-[4-(3-furan-2-yl[1,2,4]oxadiazol-5-yl)piperid-1-yl]ethanone (compound 2);
2-azido-1-{4-[3-(4-fluorophenyl)[1,2,4]oxadiazol-5-yl]piperid-1-yl}ethanone (compound 5);
2-azido-1-[4-(3-thiophen-3-yl[1,2,4]oxadiazol-5-yl)piperid-1-yl]ethanone (compound 3);
2-azido-1-[4-(3-(6-methoxybenzothiazol-2-yl[1,2,4]oxadiazol-5-yl)piperid-1-yl]ethanone (compound 15);
1-[4-(3-thiophen-2-yl[1,2,4]oxadiazol-5-yl)piperid-1-yl]-2-[1,2,3]triazol-1-yl-ethanone (illustrated by formula (I-2) in Example 3 hereinbelow);
the t-butyl ester of 4-(3-thiophen-2-yl-1,2,4-oxadiazol-5-yl)piperidine-1-carboxylic acid (illustrated by formula (I-3) in Example 1 hereinbelow);
the t-butyl ester of 4-(3-cyclopropyl[1,2,4-]oxadiazol-5-yl)piperidine-1-carboxylic acid;
the t-butyl ester of 4-(3-pyrid-2-yl[1,2,4]oxadiazol-5-yl)piperidine-1-carboxylic acid;
the t-butyl ester of 4-[3-(3-chloro-2-methylphenyl)[1,2,4]oxadiazol-5-yl]-piperidine-1-carboxylic acid;
the t-butyl ester of 4-(3-pyrid-3-yl[1,2,4]oxadiazol-5-yl)piperidine-1-carboxylic acid;
the t-butyl ester of 4-[3-(2-fluoro-5-trifluoromethylphenyl)[1,2,4]oxadiazol-5-yl]piperidine-1-carboxylic acid;
the t-butyl ester of 4-[3-(2,5-difluorophenyl)[1,2,4]oxadiazol-5-yl]piperidine-1-carboxylic acid;
the t-butyl ester of 4-[3-(2-methoxyphenyl)[1,2,4]oxadiazol-5-yl]piperidine-1-carboxylic acid;
the t-butyl ester of 4-[3-(2-chlorophenyl)[1,2,4]oxadiazol-5-yl]piperidine-1-carboxylic acid;
the t-butyl ester of 4-(3-phenyl)[1,2,4]oxadiazol-5-yl]piperidine-1-carboxylic acid;
the t-butyl ester of 4-[3-(3-trifluoromethoxyphenyl)[1,2,4]oxadiazol-5-yl]-piperidine-1-carboxylic acid;
the t-butyl ester of 4-[3-(4-tert-butylphenyl)[1,2,4]oxadiazol-5-yl]piperidine-1-carboxylic acid;
the t-butyl ester of 4-[3-(4-trifluoromethylphenyl)[1,2,4]oxadiazol-5-yl]-piperidine-1-carboxylic acid;
the t-butyl ester of 4-(3-benzo[1,3]dioxol-5-yl[1,2,4]oxadiazol-5-yl)piperidine-1-carboxylic acid;

the t-butyl ester of 4-(3-furan-2-yl[1,2,4]oxadiazol-5-yl)piperidine-1-carboxylic acid;
the t-butyl ester of 4-[3-(4-fluorophenyl)[1,2,4]oxadiazol-5-yl)piperidine-1-carboxylic acid;
the t-butyl ester of 4-(3-thiophen-3-yl[1,2,4]oxadiazol-5-yl) piperidine-1-carboxylic acid;
the t-butyl ester of 3-(3-thiophen-2-yl[1,2,4]oxadiazol-5-yl) piperidine-1-carboxylic acid;
the t-butyl ester of 2-(3-thiophen-2-yl[1,2,4]oxadiazol-5-yl) pyrrolidine-1-carboxylic acid;
the t-butyl ester of 4-[3-(6-methoxybenzothiazol-2-yl)[1,2,4]oxadiazol-5-yl]-piperidine-1-carboxylic acid;
the t-butyl ester of [2-(3-thiophen-2-yl[1,2,4]oxadiazol-5-yl) ethyl]carbamic acid;
the t-butyl ester of [3-(3-thiophen-2-yl[1,2,4]oxadiazol-5-yl) propyl]carbamic acid;
the t-butyl ester of [4-(3-thiophen-2-yl[1,2,4]oxadiazol-5-yl) butyl]carbamic acid;
the t-butyl ester of [5-(3-thiophen-2-yl[1,2,4]oxadiazol-5-yl) pentyl]carbamic acid;
4-iodo-N-(1-{2-oxo-2-[4-(3-thiophen-2-yl[1,2,4]oxadiazol-5-yl)piperid-1-yl]-ethyl}-1H-1,2,3-triazol-4-ylmethyl) benzenesulfonamide (illustrated by formula (I-4) in Example 4 hereinbelow);
the t-butyl ester of 4-(3-thiophen-2-yl[1,2,4]oxadiazol-5-ylmethyl)piperazine-1-carboxylic acid (illustrated by formula (I-5) in Example 5 hereinbelow);
the t-butyl ester of 4-(5-thiophen-2-yl[1,2,4]oxadiazol-3-ylmethyl)piperazine-1-carboxylic acid (illustrated by formula (I-6) in Example 6 hereinbelow);
the t-butyl ester of 4-(5-thiophen-2-yl-4H-[1,2,4]triazol-3-yl)piperidine-1-carboxylic acid (illustrated by formula (I-7) in Example 7 hereinbelow);
1-[4-(3-thiophen-2-yl[1,2,4]oxadiazol-5-yl)piperid-1-yl]-2-[1,2,3]triazol-1-ylethanone of formula (I-8) below:

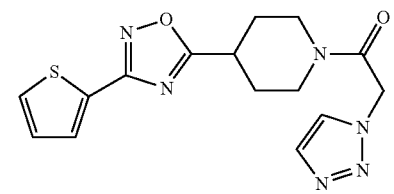

(I-8)

2-(2,2,2-trifluoroacetyl)-1,2,3,4-tetrahydroisoquinoline-7-sulfonic acid (1-{2-oxo-2-[4-(3-thiophen-2-yl[1,2,4]oxadiazol-5-yl)piperid-1-yl]ethyl}-1H-[1,2,3]triazol-4-ylmethyl)amide of formula (I-9) below:

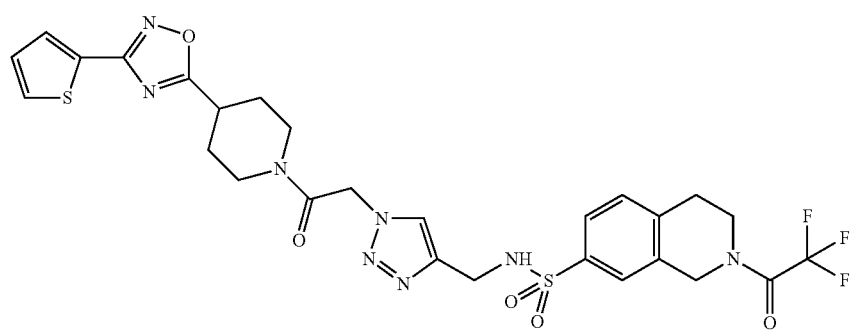

(I-9)

2-azido-1-[4-(3-thiophen-2-yl[1,2,4]oxadiazol-5-ylmethyl) piperazin-1-yl]ethanone of formula (I-10) below:

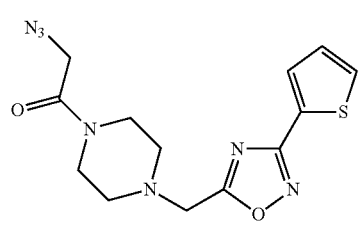

(I-10)

1-[4-(3-thiophen-2-yl[1,2,4]oxadiazol-5-ylmethyl)piperazin-1-yl]-2-[1,2,3]triazol-1-ylethanone of formula (I-11) below:

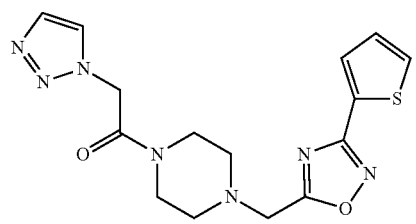

(I-11)

2-azido-1-[4-(5-thiophen-2-yl[1,2,4]oxadiazol-3-ylmethyl) piperazin-1-yl]ethanone of formula (I-12) below:

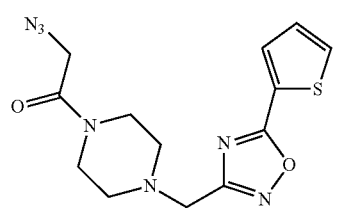

(I-12)

1-[4-(5-thiophen-2-yl[1,2,4]oxadiazol-3-ylmethyl)piperazin-1-yl]-2-[1,2,3]-triazol-1-ylethanone of formula (I-13) below:

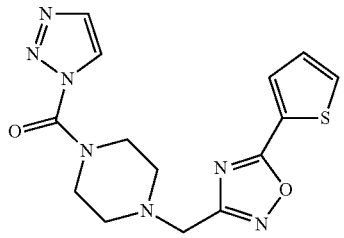

(I-13)

2-azido-1-[4-(5-thiophen-2-yl-4H-[1,2,4]triazol-3-yl)piperid-1-yl]ethanone of formula (I-14) below:

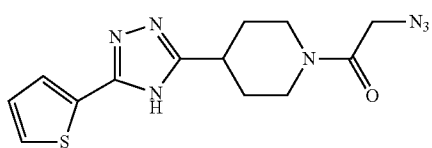

(I-14)

1-[4-(5-thiophen-2-yl-4H-[1,2,4]triazol-3-yl)piperid-1-yl]-2-[1,2,3]triazol-1-ylethanone of formula (I-15) below:

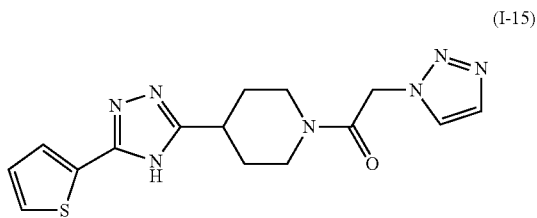

(I-15)

2-azido-1-[4-(3-thiophen-3-yl[1,2,4]oxadiazol-5-yl)piperid-1-yl]ethanone of formula (I-16) below:

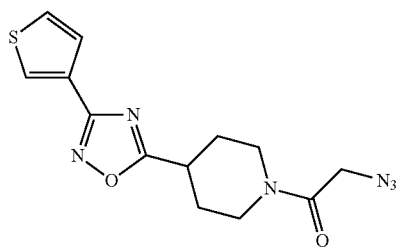

(I-16)

1-[4-(3-thiophen-3-yl[1,2,4]oxadiazol-5-yl)piperid-1-yl]-2-[1,2,3]triazol-1-yl-ethanone of formula (I-17) below:

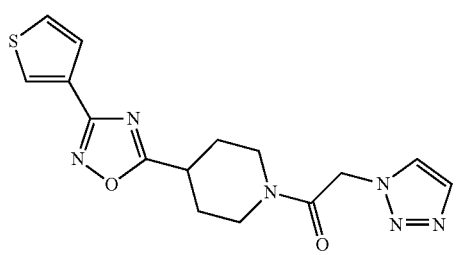

(I-17)

2-azido-1-[4-(3-furan-2-yl[1,2,4]oxadiazol-5-yl)piperid-1-yl]ethanone of formula (I-18) below:

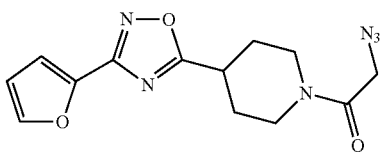

(I-18)

1-[4-(3-furan-2-yl[1,2,4]oxadiazol-5-yl)piperid-1-yl]-2-[1,2,3]triazol-1-ylethanone of formula (I-19) below:

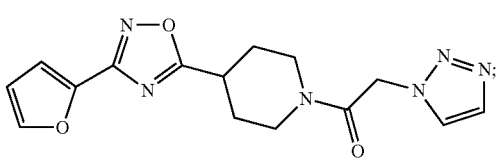

(I-19)

the allylic ester of 4-(3-thiophen-2-yl[1,2,4]oxadiazol-5-yl)piperidine-1-carboxylic acid;
2-phenoxy-1-[4-(3-thiophen-2-yl[1,2,4]oxadiazol-5-yl)piperid-1-yl]ethanone (Compound 45);
1-[4-(3-thiophen-2-yl[1,2,4]oxadiazol-5-yl)piperid-1-yl]propan-1-one (Compound 23);
3-cyclopentyl-1-[4-(3-thiophen-2-yl[1,2,4]oxadiazol-5-yl)piperid-1-yl]propan-1-one (Compound 34);
3,3-dimethyl-1-[4-(3-thiophen-2-yl[1,2,4]oxadiazol-5-yl)piperid-1-yl]butan-1-one (Compound 26);
2-thiophen-2-yl-1-[4-(3-thiophen-2-yl[1,2,4]oxadiazol-5-yl)piperid-1-yl]ethanone (Compound 43);
3-methyl-1-[4-(3-thiophen-2-yl[1,2,4]oxadiazol-5-yl)piperid-1-yl]butan-1-one (Compound 24);
4-methyl-1-[4-(3-thiophen-2-yl[1,2,4]oxadiazol-5-yl)piperid-1-yl]pentan-1-one (Compound 25);
2-bicyclo[2.2.1]hept-2-yl-1-[4-(3-thiophen-2-yl[1,2,4]oxadiazol-5-yl)piperid-1-yl]ethanone (Compound 40);
2-cyclopropyl-1-[4-(3-thiophen-2-yl[1,2,4]oxadiazol-5-yl)piperid-1-yl]ethanone (Compound 33);
3-cyclohexyl-1-[4-(3-thiophen-2-yl[1,2,4]oxadiazol-5-yl)piperid-1-yl]propan-1-one (Compound 38);
2-phenyl-1-[4-(3-thiophen-2-yl[1,2,4]oxadiazol-5-yl)piperid-1-yl]ethanone (compound 41);
3-phenyl-1-[4-(3-thiophen-2-yl[1,2,4]oxadiazol-5-yl)piperid-1-yl]propan-1-one (Compound 42);
2-cyclohexyl-1-[4-(3-thiophen-2-yl[1,2,4]oxadiazol-5-yl)piperid-1-yl]ethanone (Compound 37);
2-cyclopent-2-enyl-1-[4-(3-thiophen-2-yl[1,2,4]oxadiazol-5-yl)piperid-1-yl]-ethanone (Compound 36);
2-(4-methylcyclohexyl)-1-[4-(3-thiophen-2-yl[1,2,4]oxadiazol-5-yl)piperid-1-yl]-ethanone (Compound 39);
3-tert-butoxy-1-[4-(3-thiophen-2-yl[1,2,4]oxadiazol-5-yl)piperid-1-yl]propan-1-one (compound 30);
2-cyclopentyl-1-[4-(3-thiophen-2-yl[1,2,4]oxadiazol-5-yl)piperid-1-yl]ethanone (Compound 35);
4,4,4-trifluoro-1-[4-(3-thiophen-2-yl[1,2,4]oxadiazol-5-yl)piperid-1-yl]butan-1-one (Compound 27);
1-[4-(3-thiophen-2-yl[1,2,4]oxadiazol-5-yl)piperid-1-yl]pent-4-en-1-one (Compound 20);
1-[4-(3-thiophen-2-yl[1,2,4]oxadiazol-5-yl)piperid-1-yl]pent-4-yn-1-one (Compound 21);
3-oxo-3-[4-(3-thiophen-2-yl[1,2,4]oxadiazol-5-yl)piperid-1-yl]propionitrile (Compound 22);

2-methoxy-1-[4-(3-thiophen-2-yl[1,2,4]oxadiazol-5-yl)piperid-1-yl]ethanone (Compound 28);
3-methoxy-1-[4-(3-thiophen-2-yl[1,2,4]oxadiazol-5-yl)piperid-1-yl]propan-1-one (Compound 29);
1-[4-(3-thiophen-2-yl[1,2,4]oxadiazol-5-yl)piperid-1-yl]ethanone (Compound 17);
4-oxo-4-[4-(3-thiophen-2-yl[1,2,4]oxadiazol-5-yl)piperid-1-yl]butyric acid (Compound 31);
5-oxo-5-[4-(3-thiophen-2-yl[1,2,4]oxadiazol-5-yl)piperid-1-yl]pentanoic acid (Compound 32);
4-(3-thiophen-2-yl[1,2,4]oxadiazol-5-yl)piperidine-1-carboxylic acid phenylamide (Compound 48);
4-(3-thiophen-2-yl[1,2,4]oxadiazol-5-yl)piperidine-1-carbothioic acid phenylamide (Compound 49);
4-(3-thiophen-2-yl[1,2,4]oxadiazol-5-yl)piperidine-1-carboxylic acid thiophen-2-ylamide (Compound 50);
4-(3-thiophen-2-yl[1,2,4]oxadiazol-5-yl)piperidine-1-carbothioic acid cyclopropylamide (Compound 52);
4-(3-thiophen-2-yl[1,2,4]oxadiazol-5-yl)piperidine-1-carboxylic acid cyclopropylamide (Compound 51);
1-phenylmethanesulfonyl-4-(3-thiophen-2-yl[1,2,4]oxadiazol-5-yl)piperidine (Compound 53);
1-(thiophene-3-sulfonyl)-4-(3-thiophen-2-yl[1,2,4]oxadiazol-5-yl)piperidine;
phenyl[4-(3-thiophen-2-yl[1,2,4]oxadiazol-5-yl)piperid-1-yl]methanone (Compound 54);
2-thiophen-3-yl-1-[4-(3-thiophen-2-yl[1,2,4]triazol-5-yl)piperid-1-yl]ethanone (Compound 60);
1-{4-[3-(5-bromothiophen-2-yl)[1,2,4]oxadiazol-5-yl]piperid-1-yl}-2-thiophen-2-ylethanone (compound 58);
3-{4-[3-(5-bromothiophen-2-yl)[1,2,4]oxadiazol-5-yl]piperid-1-yl}-3-oxo-propionitrile (compound 59);
2-(2-aminothiazol-4-yl)-1-[4-(3-thiophen-2-yl[1,2,4]oxadiazol-5-yl)piperid-1-yl]ethanone;
1-{4-[3-(2-aminothiazol-5-yl)[1,2,4]oxadiazol-5-yl]piperid-1-yl}-2-cyclopropyl-ethanone;
2-cyclopropyl-1-{4-[3-(3-dibenzylaminophenyl)[1,2,4]oxadiazol-5-yl]piperid-1-yl}ethanone (compound 57);
2-(1H-tetrazol-5-yl)-1-[4-(3-thiophen-2-yl[1,2,4]oxadiazol-5-yl)piperid-1-yl]-ethanone (compound 61);
2-(2-chlorophenyl)-1-[4-(3-thiophen-2-yl[1,2,4]oxadiazol-5-yl)piperid-1-yl]-ethanone (compound 62);
2-(2,6-dichlorophenyl)-1-[4-(3-thiophen-2-yl[1,2,4]oxadiazol-5-yl)piperid-1-yl]-ethanone (compound 63); and
2-pyrid-4-yl-1-[4-(3-thiophen-2-yl[1,2,4]oxadiazol-5-yl)piperid-1-yl]ethanone (compound 64).

The compounds of formula (I) as defined above are particularly effective for preventing and/or treating tuberculosis, leprosy or atypical mycobacterioses.

Consequently, according to one advantageous embodiment of the invention, said medicament is intended for preventing and/or treating tuberculosis, leprosy or atypical mycobacterioses.

The compounds of formula (I) used in accordance with the invention have the property of potentiating the activity of the antibiotic ethionamide with respect to mycobacterial strains, while at the same time being much easier to formulate than hexadecyl octanoate.

Consequently, according to one preferred embodiment of the invention, said compounds of formula (I) are used for the preparation of a medicament also comprising at least one antibiotic chosen from antibiotics that are activatable via the EthA enzymatic pathway.

In this case, said antibiotic is preferably chosen from ethionamide, prothionamide, isoxyl and thiacetazone.

The compounds of formula (I) as defined above may be incorporated into a pharmaceutical composition for preventing and/or treating mycobacterial infections.

The invention thus also relates to a pharmaceutical composition comprising, as active principle, at least one compound of formula (I) as defined above, at least one pharmaceutically acceptable excipient and at least one antibiotic that is activatable via the EthA enzymatic pathway.

In this case, the antibiotic is preferably chosen from ethionamide, prothionamide, isoxyl and thiacetazone.

In the pharmaceutical compositions in accordance with the invention, the compound(s) of formula (I) is (are) preferably used in an amount allowing the administration of unit doses of between 1 mg and 1 g approximately.

In the pharmaceutical compositions in accordance with the invention, the antibiotic(s) that is (are) activatable via the EthA enzymatic pathway is (are) used in an amount allowing the administration of unit doses less than or equal to the doses usually recommended by the WHO (WHO, Treatment of tuberculosis: Guidelines for National Programmes. 2003; WHO/CDS/TB2003.313.), national or nongovernmental health organizations, or competent pharmaceutical laboratories.

The compounds of formula (I) used in accordance with the invention have the advantage of allowing a reduction of the effective dose of the antibiotic used by a factor ranging from 2 to 100. In the case of the combination with ETH, the compounds of formula (I) used in accordance with the invention make it possible in particular to reduce the effective dose by a factor ranging from 2 to 50.

When the compound of formula (I) is the compound of formula (I-3), this factor is about 10-fold; when it is the compound of formula (I-1), this factor is between 10 and 20-fold approximately; when it is compound 33, this factor is about 20-fold; when it is compound 43, this factor is about 40-fold; when it is compound 20, this factor is about 20-fold, and when it is compound 22, this factor is about 10-fold.

A person skilled in the art will select one or more pharmaceutically acceptable excipients as a function of the route of administration of the pharmaceutical composition.

Needless to say, a person skilled in the art will take care at that time to ensure that the excipient(s) used is (are) compatible with the intrinsic properties associated with the composition in accordance with the present invention.

In addition, the form of the medicament or of the pharmaceutical composition (for example a solution, a suspension, an emulsion, tablets, gel capsules, suppositories, etc.) will depend on the chosen route of administration.

Thus, for the purposes of the present invention, the medicament or the pharmaceutical composition may be administered via any suitable route, for example via the oral, anal, local, systemic, intravenous, intramuscular or mucosal route, or alternatively using a patch, or else in encapsulated form in, or immobilized on, liposomes, microparticles, microcapsules, and the like.

Nonlimiting examples of excipients that are suitable for oral administration especially include talc, lactose, starch and its derivatives, cellulose and its derivatives, polyethylene glycols, acrylic acid polymers, gelatin, magnesium stearate, animal, plant or synthetic fats, paraffin derivatives, glycols, stabilizers, preserving agents, antioxidants, wetting agents, anticaking agents, dispersants, emulsifiers, flavor enhancers, penetrants, solubilizers, etc.

The techniques for formulating and administering medicaments and pharmaceutical compositions are well known in the art under consideration herein, and a person skilled in the art may especially refer to the latest edition of "Remington's Pharmaceutical Sciences".

In addition, the invention also relates to products containing at least one compound of formula (I) as defined previously and at least one antibiotic chosen from antibiotics that are activatable via the EthA enzymatic pathway, in particular from ETH, prothionamide, isoxyl and thiacetazone, as combination products for simultaneous, separate or sequential use over time in general anti-tuberculous, anti-lepromatous or anti-mycobacterial therapy.

Certain compounds of formula (I) as described hereinabove are novel per se and, in this respect, constitute another subject of the invention.

These compounds correspond to formula (I') below:

$$A'\text{-}L'\text{-}B' \quad (I')$$

in which:
the unit A' is connected to L' via at least one covalent bond and is chosen from the groups of formula (II') below:

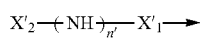

(II')

in which:
the arrow indicates the point of attachment of the covalent bond connecting $X'_1$ to L', said bond involving at least one carbon atom of the group $X'_1$ and a carbon, nitrogen or oxygen atom of the group L', n' is an integer equal to 0 or 1, when n'=1, $X'_1$ represents a group chosen from $C_2$-$C_5$ alkyl chains; it being understood that a carbon atom of the group $X'_1$ is engaged in the covalent bond connecting $X'_1$ to —NH—, when n'=0, $X'_1$ represents piperidine, piperazine or tetrahydropyridine, it being understood that the covalent bond connecting $X'_1$ to $X'_2$ involves a ring nitrogen atom of the group $X'_1$ and when $X'_1$ represents piperidine or piperazine, then the bond between $X'_1$ and L' is a 1→4 bond;

$X'_2$ is chosen from the groups of formulae (III'a) and (III'b) below:

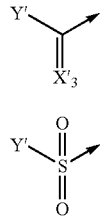

in which:
the arrow indicates the point of attachment of the covalent bond between $X'_2$ and —NH— when n'=1 or between $X'_2$ and $X'_1$ when n'=0, $X'_3$ is O or S, Y' represents a group -(T')$_{p'}$-(CH$_2$)$_{m'}$—R'$_1$ in which:
p' and m', independently of each other, are integers equal to 0 or 1;
T' is chosen from O, NH and CH$_2$; and
R'$_1$ is chosen from a hydrogen atom; a linear or branched $C_2$-$C_4$ alkyl radical; a linear or branched $C_2$-$C_4$ haloalkyl radical; a $C_2$-$C_4$ alkene radical; a $C_2$-$C_4$ alkyne radical; a linear $C_2$-$C_4$ alkoxy radical; a ($C_2$-$C_4$)alkylcarboxylic group; a cyano group; a saturated or unsaturated $C_3$-$C_6$ hydrocarbon-based ring optionally substituted with a $C_1$-$C_4$ alkyl radical or with a methylene bridge; an azido group; a benzyloxy group; an aromatic or heteroaromatic ring optionally substituted with one or more substituents chosen from a halogen atom and an amino, linear or branched $C_1$-$C_4$ alkyl, $C_1$-$C_4$ alkoxy or cyano group; or a triazole ring which is unsubstituted or substituted, in position 4, with a trimethylsilyl group or a group chosen from the compounds of formula (IV') below:

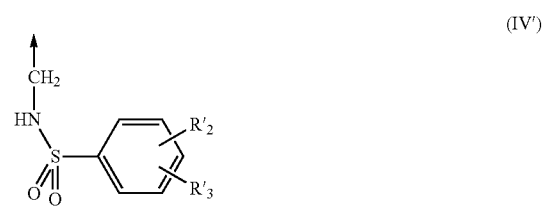

(IV')

in which:
the arrow represents the point of attachment of the compound of formula (IV') to $X'_2$ via a covalent bond, $R'_2$ and $R'_3$, which may be identical or different, represent a hydrogen atom, a halogen atom preferably chosen from chlorine, iodine and fluorine, a $C_1$-$C_4$ alkyl group or a nitro group; when $R'_2$ and $R'_3$ are adjacent, they may also form a methylenedioxy group or, together with the carbon atoms of the benzene ring on which they are borne, a 6-membered carbon-based or heterocarbon-based ring, said ring being optionally substituted with a di($C_1$-$C_4$)alkylamino radical or a trifluoroacetyl radical;

the unit B' is connected to L' via at least one covalent bond and is chosen from aromatic hydrocarbon-based rings, polyaromatic hydrocarbon-based rings, $C_5$ heteroaromatic rings containing at least one heteroatom chosen from S, O and N, pyrid-2-yl, saturated or unsaturated $C_3$-$C_7$ hydrocarbon-based rings, saturated or unsaturated $C_3$-$C_7$ heterocycles, and a benzothiazolyl group; said rings or said group possibly being unsubstituted or substituted with one or more substituents chosen from halogen atoms, linear or branched $C_1$-$C_4$ alkyl radicals, linear or branched $C_1$-$C_4$ alkoxy radicals, a methylenedioxy group, linear or branched $C_1$-$C_4$ haloalkyl radicals, linear or branched $C_1$-$C_4$ haloalkoxy radicals and an amino group which is unsubstituted or substituted with one or two benzyl groups;

L' represents a group that provides the bond between the two units A' and B' and is chosen from unsaturated 5-membered heterocycles comprising from 1 to 4 heteroatoms chosen from N, O and S;

it being understood that when R'$_1$ represents a linear or branched $C_2$-$C_4$ alkoxy group and when p'=1, then T' is chosen from NH and CH$_2$.

When n'=1 and when $X_1$' represents a $C_2$-$C_5$ alkyl chain, this chain is preferably chosen from ethane, propane, butane and pentane chains.

When $X_2$' represents a group of formula (III'a), this group is then preferably a group in which $X_3$' represents O, Y' represents a group -(T')$_{p'}$-(CH$_2$)$_{m'}$—R'$_1$ in which p'=0, m'=1 and R'$_1$ represents an azido or thiophenyl group that is unsubstituted or substituted with one or more halogen atoms.

Among the groups of formula (II') hereinabove, mention may be made of those in which:

n'=1, X'$_1$ represents a C$_2$-C$_5$ alkyl chain and X'$_2$ represents a group of formula (III'a) in which, X'$_3$ represents O or S, Y' is a group -(T')$_{p'}$-(CH$_2$)$_{m'}$—R'$_1$ in which p'=1 and T represents an oxygen atom, m'=1 and R'$_1$ represents a linear or branched C$_2$-C$_4$ alkyl radical;

n'=0, X'$_1$ represents piperidine or piperazine that is 1,4-substituted and X'$_2$ represents a group of formula (III'a) in which X'$_3$ represents O or S, Y' is a group -(T')$_{p'}$-(CH$_2$)$_{m'}$—R'$_1$ in which p'=0, m'=1 and R'$_1$ represents an azido group, a cyano group or a heteroaromatic ring, preferably thiophene or triazole;

n'=0, X'$_1$ represents piperidine or piperazine that is 1,4-substituted and X'$_2$ represents a group of formula (III'a) in which X'$_3$ represents O or S, Y' is a group -(T')$_{p'}$-(CH$_2$)$_{m'}$—R'$_1$ in which p'=1 and T'=CH$_2$, m'=1 and R'$_1$ represents a saturated C$_3$-C$_7$ hydrocarbon-based ring;

n'=0, X'$_1$ represents piperidine or piperazine that is 1,4-substituted and X'$_2$ represents a group of formula (III'a) in which X'$_3$ represents O or S, Y' is a group -(T')$_{p'}$-(CH$_2$)$_{m'}$—R'$_1$ in which p'=0, m'=0 and R'$_1$ represents a benzyloxy group;

n'=0, X'$_1$ represents piperidine or piperazine that is 1,4-substituted, and X'$_2$ represents a group of formula (III'a) in which X'$_3$ represents O or S, Y' is a group -(T')$_{p'}$-(CH$_2$)$_{m'}$—R'$_1$ in which p'=0 or 1, m'=1 and R'$_1$ represents a triazole ring substituted with a compound of formula (IV') in which:

i) R'$_2$ and R'$_3$ represent a hydrogen atom, ii) R'$_2$ represents a hydrogen atom and R'$_3$ represents a halogen atom or a methyl radical, preferably in the para position relative to the sulfonamide function, iii) R'$_2$ represents a nitro group in the ortho or meta position relative to the sulfonamide function and R'$_3$, in the para position relative to the sulfonamide function, represents a hydrogen or halogen atom;

iv) R'$_2$ and R'$_3$, in the ortho and meta positions, form a benzene ring optionally substituted with a dimethylamino group;

v) R'$_2$ and R'$_3$, in the meta and para positions, form a piperidino ring in which the nitrogen atom is substituted with a trifluoroacetyl radical.

When the unit B' is an aromatic hydrocarbon-based ring, said ring is preferably chosen from phenyl and phenyl substituted with one or more halogen atoms and/or one or more groups chosen from methyl, t-butyl, trifluoromethyl, trifluoromethyloxy, methyloxy, dibenzylamino and methylenedioxy groups.

When the unit B' is a heterocycle, said ring is preferably chosen from thiophene, furan, 2-pyridine, aminothiazole and benzothiazole rings.

When the unit B' is a saturated hydrocarbon-based ring, it preferably represents a cyclopropane.

According to the invention, the unit B' is preferably chosen from phenyl, thiophenyl, furyl, 2-amino-(1-3)thiazol-5-yl, pyrid-2-yl, 4'-t-butylphenyl, 4'-trifluoromethylphenyl, 2',3'-methylenedioxyphenyl, 4'-fluorophenyl, 2'-methyl-3'-chlorophenyl, 2'-trifluoromethyl-5'-fluorophenyl, 2'-trifluoromethyloxyphenyl, 2',5'-difluorophenyl, 2'-chlorophenyl, 2'-methyloxyphenyl, cyclopropanyl and benzothiazolyl groups.

According to one particularly preferred embodiment of the invention, the unit B' is chosen from thiophenyl, phenyl, fluorophenyl, aminothiazolyl, benzothiazolyl and pyrid-2-yl groups.

According to the invention, when L' represents an unsaturated 5-membered heterocycle, it is preferably chosen from oxadiazole, triazole, isoxazole, imidazole, thiadiazole, pyrrole, tetrazole, furan, thiophene, pyrazole and thiazole rings.

As compounds of formula (I') that are used in accordance with the invention, mention may be made in particular of:

a) the compounds corresponding to formula (I'-a) below:

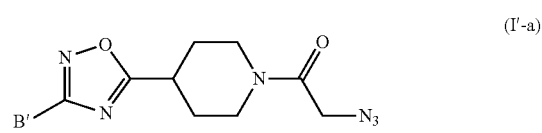

(I'-a)

in which the unit B' is chosen from the groups of formulae (B'-1) to (B'-11) and (B'-14) to (B'-21) below:

(B'-1)

(B'-2)

(B'-3)

(B'-4)

(B'-5)

(B'-6)

(B'-7)

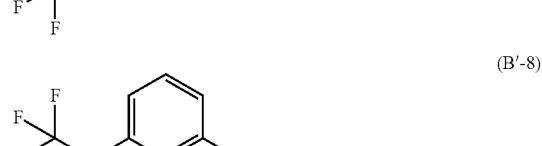

(B'-8)

-continued (B'-9) 2,5-difluorophenyl (B'-10) pyridin-2-yl (B'-11) cyclopropyl (B'-14) thiophen-3-yl (B'-15) 2-chlorophenyl (B'-16) 2-methoxyphenyl (B'-17) furan-3-yl (B'-18) 6-methoxybenzothiazol-2-yl (B'-19) thiophen-2-yl (B'-20) furan-2-yl (B'-21) 4-aminothiazol-2-yl;

b) the compounds corresponding to formula (I'-b) below:

(I'-b)

in which $X'_1$ is chosen from the groups of formulae ($X_1'$-1) to ($X_1'$-4) below:

($X_1'$-1) —CH₂—CH₂—

($X_1'$-2) —CH(CH₃)—CH₃ (isopropylidene)

($X_1'$-3) —CH₂—CH₂—CH₂—CH₂—

($X_1'$-4) —CH₂—CH₂—CH₂—CH₂—CH₂— c) the compounds corresponding to formula (I'-c) below:

(I'-c)

in which $X'_1$ is chosen from the groups of formulae ($X_1'$-8) to ($X_1'$-10) below:

($X_1'$-8) piperidine-1,4-diyl ($X_1'$-9) piperazine-1,4-diyl ($X_1'$-10) 1,2,3,6-tetrahydropyridine-1,4-diyl d) the compounds corresponding to formula (I'-d) below:
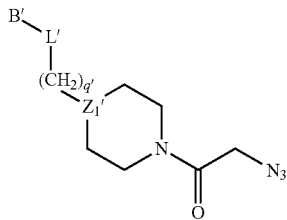
(I'-d)
in which:
the unit B' is a thiophenyl, phenyl, aminothiazolyl, benzothiazolyl or 2-pyridyl group,
L' is a heterocycle chosen from the rings of formulae (L'-1) to (L'-25) below:
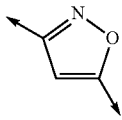
(L'-1)
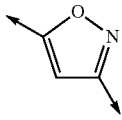
(L'-2)
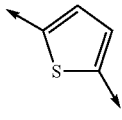
(L'-3)
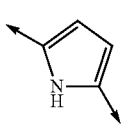
(L'-4)
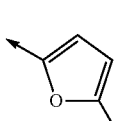
(L'-5)
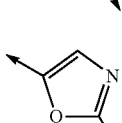
(L'-6)
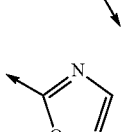
(L'-7)
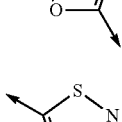
(L'-8)
-continued
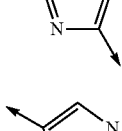
(L'-9)
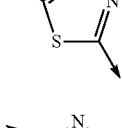
(L'-10)
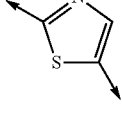
(L'-11)
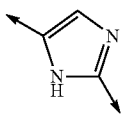
(L'-12)
(L'-13)
(L'-14)
(L'-15)
(L'-16)
(L'-17)
(L'-18)
(L'-19)
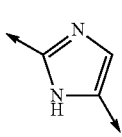
(L'-20)

-continued
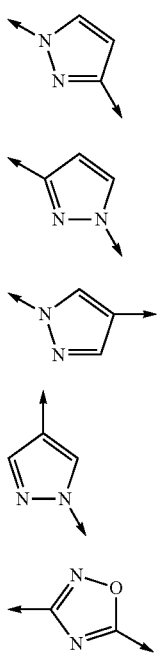
(L'-21)
(L'-22)
(L'-23)
(L'-24)
(L'-25)
q' is an integer equal to 0 or 1, and
$Z'_1$ represents a carbon or nitrogen atom, it being understood that when $Z'_1$ is a carbon atom, then q'=0;
e) the compounds corresponding to formula (I'-e) below:
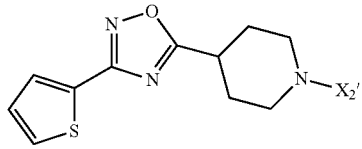
(I'-e)
in which $X_2'$ is chosen from the groups ($X_2'$-1) to ($X_2'$-23) below:
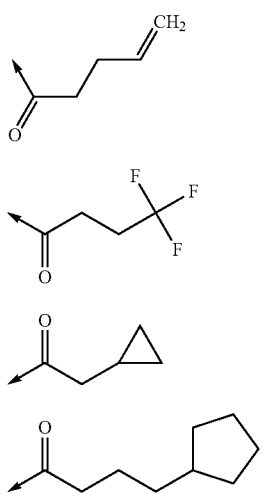
($X_2'$-1)
($X_2'$-2)
($X_2'$-3)
($X_2'$-4)
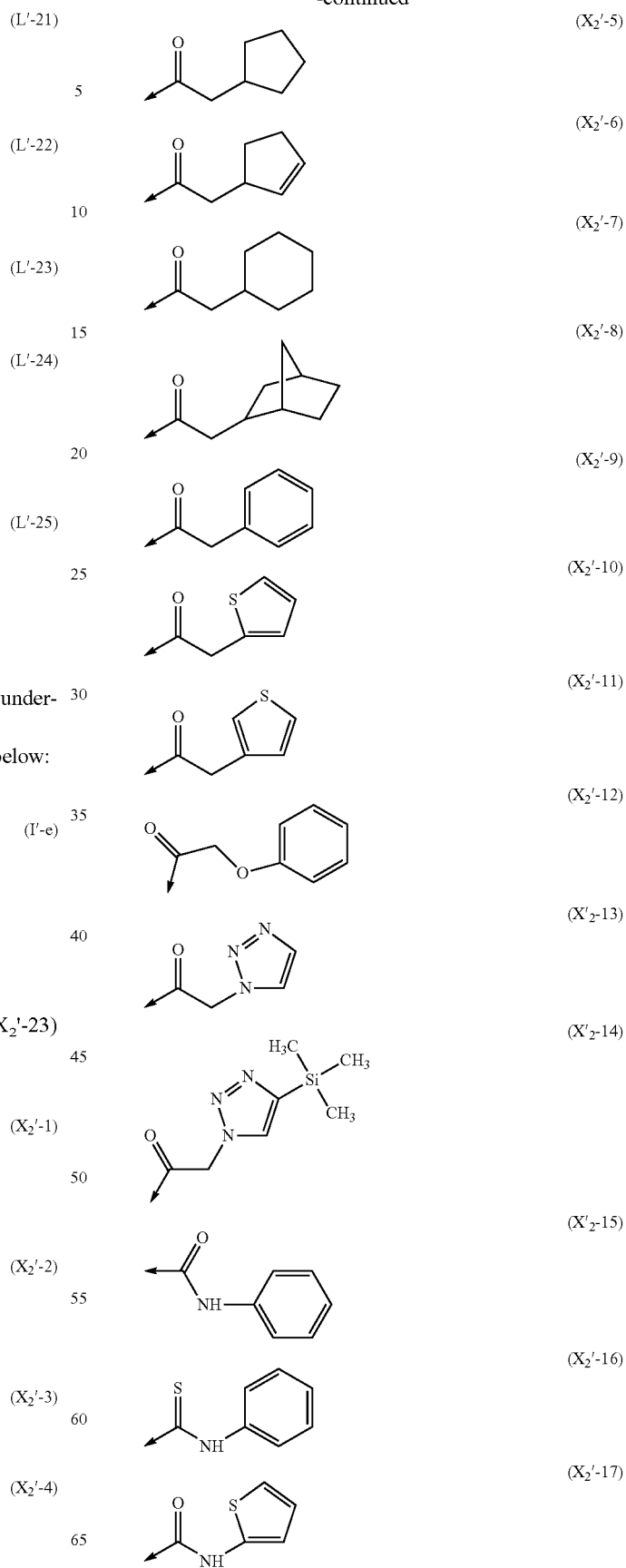
($X_2'$-5)
($X_2'$-6)
($X_2'$-7)
($X_2'$-8)
($X_2'$-9)
($X_2'$-10)
($X_2'$-11)
($X_2'$-12)
($X'_2$-13)
($X'_2$-14)
($X'_2$-15)
($X_2'$-16)
($X_2'$-17)

-continued

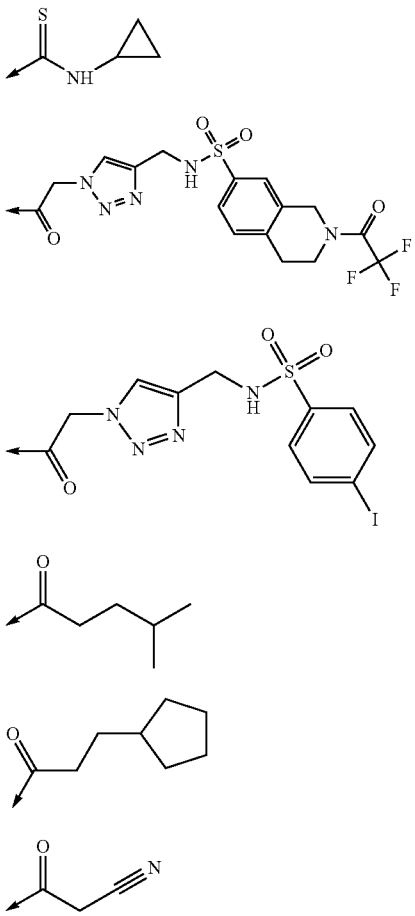

(X₂'-18)
(X₂'-19)
(X₂'-20)
(X'-21)
(X'-22)
(X'-23)

Among the compounds of formula (I'-d) hereinabove, those in which the unit B' represents a thiophenyl group are particularly preferred.

As compounds of formula (I') in accordance with the invention, mention may be made of:

2-azido-1-[4-(3-thiophen-2-yl[1,2,4]oxadiazol-5-yl)piperid-1-yl]ethanone (illustrated by formula (I-1) in Example 2 hereinbelow);
2-azido-1-[4-(3-cyclopropyl[1,2,4]oxadiazol-5-yl)piperid-1-yl]ethanone (compound 14);
2-azido-1-[4-(3-pyrid-2-yl[1,2,4]oxadiazol-5-yl)piperid-1-yl]ethanone (compound 13):
2-azido-1-{4-[3-(3-chloro-2-methylphenyl)[1,2,4]oxadiazol-5-yl]piperid-1-yl}-ethanone (compound 6);
2-azido-1-{4-[3-(2-fluoro-5-trifluoromethylphenyl)[1,2,4]oxadiazol-5-yl]piperid-1-yl}ethanone;
2-azido-1-{4-[3-(2,5-difluorophenyl)[1,2,4]oxadiazol-5-yl]piperid-1-yl}ethanone (compound 7);
2-azido-1-{4-[3-(2-methoxyphenyl)[1,2,4]oxadiazol-5-yl]piperid-1-yl}ethanone (compound 11);
2-azido-1-{4-[3-(2-chlorophenyl)[1,2,4]oxadiazol-5-yl]piperid-1-yl}ethanone (compound 10);
2-azido-1-[4-(3-phenyl[1,2,4]oxadiazol-5-yl)piperid-1-yl]ethanone (compound 4);
2-azido-1-{4-[3-(3-trifluoromethoxyphenyl)[1,2,4]oxadiazol-5-yl]piperid-1-yl}-ethanone;
2-azido-1-{4-[3-(4-tert-butyl phenyl)[1,2,4]oxadiazol-5-yl]piperid-1-yl}ethanone (compound 9);
2-azido-1-{4-[3-(4-trifluoromethylphenyl)[1,2,4]oxadiazol-5-yl]piperid-1-yl}-ethanone (compound 8);
2-azido-1-[4-(3-benzo[1,3]dioxol-5-yl[1,2,4]oxadiazol-5-yl)piperid-1-yl]ethanone (compound 12);
2-azido-1-[4-(3-furan-2-yl[1,2,4]oxadiazol-5-yl)piperid-1-yl]ethanone (compound 2);
2-azido-1-{4-[3-(4-fluorophenyl)[1,2,4]oxadiazol-5-yl]piperid-1-yl}ethanone (compound 5);
2-azido-1-[4-(3-thiophen-3-yl[1,2,4]oxadiazol-5-yl)piperid-1-yl]ethanone (compound 3);
2-azido-1-[4-(3-(6-methoxybenzothiazol-2-yl[1,2,4]oxadiazol-5-yl)piperid-1-yl]ethanone (compound 15);
1-[4-(3-thiophen-2-yl[1,2,4]oxadiazol-5-yl)piperid-1-yl]-2-[1,2,3]triazol-1-yl-ethanone (illustrated by formula (I-2) in Example 3 hereinbelow);
4-iodo-N-(1-{2-oxo-2-[4-(3-thiophen-2-yl[1,2,4]oxadiazol-5-yl)piperid-1-yl]-ethyl}-1H-1,2,3-triazol-4-ylmethyl) benzenesulfonamide (illustrated by formula (I-4) in Example 4 hereinbelow);
1-[4-(3-thiophen-2-yl[1,2,4]oxadiazol-5-yl)piperid-1-yl]-2-[1,2,3]triazol-1-yl-ethanone of formula (I-8) below:

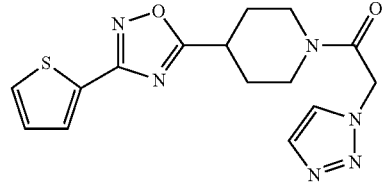

(I-8)

2-(2,2,2-trifluoroacetyl)-1,2,3,4-tetrahydroisoquinoline-7-sulfonic acid (1-{2-oxo-2-[4-(3-thiophen-2-yl[1,2,4]oxadiazol-5-yl)piperid-1-yl]ethyl}-1H-[1,2,3]-triazol-4-ylmethyl)amide of formula (I-9) below:

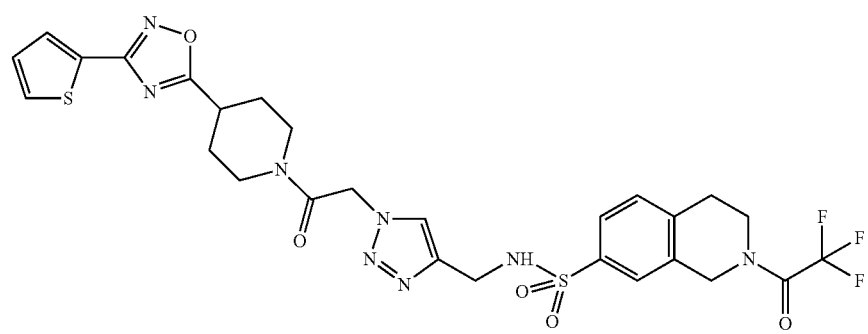

(I-9)

2-azido-1-[4-(3-thiophen-2-yl[1,2,4]oxadiazol-5-yl-methyl)piperazin-1-yl]-ethanone of formula (I-10) below:

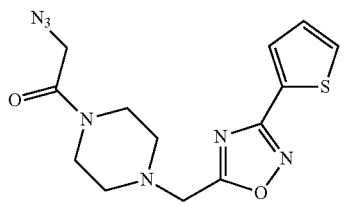

(I-10)

2-azido-1-[4-(5-thiophen-2-yl-4H-[1,2,4]triazol-3-yl)piperid-1-yl]ethanone of formula (I-14) below:

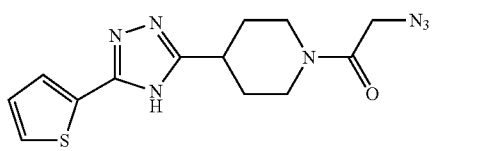

(I-14)

1-[4-(5-thiophen-2-yl-4H-[1,2,4]triazol-3-yl)piperid-1-yl]-2-[1,2,3]triazol-1-yl-ethanone of formula (I-15) below:

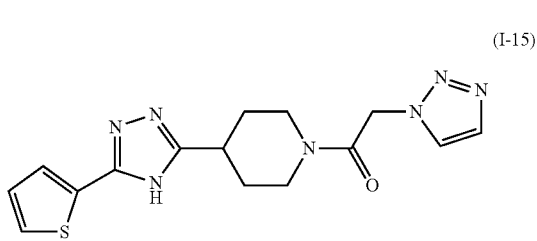

(I-15)

2-azido-1-[4-(3-thiophen-3-yl[1,2,4]oxadiazol-5-yl)piperid-1-yl]ethanone of formula (I-16) below:

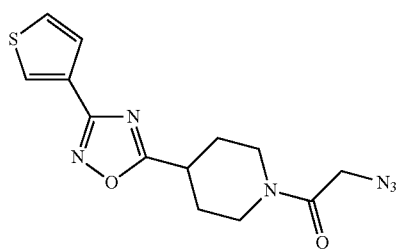

(I-16)

1-[4-(3-thiophen-3-yl[1,2,4]oxadiazol-5-yl)piperid-1-yl]-2-[1,2,3]triazol-1-yl-ethanone of formula (I-17) below:

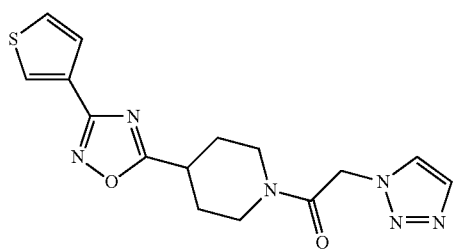

(I-17)

2-azido-1-[4-(3-furan-2-yl[1,2,4]oxadiazol-5-yl)piperid-1-yl]ethanone of to formula (I-18) below:

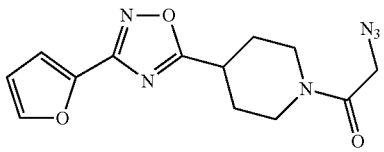

(I-18)

1-[4-(3-furan-2-yl[1,2,4]oxadiazol-5-yl)piperid-1-yl]-2-[1,2,3]triazol-1-ylethanone of formula (I-19) below:

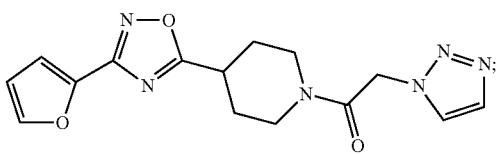

(I-19)

the allylic ester of 4-(3-thiophen-2-yl[1,2,4]oxadiazol-5-yl)piperidine-1-carboxylic acid;
2-phenoxy-1-[4-(3-thiophen-2-yl[1,2,4]oxadiazol-5-yl)piperid-1-yl]ethanone (Compound 45);
1-[4-(3-thiophen-2-yl[1,2,4]oxadiazol-5-yl)piperid-1-yl]propan-1-one (Compound 23);
3-cyclopentyl-1-[4-(3-thiophen-2-yl[1,2,4]oxadiazol-5-yl)piperid-1-yl]propan-1-one (Compound 34);
3,3-dimethyl-1-[4-(3-thiophen-2-yl[1,2,4]oxadiazol-5-yl)piperid-1-yl]butan-1-one (Compound 26);
2-thiophen-2-yl-1-[4-(3-thiophen-2-yl[1,2,4]oxadiazol-5-yl)piperid-1-yl]ethanone (Compound 43);
3-methyl-1-[4-(3-thiophen-2-yl[1,2,4]oxadiazol-5-yl)piperid-1-yl]butan-1-one (Compound 24);
4-methyl-1-[4-(3-thiophen-2-yl[1,2,4]oxadiazol-5-yl)piperid-1-yl]pentan-1-one (Compound 25);
2-bicyclo[2.2.1]hept-2-yl-1-[4-(3-thiophen-2-yl[1,2,4]oxadiazol-5-yl)piperid-1-yl]-ethanone (Compound 40);
2-cyclopropyl-1-[4-(3-thiophen-2-yl[1,2,4]oxadiazol-5-yl)piperid-1-yl]ethanone (Compound 33);
3-cyclohexyl-1-[4-(3-thiophen-2-yl[1,2,4]oxadiazol-5-yl)piperid-1-yl]propan-1-one (Compound 38);
2-phenyl-1-[4-(3-thiophen-2-yl[1,2,4]oxadiazol-5-yl)piperid-1-yl]ethanone (compound 41);
3-phenyl-1-[4-(3-thiophen-2-yl[1,2,4]oxadiazol-5-yl)piperid-1-yl]propan-1-one (Compound 42);
2-cyclohexyl-1-[4-(3-thiophen-2-yl[1,2,4]oxadiazol-5-yl)piperid-1-yl]ethanone (Compound 37);
2-cyclopent-2-enyl-1-[4-(3-thiophen-2-yl[1,2,4]oxadiazol-5-yl)piperid-1-yl]-ethanone (Compound 36);
2-(4-methylcyclohexyl)-1-[4-(3-thiophen-2-yl[1,2,4]oxadiazol-5-yl)piperid-1-yl]-ethanone (Compound 39);
3-tert-butoxy-1-[4-(3-thiophen-2-yl[1,2,4]oxadiazol-5-yl)piperid-1-yl]propan-1-one (compound 30);
2-cyclopentyl-1-[4-(3-thiophen-2-yl[1,2,4]oxadiazol-5-yl)piperid-1-yl]ethanone (Compound 35);
4,4,4-trifluoro-1-[4-(3-thiophen-2-yl[1,2,4]oxadiazol-5-yl)piperid-1-yl]butan-1-one (Compound 27);
1-[4-(3-thiophen-2-yl[1,2,4]oxadiazol-5-yl)piperid-1-yl]pent-4-en-1-one (Compound 20);
1-[4-(3-thiophen-2-yl[1,2,4]oxadiazol-5-yl)piperid-1-yl]pent-4-yn-1-one (Compound 21);
3-oxo-3-[4-(3-thiophen-2-yl[1,2,4]oxadiazol-5-yl)piperid-1-yl]propionitrile (Compound 22);

2-methoxy-1-[4-(3-thiophen-2-yl[1,2,4]oxadiazol-5-yl)piperid-1-yl]ethanone (Compound 28);
3-methoxy-1-[4-(3-thiophen-2-yl[1,2,4]oxadiazol-5-yl)piperid-1-yl]propan-1-one (Compound 29);
1-[4-(3-thiophen-2-yl[1,2,4]oxadiazol-5-yl)piperid-1-yl]ethanone (Compound 17);
4-oxo-4-[4-(3-thiophen-2-yl[1,2,4]oxadiazol-5-yl)piperid-1-yl]butyric acid (Compound 31);
5-oxo-5-[4-(3-thiophen-2-yl[1,2,4]oxadiazol-5-yl)piperid-1-yl]pentanoic acid (Compound 32);
1-phenylmethanesulfonyl-4-(3-thiophen-2-yl[1,2,4]oxadiazol-5-yl)piperidine (Compound 53);
1-(thiophene-3-sulfonyl)-4-(3-thiophen-2-yl[1,2,4]oxadiazol-5-yl)piperidine;
phenyl[4-(3-thiophen-2-yl[1,2,4]oxadiazol-5-yl)piperid-1-yl]methanone (Compound 54);
1-{4-[3-(5-bromothiophen-2-yl)[1,2,4]oxadiazol-5-yl]piperid-1-yl}-2-thiophen-2-ylethanone (compound 58);
3-{4-[3-(5-bromothiophen-2-yl)[1,2,4]oxadiazol-5-yl]piperid-1-yl}-3-oxo-propionitrile (compound 59);
2-thiophen-3-yl-1-[4-(3-thiophen-2-yl[1,2,4]triazol-5-yl)piperid-1-yl]ethanone (Compound 60);
2-(2-aminothiazol-4-yl)-1-[4-(3-thiophen-2-yl[1,2,4]oxadiazol-5-yl)piperid-1-yl]ethanone;
1-{4-[3-(2-aminothiazol-5-yl)[1,2,4]oxadiazol-5-yl]piperid-1-yl}-2-cyclopropyl-ethanone;
2-cyclopropyl-1-{4-[3-(3-dibenzylaminophenyl)[1,2,4]oxadiazol-5-yl]piperid-1-yl}ethanone;
2-(1H-tetrazol-5-yl)-1-[4-(3-thiophen-2-yl[1,2,4]oxadiazol-5-yl)piperid-1-yl]-ethanone;
2-(2-chlorophenyl)-1-[4-(3-thiophen-2-yl[1,2,4]oxadiazol-5-yl)piperid-1-yl]-ethanone;
2-(2,6-dichlorophenyl)-1-[4-(3-thiophen-2-yl[1,2,4]oxadiazol-5-yl)piperid-1-yl]-ethanone; and
2-pyrid-4-yl-1-[4-(3-thiophen-2-yl[1,2,4]oxadiazol-5-yl)piperid-1-yl]ethanone.

The compounds of formula (I') in accordance with the invention may be readily prepared, generally in two, three or four steps, according to synthetic processes similar to the standard processes that are well known to those skilled in the art.

Thus, the compounds of formula (I') in which the unit A' represents a group of formula (II') in which n'=0, $X_1'$ represents piperidine and $X_2'$ represents a group of formula (III'a) in which $X_3'$ represents an oxygen atom, Y' represents a group -(T')$_{p'}$-(CH$_2$)$_{m'}$—R'$_1$ in which, p'=0, m'=1 and R'$_1$ represents an azido group and in which the group L' represents an oxadiazole ring and the unit B' is as defined previously, may be prepared, for example, according to the process represented in reaction scheme A hereinbelow:

SCHEME A

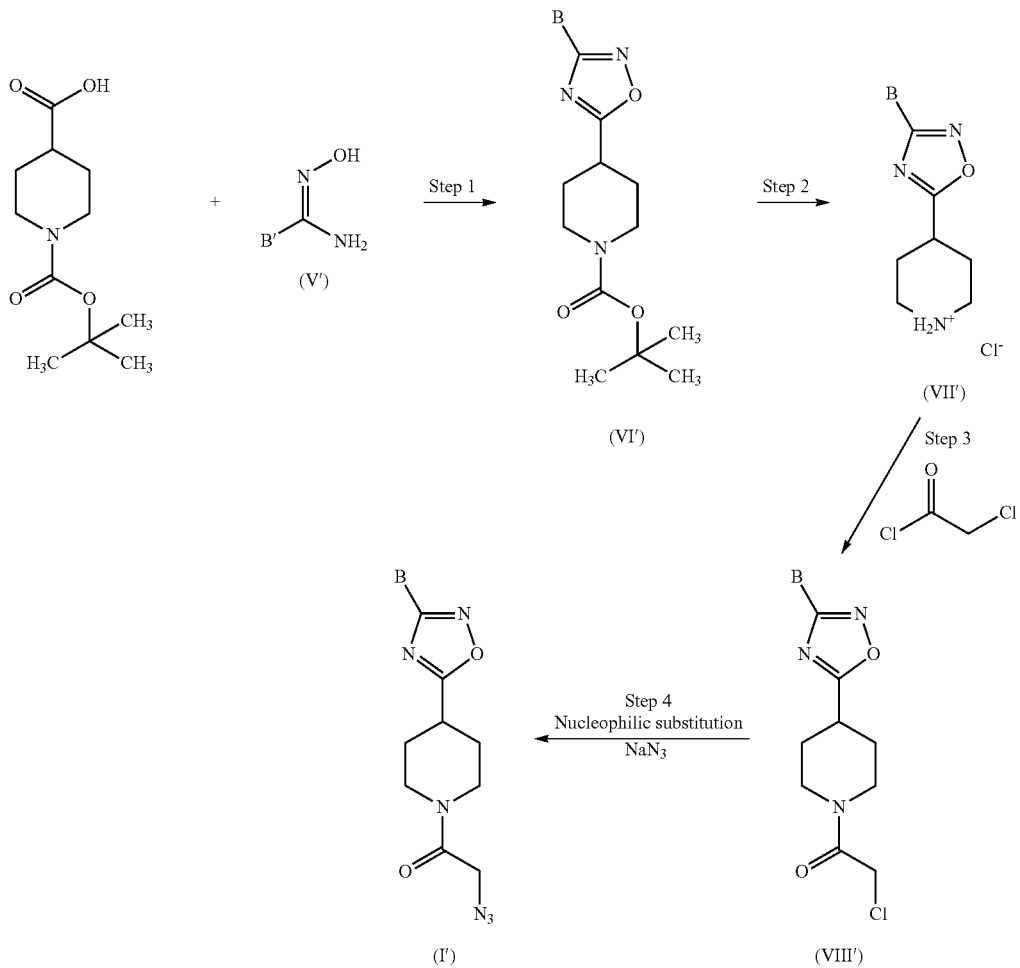

according to which, in a first step, the mono-tert-butylpiperidine-1,4-carboxylic acid ester is reacted, in solution in an organic solvent, with a compound of formula (V') in which B' has the same meaning as that given previously, in the presence of O-benzotriazole-1-yl-N,N,N',N'-tetramethyluronium tetrafluoro-borate and hydroxybenzotriazole hydrate, to give a compound of formula (VI'), which, in a second step, is deprotected in the presence of hydrochloric acid to give the compounds of formula (VII'), which, in a third step, is reacted, in an organic solvent in the presence of chloroacetyl chloride and triethylamine, and is finally subjected, in a fourth step, to a nucleophilic substitution in the presence of sodium azide, to give the expected compound of formula (I') (Poulain R. F. et al., Tetrahedron Letters, 2001, 42, 1495-1498 and Evans M. D. et al., Tetrahedron Letters, 2003, 44, 9337-9341).

According to the process shown in Scheme A, the first step is preferably performed at a temperature of between 100 and 120° C. and the organic solvent is preferably dimethylformamide. The time required perform the first step is generally between 6 and 18 hours. The second step is preferably performed at room temperature using ethanol as reaction solvent. The time required to perform the second step is generally between 3 and 6 hours.

The compounds of formula (I') in which the unit A' represents a group of formula (II') in which n'=1, $X'_1$ represents one of the groups of formulae $(X_1'-1)$ to $(X_1'-4)$ and $X_2'$ represents a group of formula (III'a) in which $X_3'$ is an oxygen atom, Y' represents a group $-(T')_{p'}-(CH_2)_{m'}-R'_1$ in which p'=0, m'=1 and $R'_1$ represents an azido group and in which the group L' represents an oxadiazole ring and the unit B' is as defined previously, may be prepared, for example, according to the process shown in reaction scheme B hereinbelow:

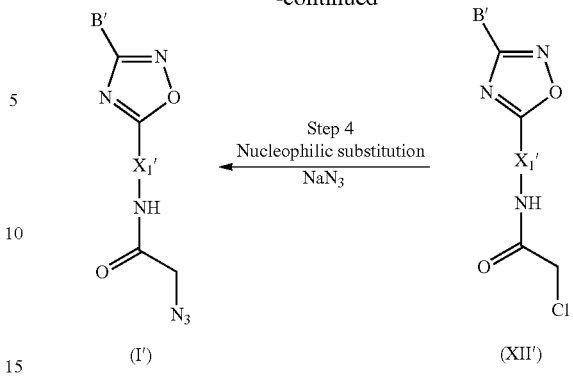

according to which steps 1 to 4 are performed as described previously for steps 1 to 4 of the process shown in scheme A hereinabove, using as starting material a compound of formula (IX') above in which $X_1'$ is chosen from the groups $(X_1'-1)$ to $(X_1'-4)$ as described previously.

The compounds of formula (I') in which the unit A' represents a group of formula (II') for which n'=0, $X_1'$ represents piperidine and $X_2'$ represents a group of formula (III'a) in which $X_3'$ represents an oxygen atom, Y' represents a group $-(T')_{p'}-(CH_2)_{m'}-R_1'$ in which p'=0, m'=1 and $R_1'$ represents a triazole group substituted with a trimethylsilyl group or a group chosen from the compounds of formula (IV') described above and in which the group L' represents an oxadiazole ring and the unit B' is as defined previously, may be prepared, for example, according to the process shown in reaction scheme C hereinbelow:

SCHEME B

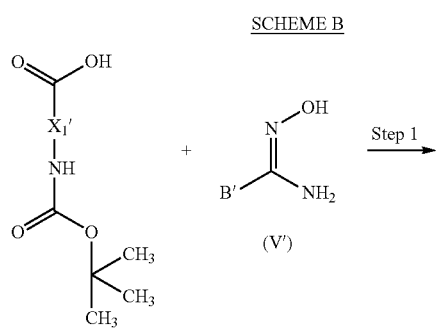

SCHEME C

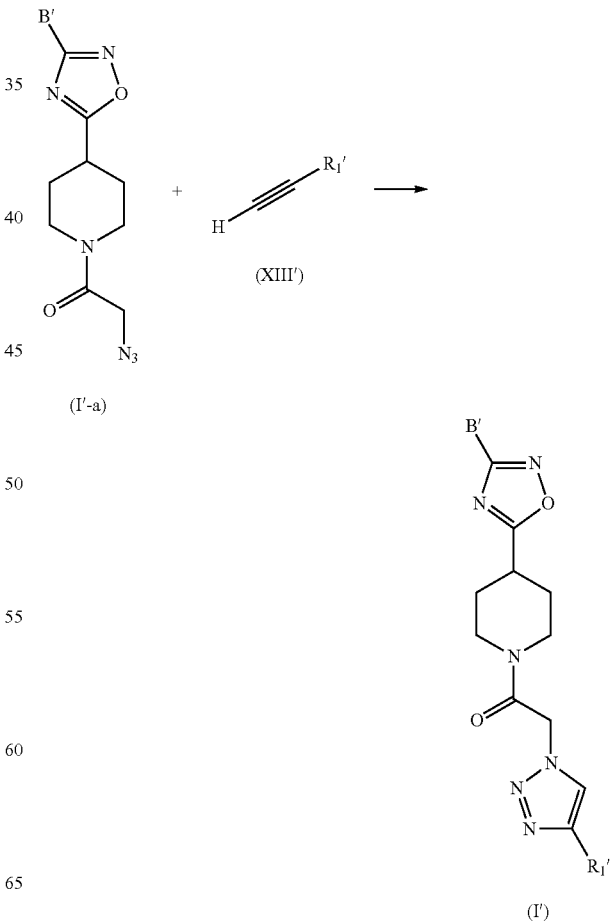

according to which the compounds of formula (I'-a), in which B' has the same meaning as that indicated previously, are reacted, in solution in acetonitrile, in the presence of a compound of formula (XIII') in which $R_1$' has the same meaning as that indicated previously, in the presence of copper iodide, to obtain the expected compound of formula (I') (Krasinski, A. et al., J. Am. Chem. Soc., 2005; 127(18), 6686-6692).

The compounds of formula (I') in which the unit A' represents a group of formula (II') for which n'=0, $X_1$' represents piperidine and $X_2$' represents a group of formula (III'a) in which $X_3$' represents an oxygen atom, Y' represents a group $-(T')_{p'}-(CH_2)_{m'}-R_1'$ in which p'=0, m'=1 and $R_1$' represents a triazole group and in which the group L' represents an oxadiazole ring and the unit B' is as defined previously, may be prepared, for example, according to the process shown in reaction scheme D hereinbelow:

SCHEME D

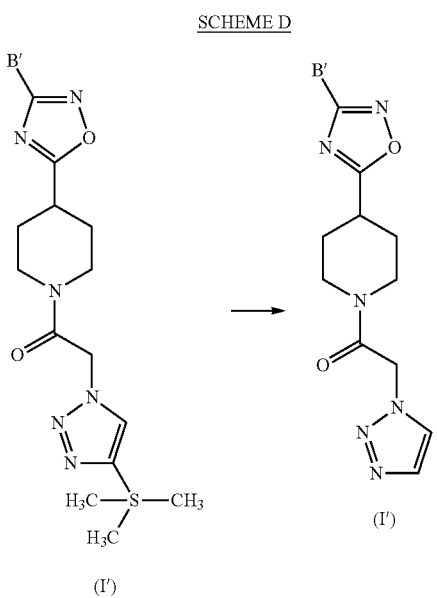

(I') (I')

according to which the particular compounds of formula (I') above, in which B' has the same meaning as that indicated previously, are reacted, in solution in tetrahydrofuran, in the presence of tetrabutylammonium fluoride, to obtain the expected compound of formula (I').

When the synthesis is complete, the compounds of formula (I') may, if necessary, be purified according to the methods that are well known to those skilled in the art.

Another subject of the present invention is also a pharmaceutical composition comprising, as active principle, at least one compound of formula (I') as defined previously and at least one pharmaceutically acceptable excipient.

BRIEF DESCRIPTION OF THE DRAWINGS

Besides the preceding provisions, the invention also comprises other provisions that will emerge from the description that follows, which refers to examples of synthesis of compounds of formula (I), to an example of demonstration of the potentiating effect on ETH activity by a compound of formula (I), and also to the attached figures, in which FIG. 1 is a photograph of three Petri dishes after inoculating and culturing *M tuberculosis* mycobacteria on agar gel as a function of the presence or absence of a dose of ETH (2 or 4 μg) optionally combined with 20 nmol of compound of formula (I-3); and.

FIG. 2 is a graph showing the ethionamide-potentiating effect of compound (I-1) evaluated according to the RIA detection method in liquid medium on the Bactec® 460 robot in 12 B medium, in which the growth index (arbitrary units) is presented as a function of the time in days.

EXAMPLES

It should be clearly understood that these examples are given purely as illustrations of the subject of the invention, of which they do not in any way constitute a limitation.

Example 1

Synthesis of the t-butyl ester of 4-(3-thiophen-2-yl-1,2,4-oxadiazol-5-yl)piperidine-1-carboxylic acid (Compound of formula (I-3))

(I-3)

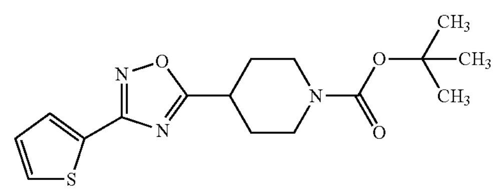

1) First Step: Synthesis of N-hydroxythiophene-2-carboxamidine

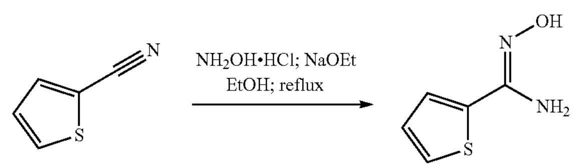

A solution of sodium ethoxide (21% by weight in ethanol, 64.9 ml, 0.174 mol, 1.1 eq.), hydroxylamine hydrochloride (12.1 g, 0.174 mol, 1.1 eq.) and ethanol (100 ml) was refluxed for 30 minutes. Thiophene-2-carbonitrile (18.8 g; 0.172 mol; 1 eq.) was then added and the solution was refluxed continuously for 18 hours. The reaction was monitored by thin layer chromatography (TLC) (50/50 cyclohexane/pentane). The solution was evaporated under reduced pressure and the residue obtained triturated in water at pH 7. The aqueous phase, saturated beforehand with NaCl, was then extracted with ethyl ether (three times). The organic phases were combined, dried over $MgSO_4$ and concentrated under reduced pressure to give a white powder.

Proton NMR (DMSO-d6, δ): 9.60 (s, 1H), 7.36 (dd, J=4.8 Hz, J=0.9 Hz, 1H), 7.40 (dd, J=3.6 Hz, J=0.9 Hz, 1H), 7.03 (dd, J=4.8 Hz, J=3.6 Hz, 1H), 5.93 (brs, 2H).

MS m/z: 143 ($M^+$+1).

Figure 1:
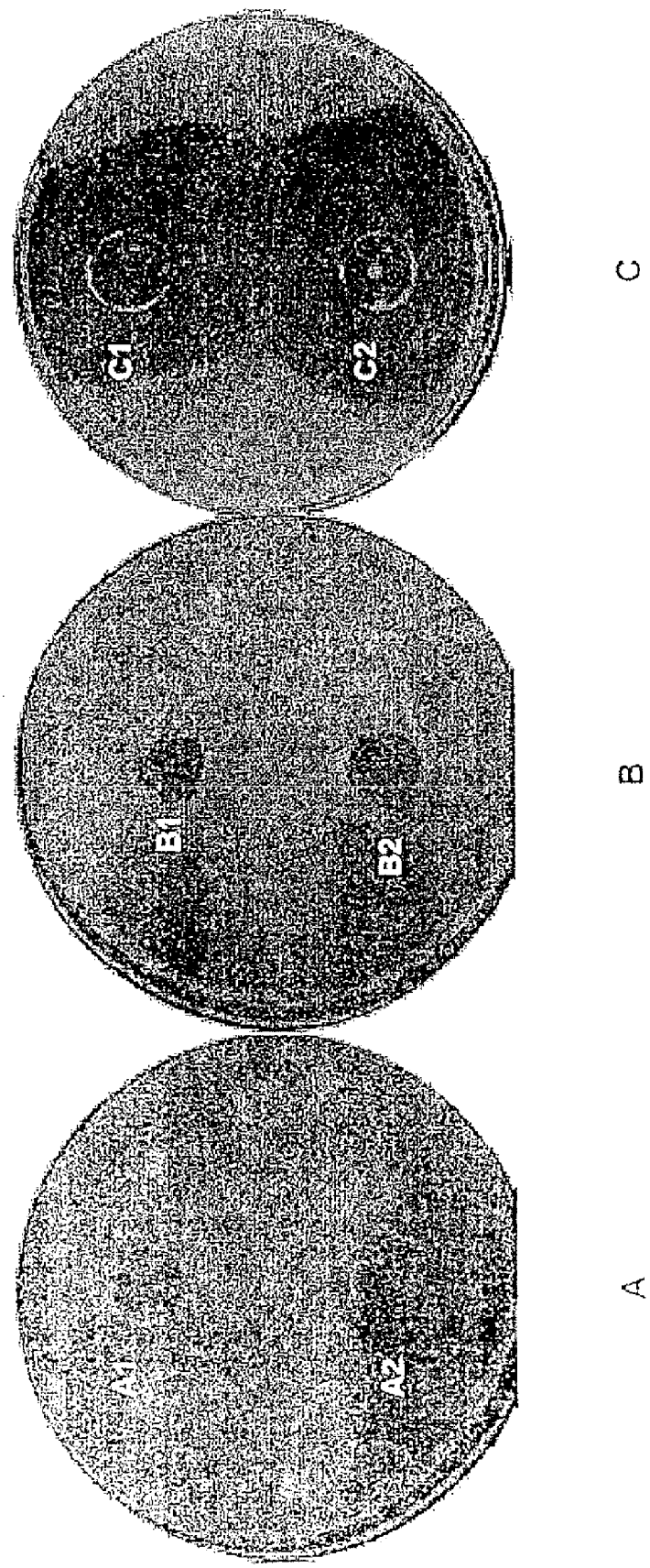

2) Second Step: Synthesis of the t-butyl ester of 4-(3-thiophen-2-yl-1,2,4-oxadiazol-5-yl)piperidine-1-carboxylic acid of formula (I-3)

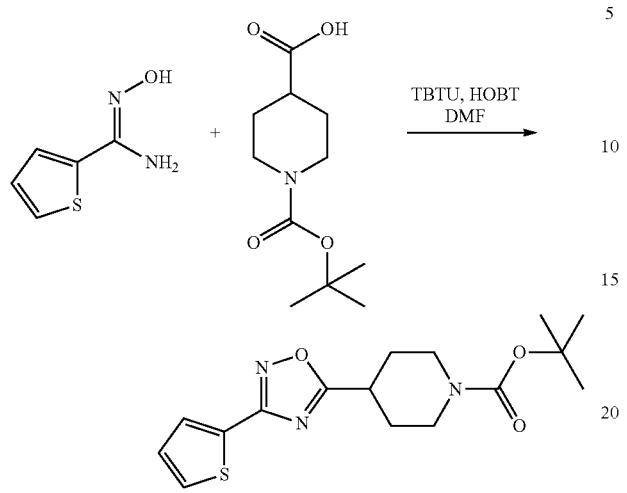

2.293 g (1 eq.) of the mono-tert-butyl ester of piperidine-1,4-dicarboxylic acid, 3.210 g (1 eq.) of O-benzotriazol-1-yl-N,N,N'N'-tetramethyluronium tetrafluoroborate (TBTU), 306.2 mg (0.2 eq.) of 1-hydroxybenzotriazole hydrate (HOBT) and 8.56 ml (5 eq.) of ethyldiisopropyl-amine were added to 50 ml of dimethylformamide (DMF) in a sealed tube, and stirred for 1 minute. 1.422 g (1 eq.) of N-hydroxythiophene-2-carboxamidine were then added to the suspension. The resulting mixture was stirred at room temperature for 1 hour and then at 110° C. for 6 hours. The DMF was then evaporated off, and the residue was purified on silica gel (90/10 cyclohexane/ethyl acetate). The compound of formula (I-3) was obtained in the form of a white solid, in a yield of 40%.

Proton NMR (DMSO-d6, δ): 7.85 (dd, J=5.0 Hz, J=1.1 Hz, 1H), 7.77 (dd, J=3.8 Hz, J=1.1 Hz), 7.25 (dd, J=5.0 Hz, J=3.8 Hz, 1H), 3.90 (d, J=13.3 Hz, 2H), 3.26 (m, 1H), 2.10 (dd, J=13.3 Hz, J=3.0 Hz, 2H), 1.65 (m, 2H), 1.35 (s, 9H)

MS m/z: 358 (M$^+$+Na)

The following compounds were synthesized according to the same protocol as that described above for the compound of formula (I-3):

t-Butyl ester of 4-(3-cyclopropyl[1,2,4-]oxadiazol-5-yl)piperidine-1-carboxylic acid

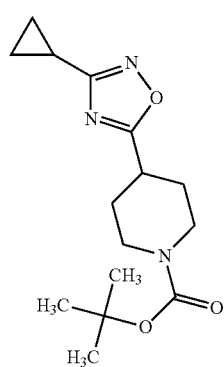

MS m/z: 294 (M$^+$+1) and 238 (M$^+$-55)

t-Butyl ester of 4-(3-pyrid-2-yl[1,2,4]oxadiazol-5-yl)piperidine-1-carboxylic acid

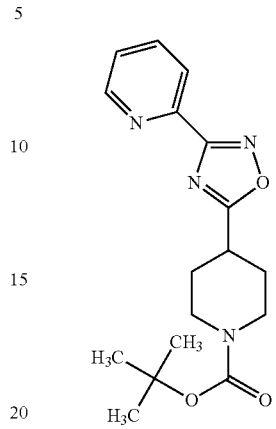

MS m/z: 331 (M$^+$+1)

$^1$H NMR (CDCl$_3$): δ 8.82 (dd, J=4.9 Hz J=1.2 Hz, 1H), 8.14 (dd, J=7.8 Hz J=1.8 Hz, 1H), 7.88 (td, J=7.8 Hz J=7.8 Hz J=1.8 Hz, 1H), 7.46 (ddd, J=7.8 Hz J=4.9 Hz J=1.2 Hz, 1H), 4.14 (m, 2H), 3.21 (m, 1H), 2.98 (m, 2H), 2.15 (m, 2H), 1.93 (m, 2H), 1.47 (s, 9H).

t-Butyl ester of 4-[3-(3-chloro-2-methylphenyl)[1,2,4]oxadiazol-5-yl]piperidine-1-carboxylic acid

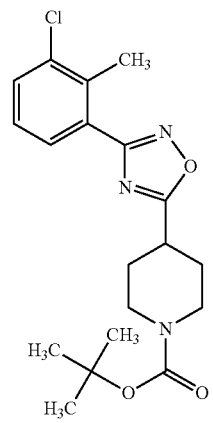

MS m/z: 378 (M$^+$+1) and 322 (M$^+$-55)

$^1$H NMR (CDCl$_3$): δ 7.77 (dd, J=7.9 Hz J=1.1 Hz, 1H), 7.50 (dd, J=7.5 Hz J=1.1 Hz, 1H), 7.22 (t, J=7.9 Hz, 1H), 4.12 (m, 2H), 3.18 (m, 1H), 3.00 (m, 2H), 2.63 (s, 3H), 2.13 (m, 2H), 1.88 (m, 2H), 1.47 (s, 9H)

$^{13}$C NMR (CDCl$_3$): δ 184.89, 180.66, 168.55, 154.64, 136.09, 131.51, 128.81, 128.27, 126.76, 79.92, 34.41, 29.15, 28.43, 18.10.

t-Butyl ester of 4-(3-pyrid-3-yl[1,2,4]oxadiazol-5-yl)piperidine-1-carboxylic acid

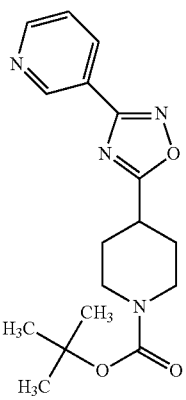

MS m/z: 331 (M⁺+1) and 231 (M⁺−99)

t-Butyl ester of 4-[3-(2-fluoro-5-trifluoromethylphenyl)[1,2,4]oxadiazol-5-yl]piperidine-1-carboxylic acid

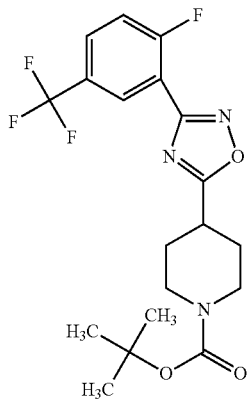

MS m/z: 416 (M⁺+1) and 360 (M⁺−55)
$^1$H NMR (CDCl$_3$): δ 8.37 (dd, J=6.3 Hz J=2.3 Hz, 1H), 7.78 (m, 1H), 7.37 (t, J=9.2 Hz, 1H), 4.14 (m, 2H), 3.21 (m, 1H), 3.00 (m, 2H), 2.17 (m, 2H), 1.91 (m, 2H), 1.48 (s, 9H).
$^{13}$C NMR (CDCl$_3$): δ 182.47, 165.08, 162.32, 161.58, 155.61, 130.86, 129.50, 118.72, 80.94, 35.48, 30.14, 29.43.

t-Butyl ester of 4-[3-(2,5-difluorophenyl)[1,2,4]oxadiazol-5-yl]piperidine-1-carboxylic acid

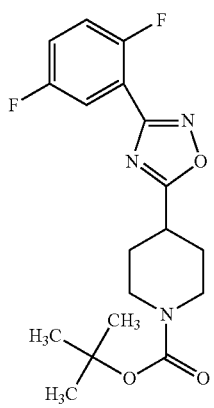

MS m/z: 366 (M⁺+1) and 310 (M⁺−55)
$^1$H NMR (CDCl$_3$): δ 7.69 (m, 1H), 7.13 (m, 2H), 4.07 (m, 2H), 3.12 (m, 1H), 2.92 (m, 2H), 2.06 (m, 2H), 1.88 (m, 2H), 1.41 (s, 9H).

t-Butyl ester of 4-[3-(2-methoxyphenyl)[1,2,4]oxadiazol-5-yl]piperidine-1-carboxylic acid

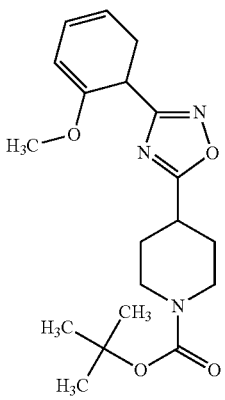

MS m/z: 360 (M⁺+1) and 304 (M⁺−55)
$^1$H NMR (DMSO): δ7.80 (dd, J=7.5 Hz J=1.8 Hz, 1H), 7.53 (td, J=7.5 Hz J=7.5 Hz J=1.8 Hz, 1H), 7.20 (dd, J=7.5 Hz J=1.0 Hz, 1H), 7.08 (td, J=7.5 Hz J=7.5 Hz J=1.0 Hz, 1H), 3.92 (m, 2H), 3.84 (s, 3H), 2.95 (m, 2H), 2.04 (m, 2H), 1.62 (m, 2H), 1.39 (s, 9H).

t-Butyl ester of 4-[3-(2-chlorophenyl)[1,2,4]oxadiazol-5-yl]piperidine-1-carboxylic acid

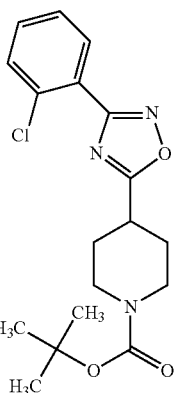

MS m/z: 364 (M⁺+1) and 308 (M⁺−55)

t-Butyl ester of 4-(3-phenyl)[1,2,4]oxadiazol-5-yl]piperidine-1-carboxylic acid

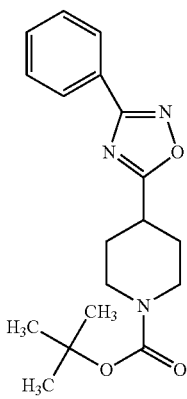

MS m/z: 330 (M$^+$+1) and (M$^+$−55)

$^1$H NMR (CDCl$_3$): δ 8.07 (m, 2H), 7.48 (m, 3H), 6.82 (d, J=8.3 Hz, 1H), 4.13 (m, 2H), 3.16 (m, 1H), 3.00 (m, 2H), 2.12 (m, 2H), 1.90 (m, 2H), 1.48 (s, 9H).

$^{13}$C NMR (CDCl$_3$): δ 182.29, 169.24, 155.61, 132.15, 129.83, 128.40, 125.00, 80.82, 39.17, 30.17, 29.41.

t-Butyl ester of 4-[3-(3-trifluoromethoxyphenyl)[1,2,4]oxadiazol-5-yl]-piperidine-1-carboxylic acid

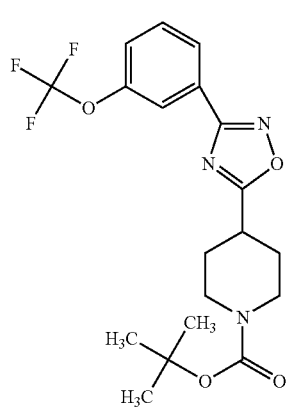

MS m/z: 414 (M$^+$+1) and 358 (M$^+$−55)

$^1$H NMR (CDCl$_3$): δ 7.95 (d, J=8.0 Hz, 1H), 7.87 (s, 1H), 7.45 (t, J=8.0 Hz, 1H), 7.28 (d, J=8.0 Hz, 1H), 4.06 (m, 2H), 3.10 (m, 1H), 2.92 (m, 2H), 2.05 (m, 2H), 1.82 (m, 2H), 0.92 (s, 9H).

t-Butyl ester of 4-[3-(4-tert-butylphenyl)[1,2,4]oxadiazol-5-yl]piperidine-1-carboxylic acid

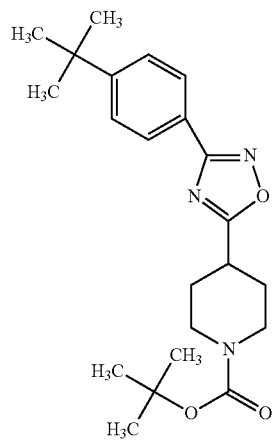

MS m/z: 386 (M$^+$+1) and 330 (M$^+$−55)

$^1$H NMR (CDCl$_3$): δ 7.95 (d, J=8.0 Hz, 1H), 7.87 (s, 1H), 7.45 (t, J=8.0 Hz, 1H), 7.28 (d, J=8.0 Hz, 1H), 4.06 (m, 2H), 3.10 (m, 1H), 2.92 (m, 2H), 2.05 (m, 2H), 1.82 (m, 2H), 0.92 (s, 9H).

t-Butyl ester of 4-[3-(4-trifluoromethylphenyl)[1,2,4]oxadiazol-5-yl]piperidine-1-carboxylic acid MS m/z: 398 (M$^+$+1) and 342 (M$^+$−55)

$^1$H NMR (CDCl$_3$): δ 8.21 (d, J=8.0 Hz, 2H), 7.74 (d, J=8.0 Hz, 2H), 4.14 (m, 2H), 3.18 (m, 1H), 3.01 (m, 2H), 2.13 (m, 2H), 1.90 (m, 2H), 1.47 (s, 9H).

$^{13}$C NMR (CDCl$_3$): δ 182.87, 168.30, 155.63, 131.24, 128.80, 126.89, 80.93, 35.55, 30.14, 29.44.

47 t-Butyl ester of 4-(3-benzo[1,3]-dioxol-5-yl[1,2,4]oxadiazol-5-yl)piperidine-1-carboxylic acid

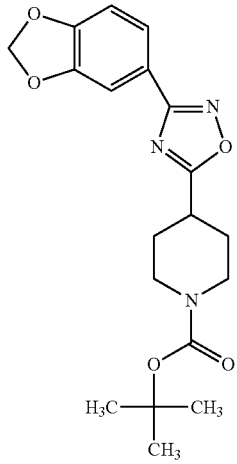

MS m/z: 374 (M⁺+1) and 318 (M⁺−55)

¹H NMR (CDCl₃): δ 7.56 (dd, J=8.3 Hz J=1.5 Hz, 1H), 7.44 (d, J=1.5 Hz, 1H), 6.82 (d, J=8.3 Hz, 1H), 5.97 (s, 2H), 4.05 (m, 2H), 3.07 (m, 1H), 2.91 (m, 2H), 2.05 (m, 2H), 1.83 (m, 2H), 1.40 (s, 9H).

¹³C NMR (CDCl₃): δ 182.07, 155.63, 151.10, 124.91, 123.33, 121.66, 109.70, 109.64, 108.45, 102.59, 80.77, 35.48, 30.13, 29.43.

t-Butyl ester of 4-(3-furan-2-yl[1,2,4]oxadiazol-5-yl)piperidine-1-carboxylic acid

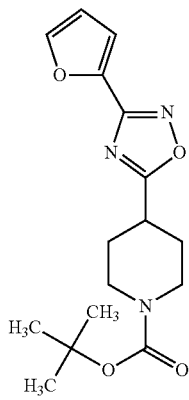

¹H NMR: δ=7.62 (dd, J=1.68 Hz, J=0.72 Hz, 1H), 7.14 (dd, J=3.48 Hz, J=0.72 Hz, 1H), 6.57 (dd, J=3.48 Hz, J=1.77 Hz, 1H), 4.14 (m, 2H), 3.15 (m, 1H), 2.94 (m, 2H), 2.11 (m, 2H), 1.86 (m, 2H), 1.49 (s, 9H).

MS m/z: 320 (M⁺+1)

48 t-Butyl ester of 4-[3-(4-fluorophenyl)[1,2,4]oxadiazol-5-yl)piperidine-1-carboxylic acid

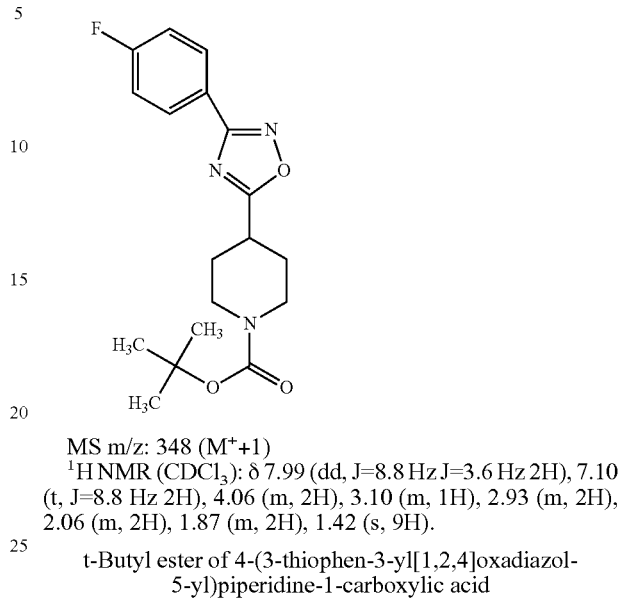

MS m/z: 348 (M⁺+1)

¹H NMR (CDCl₃): δ 7.99 (dd, J=8.8 Hz J=3.6 Hz 2H), 7.10 (t, J=8.8 Hz 2H), 4.06 (m, 2H), 3.10 (m, 1H), 2.93 (m, 2H), 2.06 (m, 2H), 1.87 (m, 2H), 1.42 (s, 9H).

t-Butyl ester of 4-(3-thiophen-3-yl[1,2,4]oxadiazol-5-yl)piperidine-1-carboxylic acid

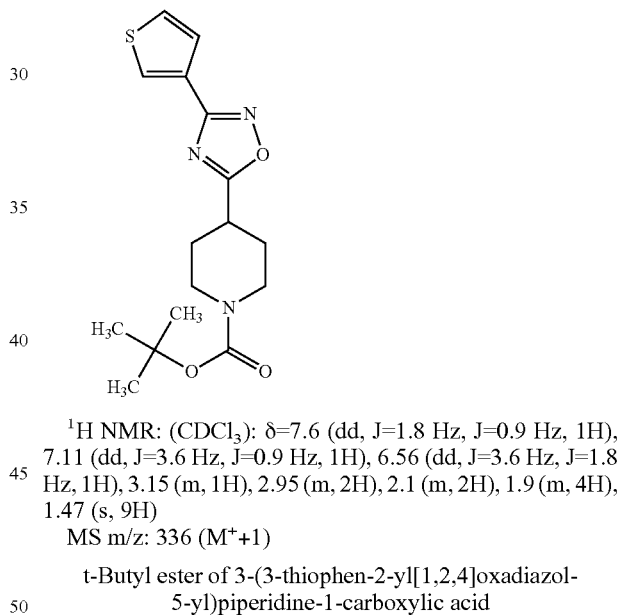

¹H NMR: (CDCl₃): δ=7.6 (dd, J=1.8 Hz, J=0.9 Hz, 1H), 7.11 (dd, J=3.6 Hz, J=0.9 Hz, 1H), 6.56 (dd, J=3.6 Hz, J=1.8 Hz, 1H), 3.15 (m, 1H), 2.95 (m, 2H), 2.1 (m, 2H), 1.9 (m, 4H), 1.47 (s, 9H)

MS m/z: 336 (M⁺+1)

t-Butyl ester of 3-(3-thiophen-2-yl[1,2,4]oxadiazol-5-yl)piperidine-1-carboxylic acid

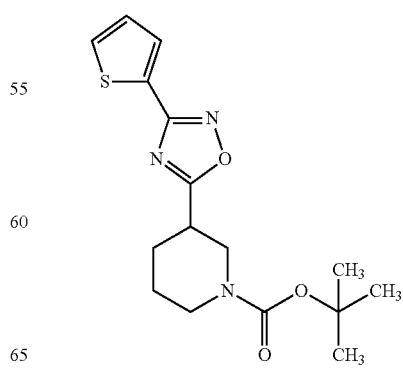

Proton NMR (CDCl$_3$, δ): 7.80 (dd, J=3.6 Hz, J=2.7 Hz, 1H), 7.51 (m, 1H), 7.20 (t, J=3.6 Hz, 1H), 3.98 (d, J=13.2 Hz, 1H); 3.02 (m, 1H), 2.26 (d, J=4.8 Hz, 1H), 1.48 (s, 9H)

MS m/z: 336 (M$^+$+1)

t-Butyl ester of 2-(3-thiophen-2-yl[1,2,4]oxadiazol-5-yl)pyrrolidine-1-carboxylic acid

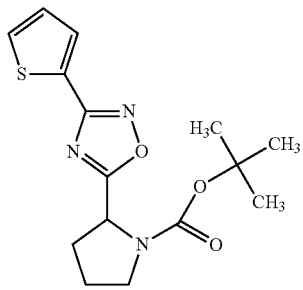

Proton NMR (CDCl$_3$, δ): 7.80 (m, 1H), 7.51 (m, 1H), 7.20 (m, 1H), 3.63 (m, 1H), 3.44 (m, 1H), 2.33 (m, 2.26 (m, 1H), 1.48 (s, 9H)

MS m/z: 322 (M$^+$+1)

t-Butyl ester of [2-(3-thiophen-2-yl[1,2,4]oxadiazol-5-yl)ethyl]carbamic acid

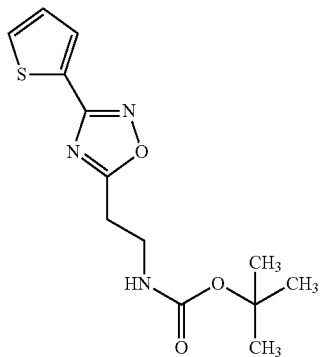

Proton NMR (CDCl$_3$, δ): 7.72 (dd, J=3.6 Hz, J=2.7 Hz, 1H), 7.44 (dd, J=3.6 Hz, J=2.7 Hz, 1H); 7.09 (t, J=3.9 Hz, 1H); 4.99 (brs, 1H, NH); 3.59 (t, J=6 Hz, 2H); 3.06 (t, J=6 Hz, 2H); 1.37 (s, 9H)

MS m/z: 196 (M$^+$−99)

t-Butyl ester of [3-(3-thiophen-2-yl[1,2,4]oxadiazol-5-yl)propyl]carbamic acid

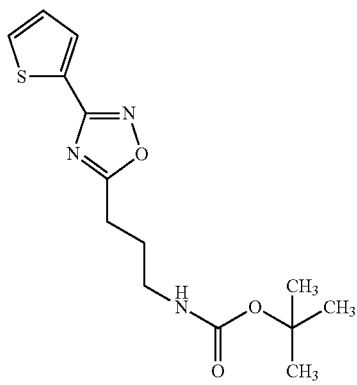

Proton NMR (CDCl$_3$, δ): 7.70 (dd, J=3.6 Hz, J=2.7 Hz, 1H), 7.43 (dd, J=5.1 Hz, J=1.2 Hz, 1H), 7.08 (t, J=5.1 Hz, 1H), 4.67 (brs, 1H), 3.21 (t, J=6.6 Hz, 2H), 2.92 (t, J=7.2 Hz, 2H), 2.00 (m, 2H), 1.37 (s, 9H)

MS m/z: 210 (M$^+$−99)

t-Butyl ester of [4-(3-thiophen-2-yl[1,2,4]oxadiazol-5-yl)butyl]carbamic acid

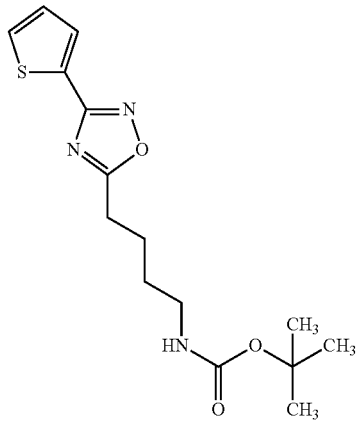

Proton NMR (DMSO-d6, δ): 7.70 (m, 1H); 7.43 (m, 1H); 7.08 (m, 1H); 4.53 (brs, 1H, NH); 3.11 (m, 2H); 2.09 (m, 2H); 1.79 (m, 2H); 1.56 (m, 2H); 1.35 (s, 9H).

MS m/z: 224 (M$^+$−99)

t-Butyl ester of [5-(3-thiophen-2-yl[1,2,4]oxadiazol-5-yl)pentyl]carbamic acid

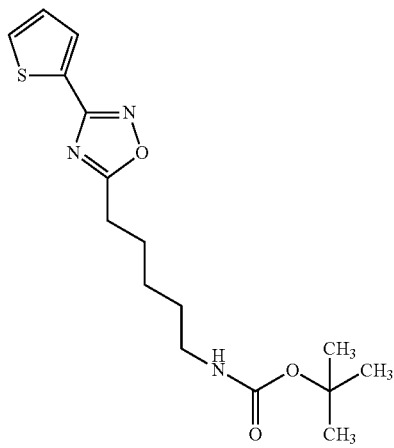

Proton NMR (DMSO-d6, δ): 7.42 (m, 1H); 7.08 (m, 1H); 4.48 (brs, 1H, NH); 3.06 (m, 2H); 2.89 (m, 2H); 1.82 (m, 2H); 1.48 (m, 4H); 1.36 (s, 9H).

MS m/z: 238 (M$^+$-99)

t-Butyl ester of 4-[3-(6-methoxybenzothiazol-2-yl)[1,2,4]oxadiazol-5-yl]piperidine-1-carboxylic acid

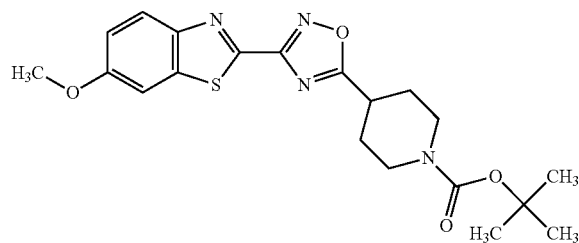

MS: m/z 417 (M+H⁺)

$^1$H NMR (CDCl$_3$): δ 8.11 (d, J=8.8 Hz, 1H), 7.37 (s, 1H), δ 7.15 (d, J=8.8 Hz, 1H), 4.15 (m, 2H), 3.90 (s, 3H), 3.23 (m, 1H), 2.97 (m, 2H), 2.14 (m, 2H), 1.96 (m, 2H), 1.47 (s, 9H).

$^{13}$C NMR (CDCl$_3$): δ 182.62, 164.49, 159.17, 154.59, 148.07, 145.28, 137.14, 125.36, 117.03, 103.64, 79.94, 55.86, 42.96, 34.72, 29.08, 28.43.

Example 2

Synthesis of 2-azido-1-[4-(3-thiophen-2-yl[1,2,4]oxadiazol-5-yl)piperid-1-yl]ethanone (compound (I-1))

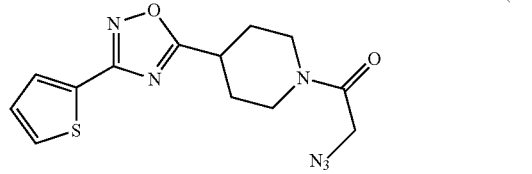
(I-1)

1) First Step: Synthesis of 4-(3-thiophen-2-yl[1,2,4]oxadiazol-5-yl)piperidinium hydrochloride

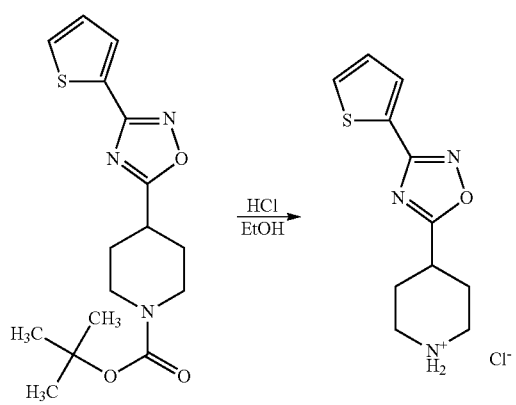

11 g of the tert-butyl ester of 4-(3-thiophen-2-yl[1,2,4]-oxadiazol-5-yl)piperidine-1-carboxylic acid (32.8 mmol) were placed in a 250 ml round-bottomed flask and dissolved in 66 ml of absolute ethanol. A solution of hydrogen chloride in dioxane (4N) (10 ml) was then added. The reaction medium was heated at 50° C. for 2 hours. The solution was then cooled and 100 ml of diethyl ether were added. The product was then filtered off. 9.56 g of a beige-colored powder were obtained.

Proton NMR (DMSO-d6, δ): 2.00 (qd, J=11.5 Hz, J=3.0 Hz, 2H); 2.25 (dd, J=11.5 Hz, J=3.0 Hz, 2H), 3.10 (q, J=10.2 Hz, 2H), 3.30 (d, J=11 Hz, 2H), 3.50 (m, 1H), 7.26 (dd, J=5.0 Hz, 3.70 Hz), 7.78 (dd, J=3.5 Hz, J=1.1 Hz), 7.85 (dd, J=5.0 Hz, J=1.2 Hz).

MS m/z: 236 (M⁺+1)

2) Second Step: Synthesis of 2-chloro-1-[4-(3-thiophen-2-yl[1,2,4]oxadiazol-5-yl)piperid-1-yl]ethanone

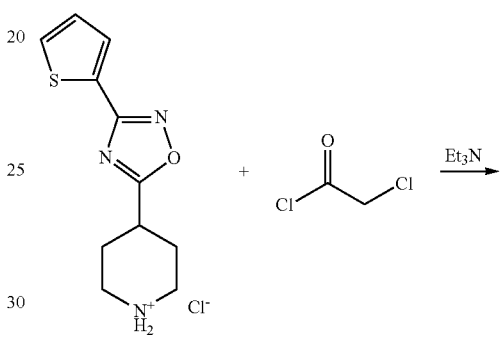

168 mg (1 eq.) of 4-(3-thiophen-2-yl[1,2,4]oxadiazol-5-yl)-piperidinium hydrochloride obtained in step 1) above and 220 µl (3.1 eq.) of triethylamine were dissolved in 1 ml of dichloromethane and stirred at a temperature of −15° C. A solution of chloroacetyl chloride (40 µl, 1 eq.) in 1 ml of dichloromethane (CH$_2$Cl$_2$) was added dropwise to the resulting suspension. The resulting mixture was stirred at room temperature for 2 hours. 20 ml of dichloromethane were then added, and the resulting organic phase was washed with three times 50 ml of 5% hydrochloric acid and then dried over MgSO$_4$, filtered and evaporated. 2-Chloro-1-[4-(3-thiophen-2-yl[1,2,4]oxa-diazol-5-yl)piperid-1-yl]ethanone was obtained in the form of a white solid, in a yield of 95%.

Proton NMR (CDCl$_3$, δ): 2.00 (m, 2H); 2.19 (m, 2H); 3.08 (m, 1H); 3.29 (m, 2H); 3.95 (m, 1H); 4.12 (s, 2H, CH$_2$); 4.45 (m, 1H); 7.17 (dd, J=5.0 Hz, J=3.0 Hz, 1H); 7.53 (d, J=5.0 Hz, 1H); 7.80 (d, J=3.0 Hz, 1H).

MS m/z: 312 (M⁺+1)

3) Third Step: Synthesis of 2-azido-1-[4-(3-thiophen-2-yl[1,2,4]oxadiazol-5-yl)piperid-1-yl]ethanone

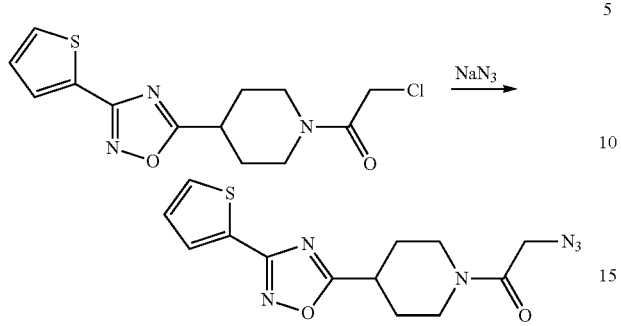

The 312 mg (1 eq.) of 2-chloro-1-[4-(3-thiophen-2-yl[1,2,4]-oxadiazol-5-yl)piperid-1-yl]ethanone obtained above in the second step were dissolved in 1 ml of dimethylformamide (DMF) in a Schlenck tube under argon. 91 mg (1.4 eq.) of sodium azide were then added. The resulting suspension was then stirred at room temperature for 18 hours. The DMF was then evaporated off under reduced pressure, and the residue was taken up in 50 ml of ethyl acetate. The resulting organic phase was washed with 20 ml of KHSO$_4$ solution (0.1 N) and 20 ml of saturated NaHCO$_3$ solution and then with twice 20 ml of brine. The organic phase was then dried over MgSO$_4$, filtered and then evaporated under reduced pressure. 2-Azido-1-[4-(3-thiophen-2-yl[1,2,4]oxadiazol-5-yl)piperid-1-yl]ethanone was obtained in the form of a translucent solid, in a yield of 80%.

Proton NMR (DMSO-d6, δ): 1.95 (m, 2H); 2.20 (m, 2H); 3.06 (m, 1H); 3.27 (m, 2H); 3.74 (m, 1H); 3.99 (s, 2H); 4.45 (m, 1H); 7.14 (dd, J=5.0 Hz, J=3.0 Hz, 1H); 7.50 (d, J=5.0 Hz, 1H); 7.78 (d, J=3.0 Hz, 1H).

MS m/z: 319 (M$^+$+1)

The following compounds were synthesized according to the same protocol as that described above for the compound of formula (I-1):

2-azido-1-[4-(3-cyclopropyl[1,2,4]oxadiazol-5-yl)piperid-1-yl]ethanone (Compound 14)

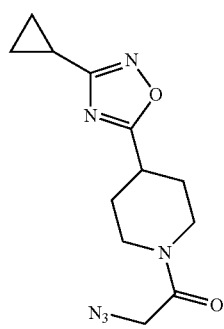

MS m/z: 277 (M$^+$+1)

$^1$H NMR (CDCl$_3$): δ 4.40 (m, 1H), 3.95 (s, 2H), 3.70 (m, 1H), 3.13 (m, 3H), 2.09 (m, 3H), 1.86 (m, 1H), 1.06 (m, 5H).

2-azido-1-[4-(3-pyrid-2-yl[1,2,4]oxadiazol-5-yl)piperid-1-yl]ethanone (Compound 13)

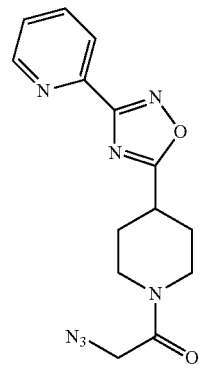

MS m/z: 314 (M$^+$+1)

2-azido-1-{4-[3-(3-chloro-2-methylphenyl)[1,2,4]oxadiazol-5-yl]piperid-1-yl}-ethanone (Compound 6)

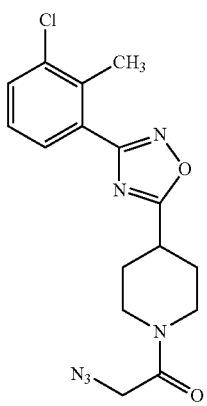

MS m/z: 361 (M$^+$+1)

$^1$H NMR (CDCl$_3$): δ 7.77 (dd, J=7.9 Hz J=1.4 Hz, 1H), 7.49 (dd, J=7.9 Hz J=1.4 Hz, 1H), 7.24 (t, J=7.9 Hz, 1H), 4.46 (m, 1H), 3.98 (s, 2H), 3.77 (m, 1H), 3.31 (m, 2H), 3.10 (m, 1H), 2.63 (s, 3H), 2.24 (m, 2H), 1.97 (m, 2H).

2-azido-1-[4-(3-pyrid-3-yl[1,2,4]oxadiazol-5-yl)piperid-1-yl]ethanone

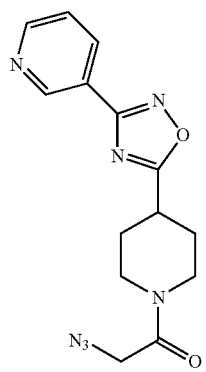

MS m/z: (M$^+$+1)

2-azido-1-{4-[3-(2-fluoro-5-trifluoromethylphenyl)[1,2,4]oxadiazol-5-yl]piperid-1-yl}ethanone

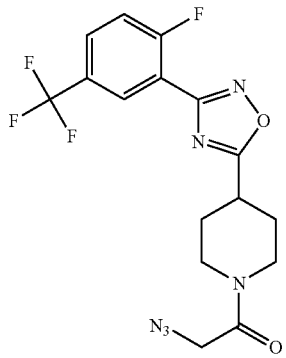

MS m/z: 399 (M⁺+1)

2-azido-1-{4-[3-(2,5-difluorophenyl)[1,2,4]oxadiazol-5-yl]piperid-1-yl}ethanone (Compound 7)

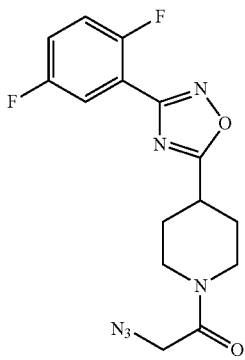

MS m/z: 349 (M⁺+1)
$^1$H NMR (CDCl$_3$): δ 7.79 (m, 1H), 7.20 (m, 2H), 6.89 (d, J=8.0 Hz, 1H), 4.47 (m, 1H), 3.98 (s, 2H), 3.77 (m, 1H), 3.31 (m, 2H), 3.10 (m, 1H), 2.23 (m, 2H), 1.97 (m, 2H).

2-azido-1-{4-[3-(2-methoxyphenyl)[1,2,4]oxadiazol-5-yl]piperid-1-yl}ethanone (Compound 11)

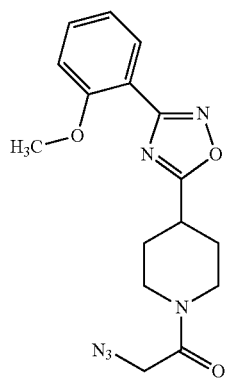

MS m/z: 343 (M⁺+1)
$^1$H NMR (CDCl$_3$): δ 7.96 (dd, J=7.5 Hz J=1.6 Hz, 1H), 7.46 (ddd, J=9.3 Hz J=7.5 Hz J=1.9 Hz 1H), 7.06 (m, 2H), 4.42 (m, 1H), 3.95 (s, 2H), 3.73 (m, 1H), 3.29 (m, 2H), 3.08 (m, 1H), 2.19 (m, 2H), 1.95 (m, 2H).

$^{13}$C NMR (CDCl$_3$): δ 179.22, 166.77, 165.57, 158.09, 132.44, 131.30, 120.70, 115.60, 111.69, 55.99, 50.80, 44.20, 41.20, 33.89, 29.45, 28.82.

2-azido-1-{4-[3-(2-chlorophenyl)[1,2,4]oxadiazol-5-yl]piperid-1-yl}ethanone (Compound 10)

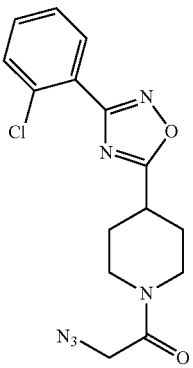

MS m/z: 347 (M⁺+1)
$^1$H NMR (CDCl$_3$): δ 7.88 (dd, J=7.4 Hz J=2.2 Hz, 1H), 7.51 (dd, J=7.4 Hz J=1.6 Hz, 1H), 7.41 (td, J=7.4 Hz J=7.4 Hz J=2.2 Hz, 1H), 7.36 (dd, J=7.4 Hz J=7.4 Hz J=1.6 Hz, 1H), 4.42 (m, 1H), 3.96 (s, 2H), 3.73 (m, 1H), 3.30 (m, 2H), 3.08 (m, 1H), 2.19 (m, 2H), 1.95 (m, 2H).

2-azido-1-[4-(3-phenyl[1,2,4]oxadiazol-5-yl)piperid-1-yl]ethanone (Compound 4)

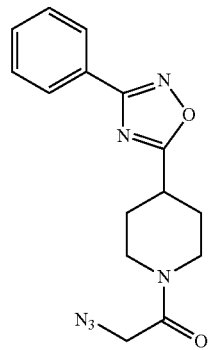

MS m/z: 313 (M⁺+1)

2-azido-1-{4-[3-(3-trifluoromethoxyphenyl)[1,2,4]oxadiazol-5-yl]piperid-1-yl}-ethanone

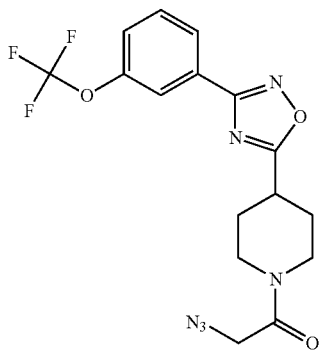

MS m/z: 397 (M⁺+1)

2-azido-1-{4-[3-(4-tert-butylphenyl)[1,2,4]oxadiazol-5-yl]piperid-1-yl}ethanone (Compound 9)

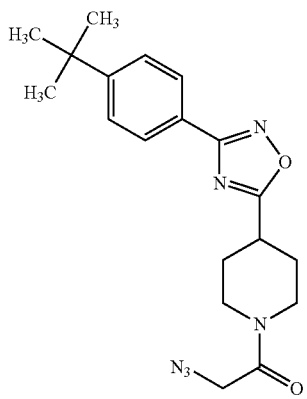

MS m/z: 369 (M⁺+1)
¹H NMR (CDCl₃): δ 7.99 (d, J=8.7 Hz, 2H), 7.50 (d, J=8.7 Hz, 2H), 4.45 (m, 1H), 3.98 (s, 2H), 3.75 (m, 1H), 3.28 (m, 2H), 3.10 (m, 1H), 2.21 (m, 2H), 1.98 (m, 2H), 1.35 (s, 9H).
¹³C NMR (CDCl₃): δ 181.00, 165.72, 154.92, 127.37, 126.70, 126.02, 123.90, 50.98, 44.37, 41.36, 35.14, 34.19, 31.33, 29.63, 28.96.

2-azido-1-{4-[3-(4-trifluoromethylphenyl)[1,2,4]oxadiazol-5-yl]piperid-1-yl}-ethanone (Compound 8)

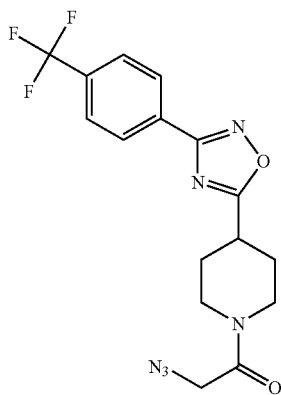

MS m/z: 381 (M⁺+1)
¹H NMR (CDCl₃): δ 8.17 (d, J=8.2 Hz, 2H), 7.72 (d, J=8.2 Hz, 2H), 4.46 (m, 1H), 3.97 (s, 2H), 3.76 (m, 1H), 3.30 (m, 2H), 3.07 (m, 1H), 2.22 (m, 2H), 1.96 (m, 2H).

2-azido-1-[4-(3-benzo[1,3]-dioxol-5-yl[1,2,4]oxadiazol-5-yl)piperid-1-yl]ethanone (Compound 12)

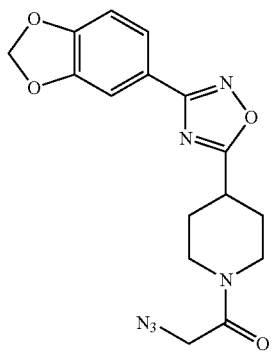

MS m/z: 357 (M⁺+1)
¹H NMR (CDCl₃): δ 7.61 (d, J=8.0 Hz, 1H), 7.49 (s, 1H), 6.89 (d, J=8.0 Hz, 1H), 6.03 (s, 2H), 4.43 (m, 1H), 3.97 (s, 2H), 3.73 (m, 1H), 3.26 (m, 2H), 3.09 (m, 1H), 2.19 (m, 1H), 1.95 (m, 2H).
¹³C NMR (CDCl₃): δ 180.24, 167.97, 165.61, 150.21, 148.15, 122.37, 120.44, 108.67, 107.41, 101.64, 50.93, 44.27, 41.24, 33.99, 29.45, 28.80.

2-azido-1-[4-(3-furan-2-yl[1,2,4]oxadiazol-5-yl)piperid-1-yl]ethanone (Compound 2)

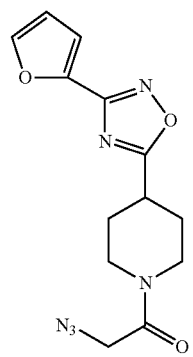

MS m/z: 303 (M⁺+1)
¹H NMR (CDCl₃): δ 7.61 (dd, J=1.8 Hz J=0.6 Hz, 1H), 7.12 (dd, J=3.3 Hz J=0.6 Hz, 1H), 6.56 (dd, J=3.3 Hz J=1.8 Hz, 1H), 4.45 (m, 1H), 3.97 (s, 2H), 3.75 (m, 1H), 3.27 (m, 2H), 3.05 (m, 1H), 2.18 (m, 2H), 1.95 (m, 2H).

2-azido-1-{4-[3-(4-fluorophenyl)[1,2,4]oxadiazol-5-yl]piperid-1-yl}ethanone (Compound 5)

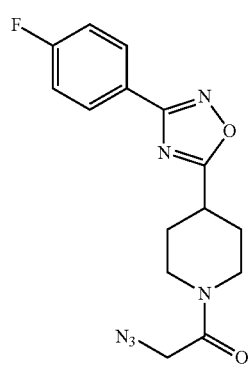

MS m/z: 331 (M⁺+1)
¹H NMR (CDCl₃): δ 8.07 (dd, J=8.8 Hz J=5.0 Hz, 2H), 7.17 (d, J=8.8 Hz, 2H), 4.46 (m, 1H), 3.98 (s, 2H), 3.76 (m, 1H), 3.29 (m, 2H), 3.10 (m, 1H), 2.22 (m, 2H), 1.97 (m, 2H).

2-azido-1-[4-(3-thiophen-3-yl[1,2,4]oxadiazol-5-yl)piperid-1-yl]ethanone (Compound 3)

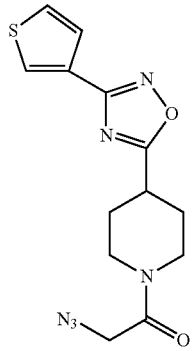

MS m/z: 319 (M$^+$+1)

$^1$H NMR (CDCl$_3$): δ 8.05 (dd, J=3.0 Hz J=1.2 Hz, 1H), 7.63 (dd, J=5.1 Hz J=1.2 Hz, 1H), 7.43 (dd, J=5.1 Hz J=3.0 Hz, 1H), 4.46 (m, 1H), 3.98 (s, 2H), 3.77 (m, 1H), 3.28 (m, 2H), 3.09 (m, 1H), 2.21 (m, 2H), 1.98 (m, 2H).

2-azido-1-[4-(3-(6-methoxybenzothiazol-2-yl[1,2,4]oxadiazol-5-yl)piperid-1-yl]ethanone (Compound 15)

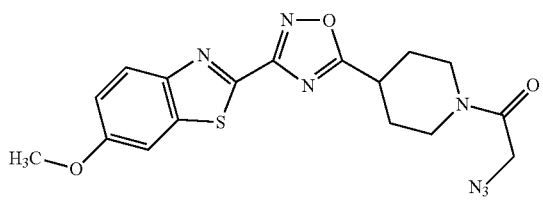

$^1$H NMR (CDCl$_3$): δ 8.08 (d, J=9.0 Hz, 1H), 7.36 (d, J=2.5 Hz, 1H), 7.14 (dd, J=9.0 Hz J=2.5 Hz, 1H), 4.48 (m, 1H), 3.96 (s, 2H), 3.88 (s, 3H), 3.76 (m, 1H), 3.37 (m, 1H), 3.26 (m, 1H), 3.04 (m, 1H), 2.26 (m, 2H), 2.00 (m, 2H).

Example 3

Synthesis of 1-[4-(3-thiophen-2-yl[1,2,4]oxadiazol-5-yl)piperid-1-yl]-2-[1,2,3]triazol-1-ylethanone (Compound (I-2))

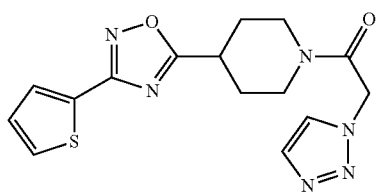

1) First Step: Synthesis of 1-[4-(3-thiophen-2-yl[1,2,4]oxadiazol-5-yl)piperid-1-yl]-2-(4-trimethylsilanyl[1,2,3]-triazol-1-yl)ethanone

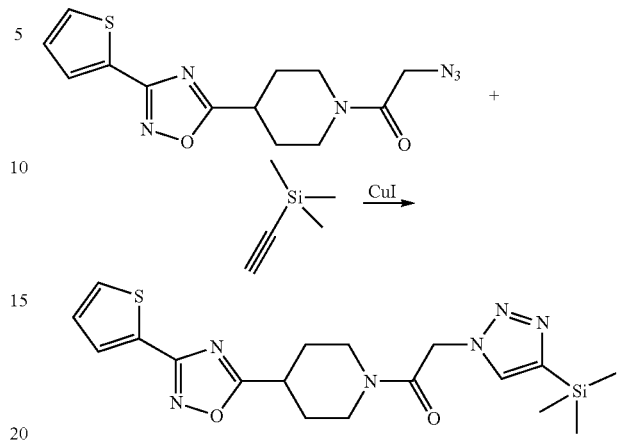

159 mg (1 eq.) of the 2-azido-1-[4-(3-thiophen-2-yl[1,2,4]oxa-diazol-5-yl)piperid-1-yl]ethanone as obtained above in Example 2, 16 mg (0.1 eq.) of copper iodide and 52 µl (2.2 eq.) of ethynyltrimethylsilane were dissolved in 2 ml of acetonitrile in a Schlenck tube, under argon. The mixture was stirred at room temperature for 48 hours. The acetonitrile was evaporated off and the residue was then purified on silica gel (80/20 ethyl acetate/cyclohexane). 1-[4-(3-Thiophen-2-yl[1,2,4]oxadiazol-5-yl)piperid-1-yl]-2-(4-trimethylsilanyl[1,2,3]triazol-1-yl)ethanone was obtained in the form of a greenish solid, in a yield of 41%.

Proton NMR (DMSO-d6, δ): 0.50 (s, 9H); 1.98 (m, 2H); 2.21 (m, 2H); 3.21 (m, 1H); 3.38 (m, 1H); 3.60 (m, 1H); 4.19 (m, 1H); 4.41 (m, 1H.); 5.84 (s, 2H); 7.17 (dd, J=5.0 Hz, J=3.0 Hz, 1H); 7.52 (d, J=5.0 Hz, 1H); 7.80 (d, J=3.0 Hz, 1H); 8.30 (brs, 1H)

MS m/z: 417 (M$^+$+1)

2) Second Step: Synthesis of 1-[4-(3-thiophen-2-yl[1,2,4]oxadiazol-5-yl)piperid-1-yl]-2-[1,2,3]triazol-1-ylethanone

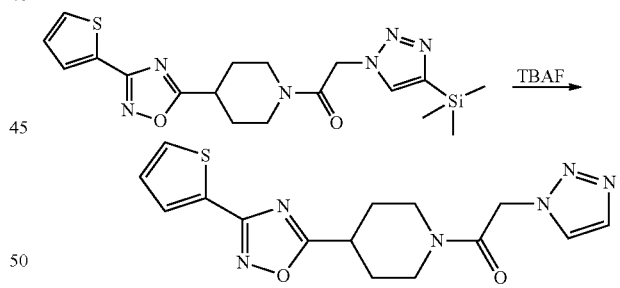

38 mg (1 eq.) of the 1-[4-(3-thiophen-2-yl[1,2,4]oxadiazol-5-yl)piperid-1-yl]-2-(4-trimethylsilanyl[1,2,3]triazol-1-yl)ethanone obtained above in the preceding step and 100 µl (1.05 eq.) of tetrabutylammonium fluoride were dissolved in 0.9 ml of THF in a sealed tube, and then refluxed for 1 hour. After cooling to room temperature, the THF was evaporated off and the residue was then purified on silica gel (90/10 CH$_2$Cl$_2$/methanol). 1-[4-(3-Thiophen-2-yl[1,2,4]oxadiazol-5-yl)piperid-1-yl]-2-[1,2,3]triazol-1-ylethanone was obtained in the form of a pale yellow solid, in a yield of 48%.

Proton NMR (CDCl$_3$, δ): 1.94 (m, 2H); 2.21 (m, 2H); 3.11 (m, 1H); 3.30 (m, 1H); 3.41 (m, 1H); 4.01 (m, 1H); 4.41 (m, 1H); 5.36 (s, 2H); 7.16 (dd, J=5.0 Hz, J=3.0 Hz, 1H); 7.51 (d, J=5.0 Hz, 1H); 7.78 (d, J=3.0 Hz, 1H); 8.30 (brs, 2H).

MS m/z: 417 (M$^+$+1)

Example 4

Synthesis of 4-iodo-N-(1-{2-oxo-2-[4-(3-thiophen-2-yl-1,2,4-oxadiazol-5-yl)piperid-1-yl]ethyl}-1H-1,2,3-triazol-4-ylmethyl)benzene-sulfonamide (Compound (I-4))

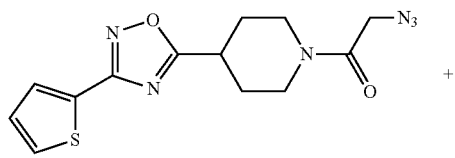

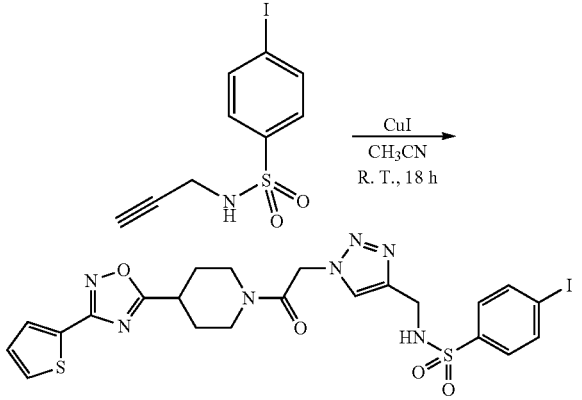

19 mg (59 µmol) of the 2-azido-1-[4-(3-thiophen-2-yl[1,2,4]-oxadiazol-5-yl)piperid-1-yl]ethanone (compound of formula (I-1)) as prepared above in Example 2 and 19 mg (59 µmol) of the alkyne were dissolved in 200 µl of acetonitrile, in a 1 ml Wheaton flask. 2 mg (5 mol %) of copper iodide dissolved in 200 µl of acetonitrile were then added to the solution. The reaction medium was stirred at room temperature for 18 hours. 21 mg of the expected product (I-4) were obtained.

$^1$H NMR (300 MHz, DMF-d7): 1.76 (m, 1H, H$_{piperidine}$); 2.04 (m, 1H, H$_{piperidine}$); 2.21 (m, 2H, H$_{piperidine}$); 3.00 (m, 1H, H$_{piperidine}$); 3.48 (m, 1H, H$_{piperidine}$); 3.51 (m, 1H, H$_{piperidine}$); 4.14 (m, 1H, H$_{piperidine}$); 4.24 (s, 2H); 4.42 (m, 1H, H$_{piperidine}$); 5.60 (m, 2H, CH$_2$); 7.33 (m, 1H, H$_{thiophene}$); 7.70 (m, 2H, H$_{Ar}$); 7.87 (m, 1H, H$_{thiophene}$); 7.94 (m, 2H, H$_{thiophene}$, H$_{triazole}$); 8.09 (m, 2H, H$_{Ar}$); 8.20 (brs, 1H, NH).

$^{13}$C NMR (75 MHz, DMF-d7): 30.00 (C$_{piperidine}$); 30.05 (C$_{piperidine}$); 33.84 (C$_{piperidine}$); 38.71 (CH$_2$); 41.00 (C$_{piperidine}$); 43.81 (C$_{piperidine}$); 50.89 (CH$_2$); 99.66 (C$_{Ar}$); 125.14 (CH$_{triazole}$); 128.12; 128.52 (CH$_{thiophene}$); 128.67 (2×CH$_{Ar}$); 129.91 (CH$_{oxadiazole}$); 130.45 (CH$_{thiophene}$); 138.44 (2×CH$_{Ar}$); 140.80 (C$_{Ar}$); 143.51; 164.17 (C$_{thiophene}$); 164.39 (C$_{triazole}$); 182.00.

MS m/z: 640 (M$^+$+1)

The following compound was synthesized according to the same protocol as that described above for the compound of formula (I-4):

2-(2,2,2-trifluoroacetyl)-1,2,3,4-tetrahydroisoquinoline-7-sulfonic acid (1-{2-oxo-2-[4-(3-thiophen-2-yl-1,2,4-oxadiazol-5-yl)piperid-1-yl]ethyl}-1H-1,2,3-triazol-4-ylmethyl)amide

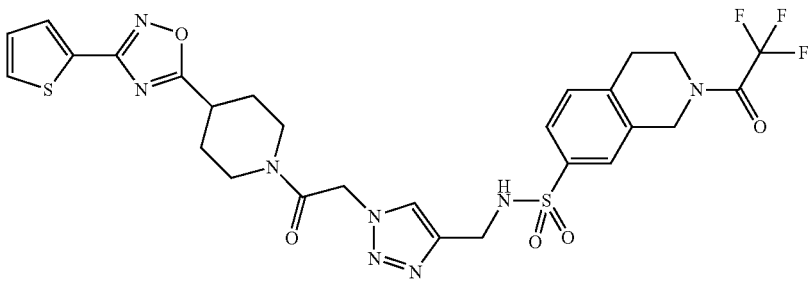

$^1$H NMR (300 MHz, DMF-d$_7$): 1.76 (m, 1H, H$_{piperidine}$); 2.00 (m, 1H, H$_{piperidine}$); 2.22 (m, 2H, H$_{piperidine}$); 3.00 (m, 1H, H$_{piperidine}$); 3.10 (m, 2H, H$_3$); 3.48 (m, 1H, H$_{piperidine}$); 3.51 (m, 1H, H$_{20}$); 3.97 (m, 2H, H$_4$); 4.14 (m, 1H, H$_{piperidine}$); 4.24 (m, 2H, CH$_2$); 4.42 (m, 1H, H$_{piperidine}$); 4.93 and 4.99 (2×s, 2H, H$_{11}$, cis and trans); 5.60 (m, 2H, H$_{16}$); 7.31-8.08 (m, 8H, 7H$_{ar}$+NH).

$^{13}$C NMR (75 MHz, DMF-d$_7$): 30.00 (C$_{piperidine}$, C$_4$); 30.05 (C$_{piperidine}$); 33.84 (C$_{piperidine}$); 38.81 (CH$_2$); 40.99 (C$_{piperidine}$); 43.00 (C$_{THQ}$); 43.78 (C$_{piperidine}$); 45.19 (C$_{THQ}$); 50.86 (CH$_2$); 125.17 (CH$_{triazole}$); 125.30; 128.12; 128.51; 129.60; 129.90; 130.45; 133.24; 138.88; 139.30; 143.69; 164.18; 164.40; 181.99.

MS m/z: 665 (M$^+$+1)

Example 5

Synthesis of the t-butyl ester of 4-(3-thiophen-2-yl[1,2,4]oxadiazol-5-ylmethyl)piperazine-1-carboxylic acid (Compound (I-5))

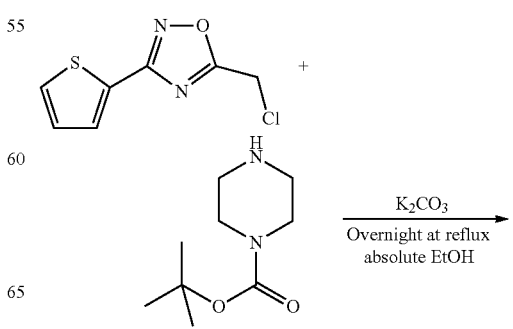

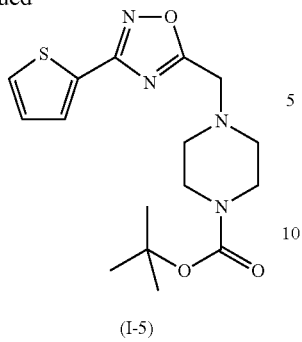

(I-5)

The starting halide (200 mg, 1 mmol) was introduced into a 10 ml round-bottomed flask, dissolved beforehand in 3 ml of absolute ethanol. The piperazine monosubstituted with a tert-butyloxy group (186 mg, 1 mmol) and $K_2CO_3$ (276 mg, 2 mmol) were then added. The mixture was refluxed overnight. After evaporating off the solvent, 30 ml of dichloromethane (DCM) were added to the reaction medium. The organic phase thus obtained was washed twice with 20 ml of $H_2O$ and then once with 20 ml of saturated NaCl solution. The organic phase was then dried over $MgSO_4$, filtered and then evaporated.

Proton NMR ($CDCl_3$, δ): 7.74 (m, 1H); 7.44 (m, 1H); 7.16 (m, 1H); 3.89 (s, 2H); 3.45 (m, 4H); 2.58 (s, 4H); 1.37 (s, 9H).

MS m/z: 295 ($M^+$-55).

Example 6

Synthesis of the t-butyl ester of 4-(5-thiophen-2-yl[1,2,4]oxadiazol-3-ylmethyl)piperazine-1-carboxylic acid (Compound I-6)

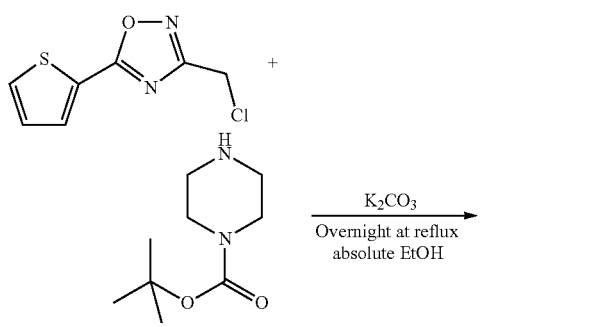

(I-6)

The starting halide (200 mg, 1 mmol) was introduced into a 10 ml round-bottomed flask, dissolved beforehand in 3 ml of absolute ethanol. The piperazine monosubstituted with a tert-butyloxy group (186 mg, 1 mmol) and $K_2CO_3$ (276 mg, 2 mmol) were then added. The mixture was refluxed overnight. After evaporating off the solvent, 30 ml of DCM were added to the reaction medium. The organic phase thus obtained was washed with twice 20 ml of $H_2O$ and then once with 20 ml of saturated NaCl solution. The organic phase was then dried over $MgSO_4$, filtered and then evaporated.

Proton NMR ($CDCl_3$, δ): 7.86 (m, 1H); 7.59 (m, 1H); 7.14 (m); 3.74 (s, 2H); 3.45 (s, 4H); 2.55 (s, 4H); 1.38 (s, 9H).

MS m/z: 295 ($M^+$–55)

Example 7

Synthesis of 2-azido-1-[4-(5-thiophen-2-yl-4H-[1,2,4]-triazol-3-yl)piperid-1-yl]ethanone (Compound I-14)

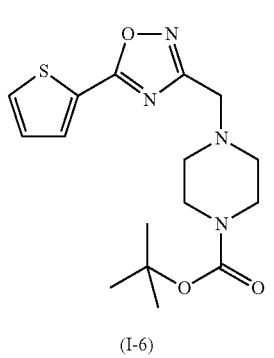

(I-14)

1) First Step: Synthesis of the t-butyl ester of 4-carbamoylpiperidine-1-carboxylic acid

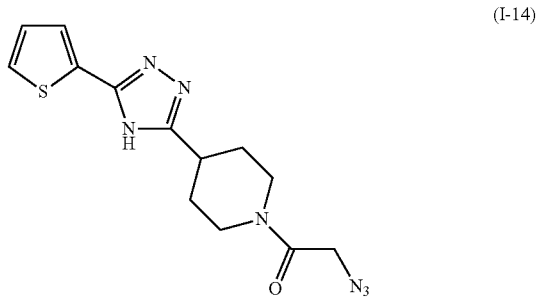

2.56 g (20 mmol) of isonipecotamide were placed in a 50 ml round-bottomed flask and 10 ml of DCM, dried beforehand over magnesium sulfate, were then added. The isonipecotamide, which was partially soluble, remained in suspension. 5.62 ml (40 mmol; 2 eq.) of diethylamine (DIEA) were then added to the medium, along with 4.8 g (1.1 eq.) of di-tert-butyl dicarbonate dissolved beforehand in a further 10 ml of DCM. The medium was stirred at room temperature until the isonipecotamide was fully dissolved. The reaction was monitored by TLC to ensure, by staining with ninhydrin, the disappearance of the isonipecotamide from the medium.

At the end of the reaction, the organic phase was washed with basic aqueous 1M NaOH solution and then dried over magnesium sulfate and evaporated. 4.31 g of a white solid were obtained.

$^1$H NMR ($CDCl_3$): δ=6.01 (s, 2H), 4.12 (m, 2H), 2.74 (m, 2H), 2.32 (m, 1H), 1.82 (m, 2H), 1.62 (m, 2H), 1.51 (s, 9H).

MS m/z: 229 ($M^+$+1)

2) Second Step: Synthesis of the t-butyl ester of 4-cyanopiperidine-1-carboxylic acid

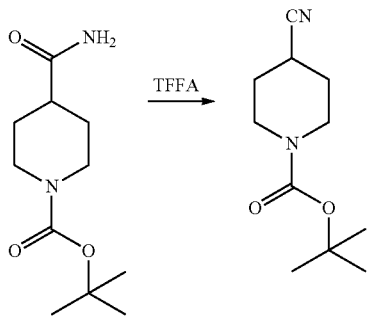

2.05 g (9 mmol) of the t-butyl ester of 4-carbamoylpiperidine-1-carboxylic acid as obtained in the first step above were introduced into a Schlenck tube in the presence of 1.7 ml of DIEA (1-1 eq.). The medium was flushed under argon, and 18 ml of anhydrous THF were then added. The reaction medium was then cooled to a temperature of 0° C. and 1.38 ml of trifluoroacetic anhydride (1.1 eq.) were added dropwise. The medium then became totally clear. If the reaction is not complete after 1 hour, a further 0.5 equivalent of DIEA and then of trifluoroacetic anhydride are added. The reaction was monitored by TLC, staining with ninhydrin. At the end of the reaction, the organic phase was washed successively with aqueous solutions of 5% NaHCO$_3$, 0.1N KHSO$_4$ and saturated NaCl solution. The expected product was not visible under UV light. In the event of appearance of a UV-visible compound, a purification by flash chromatography in a gradient of eluent ranging from cyclohexane up to a 9/1 cyclohexane/ethyl acetate mixture may be performed. 1.1 g of a very pale yellow liquid that solidified after a few hours were obtained.

$^1$H NMR: (CDCl$_3$): 3.63 (m, 2H), 3.36 (m, 2H), 2.8 (m, 1H), 1.84 (m, 4H), 1.45 (s, 9H).

MS m/z: 211 (M$^+$+1)

3) Third Step: Synthesis of the t-butyl ester of 4-(5-thiophen-2-yl-4H-[1,2,4]triazol-3-yl)piperidine-1-carboxylic acid (compound I-7)

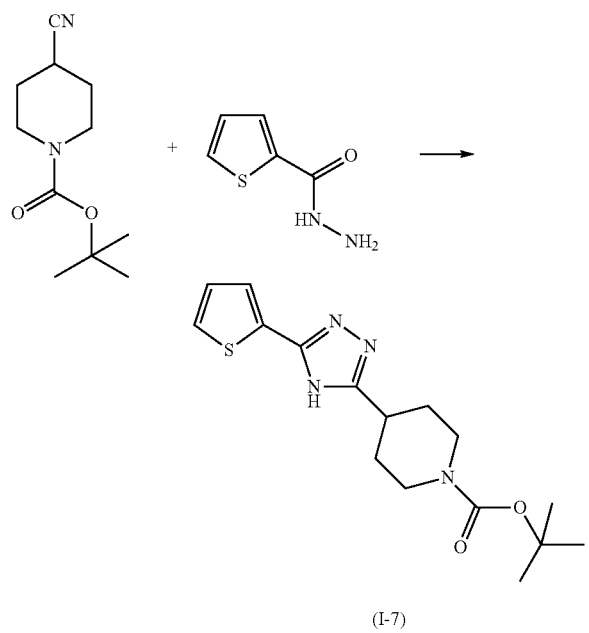

315 mg (1.5 mmol, 3 eq.) of the t-butyl ester of 4-cyanopiperidine-1-carboxylic acid obtained above in the second step were introduced into a Schlenck tube in the presence of 71 mg of thiophene-2-carboxylic hydrazide (0.5 mmol), 35 mg of K$_2$CO$_3$ (0.25 mmol; 0.5 eq.) and 2 ml of n-butanol. The medium was brought to a temperature of 150° C. and the reaction was monitored by TLC. At the end of the reaction, the reaction medium was evaporated, and the residue taken up in methanol and then neutralized by adding aqueous HCl solution. After evaporation, the compound was purified by flash chromatography in a 7/3 cyclohexane/ethyl acetate eluent, and then precipitated from diethyl ether. 102 mg of compound (I-7) as a white solid were thus obtained.

$^1$H NMR: (CDCl$_3$): δ=7.58 (dd, J=3.6 Hz, J=0.6 Hz, 1H), 7.41 (m, 1H), 7.07 (m, 1H), 4.12 (m, 2H), 2.9 (m, 3H), 1.94 (m, 2H), 1.68 (m, 2H), 1.42 (s, 9H).

MS m/z: 335 (M$^+$+1)

4) Fourth and Fifth Steps: Synthesis of 2-azido-1-[4-(5-thiophen-2-yl-4H-[1,2,4]triazol-3-yl)piperid-1-yl]ethanone (compound I-14)

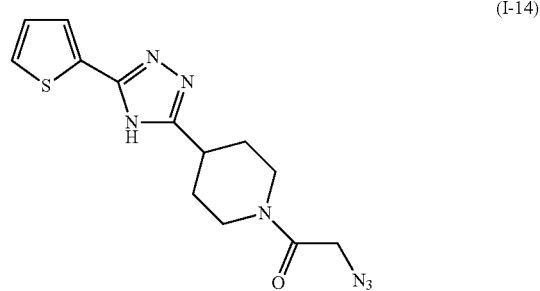

The deprotection and acetylation of this compound were performed as described previously in Example 2 above in the second and third steps of synthesis of compound (I-1), to give the expected compound (I-14).

MS m/z: 318 (M$^+$+1)

Example 8

Synthesis of the allylic ester of 4-(3-thiophen-2-yl[1,2,4]oxadiazol-5-yl)piperidine-1-carboxylic acid (Compound 18)

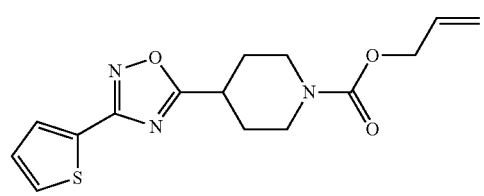

90 mg (1 eq.) of 4-(3-thiophen-2-yl[1,2,4]oxadiazol-5-yl)-piperidinium hydrochloride and 170 µl (3 eq.) of diisopropylethylamine were dissolved in 1.5 ml of dichloromethane. 39 µl (1.1 eq.) of allyl chloroformate were then added dropwise and the mixture was stirred for 2 hours at room temperature. The reaction medium was evaporated and 15 ml of ethyl acetate were added. The organic phase was washed with aqueous 1N sodium hydroxide solution (3×20 ml), with aqueous 1N hydrochloric acid solution (3×20 ml) and with saturated aqueous NaCl solution (20 ml) and then dried over MgSO$_4$ and concentrated under reduced pressure to give 92 mg (87%) of the expected compound.

$^1$H NMR analysis (CDCl$_3$): δ=7.76 (dd, J=3.7 Hz J=1.2 Hz, 1H), 7.48 (dd, J=5.0 Hz J=1.2 Hz, 1H), 7.12 (dd, J=5.0 Hz J=3.7 Hz, 1H), 5.92 (m, 1H), 5.29 (tdd, J=17.2 Hz J=2.9 Hz J=1.4 Hz, 1H), 5.20 (tdd, J=10.4 Hz J=2.9 Hz J=1.4 Hz, 1H), 4.59 (td, J=5.5 Hz J=1.4 Hz J=1.4 Hz, 1H), 4.16 (m, 2H), 4.1 (s, 2H), 3.16 (m, 1H), 3.05 (m, 2H), 2.12 (m, 2H), 1.91 (m, 2H)

$^{13}$C NMR analysis (CDCl$_3$): δ=181.06, 164.35, 154.97, 132.98, 129.56, 129.28, 128.31, 127.97, 117.52, 66.14, 43.03, 34.31, 29.01

MS: m/z 320 (M+H$^+$)

The following compounds, for which the various meanings of R are indicated, were also synthesized according to the same protocol:

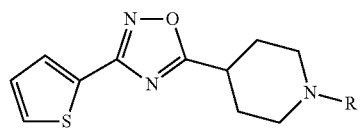

2-phenoxy-1-[4-(3-thiophen-2-yl[1,2,4]oxadiazol-5-yl)piperid-1-yl]ethanone (Compound 45)

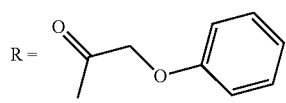

MS: m/z 370 (M+H$^+$)

$^1$H NMR (CDCl$_3$): δ=7.77 (dd, J=3.8 Hz J=1.2 Hz, 1H), 7.49 (dd, J=5.1 Hz J=1.2 Hz, 1H), 7.27 (dd, J=8.6 Hz J=1.2 Hz, 2H), 7.14 (dd, J=5.1 Hz J=3.8 Hz, 1H), 6.96 (m, 3H), 4.70 (s, 2H), 4.44 (m, 1H), 4.1 (m, 1H), 3.32 (m, 2H), 3.04 (m, 1H), 2.15 (m, 2H), 1.92 (m, 2H).

$^{13}$C NMR (CDCl$_3$): δ=180.66, 166.54, 164.38, 157.79, 129.69, 129.64, 129.36, 128.21, 121.77, 114.5767.84, 44.51, 41.25, 34.20, 29.57, 28.83.

1-[4-(3-thiophen-2-yl[1,2,4]oxadiazol-5-yl)piperid-1-yl]propan-1-one (Compound 23)

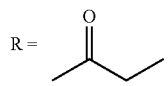

MS: m/z 292 (M+H$^+$)

$^1$H NMR (CDCl$_3$): δ=7.75 (dd, J=3.8 Hz J=1.2 Hz, 1H), 7.47 (dd, J=5.0 Hz J=1.2 Hz, 1H), 7.11 (dd, J=5.0 Hz J=3.8 Hz, 1H), 4.1 (m, 2H), 3.21 (m, 1H), 3.07 (m, 2H), 2.35 (q, J=7.5 Hz, 2H), 2.13 (m, 2H), 1.88 (m, 2H), 1.13 (t, J=7.5 Hz, 3H).

$^{13}$C NMR (CDCl$_3$): δ=180.88, 172.29, 164.33, 129.59, 129.33, 128.21, 127.98, 34.37, 29.27, 26.49, 9.52.

3-cyclopentyl-1-[4-(3-thiophen-2-yl[1,2,4]oxadiazol-5-yl)piperid-1-yl]propan-1-one (Compound 34)

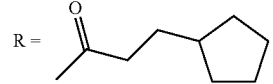

MS: m/z 360 (M+H$^+$)

$^1$H NMR (CDCl$_3$): δ=7.73 (dd, J=3.6 Hz J=1.2 Hz, 1H), 7.45 (dd, J=5.0 Hz J=1.2 Hz, 1H), 7.10 (dd, J=5.0 Hz J=3.7 Hz, 1H), 4.47 (m, 1H), 3.90 (m, 1H), 3.20 (m, 2H), 2.91 (m, 1H), 2.33 (t, J=7.8 Hz, 2H), 1.40-1.87 (m, 13H).

$^{13}$C NMR (CDCl$_3$): δ=180.88, 171.83, 164.32, 129.57, 129.31, 128.22, 127.97, 39.84, 34.36, 32.65, 32.52, 31.62, 29.15, 25.13.

3,3-dimethyl-1-[4-(3-thiophen-2-yl[1,2,4]oxadiazol-5-yl)piperid-1-yl]butan-1-one (Compound 26)

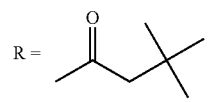

MS: m/z 334 (M+H$^+$)

$^1$H NMR (CDCl$_3$): δ=7.74 (dd, J=3.7 Hz J=1.2 Hz, 1H), 7.46 (dd, J=5.0 Hz J=1.2 Hz, 1H), 7.11 (dd, J=5.0 Hz J=3.8 Hz, 1H), 4.51 (m, 1H), 3.98 (m, 1H), 3.19 (m, 1H), 3.00 (m, 2H), 2.27 (s, 2H), 2.13 (m, 2H), 1.88 (m, 2H), 1.03 (s, 9H).

$^{13}$C NMR (CDCl$_3$): δ=180.90, 170.47, 164.33, 129.59, 129.31, 128.21, 127.98, 44.69, 34.35, 31.49, 30.06, 29.37.

2-thiophen-2-yl-1-[4-(3-thiophen-2-yl[1,2,4]oxadiazol-5-yl)piperid-1-yl]ethanone (Compound 43)

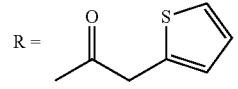

MS: m/z 360 (M+H$^+$)

$^1$H NMR (CDCl$_3$): δ=7.76 (dd, J=3.7 Hz J=1.2 Hz, 1H), 7.48 (dd, J=5.1 Hz J=1.2 Hz, 1H), 7.19 (dd, J=5.1 Hz J=1.2 Hz, 1H), 7.13 (dd, J=5.1 Hz J=3.7 Hz, 1H), 6.94 (dd, J=5.1 Hz J=3.5 Hz, 1H), 6.89 (dd, J=3.5 Hz J=1.2 Hz, 1H), 4.48 (m, 1H), 3.93 (m, 1H), 3.92 (s, 2H), 3.18 (m, 2H), 3.00 (m, 1H), 2.11 (m, 2H), 1.84 (m, 2H).

$^{13}$C NMR (CDCl$_3$): δ=180.71, 168.44, 164.36, 136.33, 129.64, 129.38, 128.01, 126.94, 126, 09, 124.86, 45.35, 41.07, 35.24, 34.15, 29.29, 28.70.

3-methyl-1-[4-(3-thiophen-2-yl[1,2,4]oxadiazol-5-yl)piperid-1-yl]butan-1-one (Compound 24)

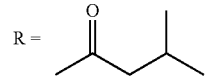

MS: m/z 320 (M+H$^+$)

$^1$H NMR (CDCl$_3$): δ=7.76 (dd, J=3.7 Hz J=1.2 Hz, 1H), 7.48 (dd, J=5.0 Hz J=1.2 Hz, 1H), 7.12 (dd, J=5.0 Hz J=3.7 Hz, 1H), 4.52 (m, 1H), 3.93 (m, 1H), 3.21 (m, 2H), 2.91 (m, 1H), 2.22 (d, J=6.4 Hz, 1H), 2.12 (m, 3H), 1.87 (m, 2H), 0.96 (d, J=6.4 Hz, 1H).

$^{13}$C NMR (CDCl$_3$): δ=180.86, 176.47, 171.22, 164.31, 129.60, 129.33, 128.16, 127.97, 44.96, 42.06, 40.72, 34.34, 29.68, 29.01, 25.82, 22.70.

Example 9

Synthesis of 4-methyl-1-[4-(3-thiophen-2-yl[1,2,4]oxadiazol-5-yl)piperid-1-YL]pentan-1-one (Compound 25)

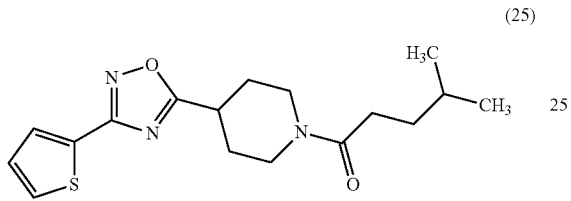

(25)

86 mg (2 eq.) of 4-methylvaleric acid, 141 mg (2 eq.) of 1-ethyl-3-[3-(dimethylamino)propyl]carbodiimide hydrochloride (EDCI) and 207 μl (4 eq.) of triethylamine were dissolved in 2 ml of dichloromethane. 100 mg (1 eq.) of 4-(3-thiophen-2-yl[1,2,4]oxadiazol-5-yl)piperidinium hydrochloride were then added to the reaction medium, which was then stirred at room temperature for 24 hours. The reaction medium was evaporated under reduced pressure and the residue was taken up in 20 ml of ethyl acetate. The organic phase was washed with aqueous 1N sodium hydroxide solution (3×30 ml), with aqueous 1N hydrochloric acid solution (3×30 ml) and with saturated aqueous NaCl solution (30 ml) and then dried over MgSO$_4$ and concentrated under reduced pressure to give 102 mg (83%) of the expected compound.

$^1$H NMR (CDCl$_3$): δ=7.72 (dd, J=3.7 Hz J=1.2 Hz, 1H), 7.45 (dd, J=5.1 Hz J=1.2 Hz, 1H), 7.09 (dd, J=5.1 Hz J=3.7 Hz, 1H), 4.46 (m, 1H), 3.89 (m, 1H), 3.19 (m, 2H), 2.90 (m, 1H), 2.3 (t, J=8 Hz, 2H), 2.10 (m, 2H), 1.84 (m, 2H), 1.49 (m, 3H), 0.86 (d, J=6.4 Hz, 6H)

$^{13}$C NMR (CDCl$_3$): δ=180.87, 171.86, 164.30, 129.58, 129.32, 128.19, 127, 98, 44.55, 40.73, 34.35, 34.21, 31.37, 29.27, 27.91, 22.39

MS: m/z 334 (M+H$^+$)

The following compounds, for which the various meanings of R are indicated, were synthesized according to the same protocol:

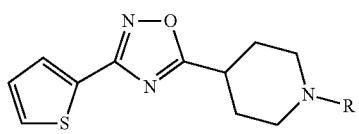

2-bicyclo[2.2.1]hept-2-yl-1-[4-(3-thiophen-2-YL[1,2,4]oxadiazol-5-YL)piperid-1-yl]ethanone (Compound 40)

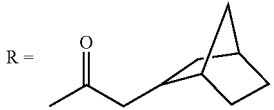

MS: m/z 372 (M+H$^+$)

$^1$H NMR (CDCl$_3$): δ 7.71 (dd, J=3.7 Hz J=1.2 Hz, 1H), 7.43 (dd, J=5.0 Hz J=1.2 Hz, 1H), 7.07 (dd, J=5.0 Hz J=3.7 Hz, 1H), 4.46 (m, 1H), δ 3.87 (m, 1H), 3.17 (m, 2H), 2.86 (m, 1H), 1.81-2.31 (m, 11H), 1.23-1.42 (m, 4H), 1 (m, 2H).

$^{13}$C NMR (CDCl$_3$): δ=180.87, 171.06, 164.27, 129.58, 129.32, 128.16, 127.97, 44.79, 41.14, 40.65, 40.04, 38.58, 38.02, 36.75, 35.30, 34.33, 29.86, 29.65, 28.99, 28.55.

2-cyclopropyl-1-[4-(3-thiophen-2-yl[1,2,4]oxadiazol-5-yl)piperid-1-yl]ethanone (Compound 33)

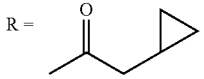

MS: m/z 318 (M+H$^+$)

$^1$H NMR (CD$_2$Cl$_2$): δ=7.80 (dd, J=3.9 Hz J=1.2 Hz, 1H), 7.56 (dd, J=5.1 Hz J=1.2 Hz, 1H), 7.20 (dd, J=5.1 Hz J=3.9 Hz, 1H), 4.55 (m, 1H), 3.93 (m, 1H), 3.27 (m, 2H), 2.94 (m, 1H), 2.27 (d, J=7.2 Hz, 2H), 2.21 (m, 2H), 1.91 (m, 2H), 1.06 (m, 1H), 0.58 (m, 2H), 0.20 (m, 2H).

3-cyclohexyl-1-[4-(3-thiophen-2-yl[1,2,4]oxadiazol-5-yl)piperid-1-yl]propan-1-one (Compound 38)

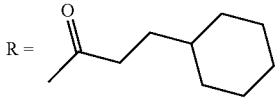

MS: m/z 374 (M+H$^+$)

$^1$H NMR (CDCl$_3$): δ=7.71 (dd, J=3.7 Hz J=1.2 Hz, 1H), 7.44 (dd, J=5.0 Hz J=1.2 Hz, 1H), 7.08 (dd, J=5.0 Hz J=3.7 Hz, 1H), 4.46 (m, 1H), 3.87 (m, 1H), 3.18 (m, 2H), 2.86 (m, 1H), 1.45-2.35 (m, 19H).

$^{13}$C NMR (CDCl$_3$): δ=180.87, 172.12, 164.228, 129.58, 129.32, 128.17, 121.97, 44.75, 40.71, 37.44, 34.33, 33.10, 32.80, 30.90, 29.63, 28.94, 26.52, 26.22.

2-phenyl-1-[4-(3-thiophen-2-yl[1,2,4]oxadiazol-5-yl)piperid-1-yl]ethanone (Compound 41)

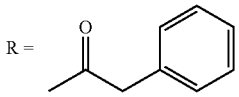

MS: m/z 354 (M+H$^+$)

$^1$H NMR (CDCl$_3$): δ=7.73 (dd, J=3.7 Hz J=1.2 Hz, 1H), 7.45 (dd, J=5.1 Hz J=1.2 Hz, 1H), 7.21-7.32 (m, 5H), 7.10 (dd, J=5.1 Hz J=3.7 Hz, 1H), 4.47 (m, 1H), 3.86 (m, 1H), 3.73 (s, 2H), 3.13 (m, 2H), 2.94 (m, 1H), 1.6-2.12 (m, 4H).

$^{13}$C NMR (CDCl$_3$): δ=180.79, 169.44, 164.30, 134.95, 129.62, 129.38, 128.82, 128.57, 128.19, 128.03, 126.90, 45.18, 41.08, 40.88, 34.15, 29.23, 28.77

3-phenyl-1-[4-(3-thiophen-2-yl[1,2,4]oxadiazol-5-yl) piperid-1-yl]propan-1-one (Compound 42)

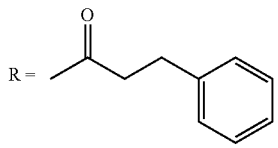

MS: m/z 368 (M+H$^+$)

$^1$H NMR (CDCl$_3$): δ=7.76 (dd, J=3.6 Hz J=1.2 Hz, 1H), 7.46 (dd, J=5.1 Hz J=1.2 Hz, 1H), 7.18-7.30 (m, 5H), 7.12 (dd, J=5.1 Hz J=3.6 Hz, 1H), 4.51 (m, 1H), 3.80 (m, 1H), 3.13 (m, 2H), 2.97 (t, J=7.9 Hz, 1H), 2.92 (m, 1H), 2.64 (t, J=7.9 Hz, 2H), 2.06 (m, 2H), 2.64 (t, J=7.9 Hz, 2H), 1.74 (m, 2H).

$^{13}$C NMR (CDCl$_3$): δ 180.83, 170.69, 164.34, 141.14, 129.59, 129.35, 128.57, 128.47, 128.30, 126.27, 44.68, 40.81, 35.03, 34.28, 31.59, 29.41, 28.90.

2-cyclohexyl-1-[4-(3-thiophen-2-yl[1,2,4]oxadiazol-5-yl)piperid-1-yl]ethanone (Compound 37)

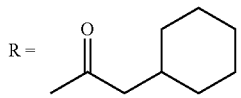

MS: m/z 360 (M+H$^+$)

$^1$H NMR (CDCl$_3$): δ=7.69 (dd, J=3.7 Hz J=1.2 Hz, 1H), 7.42 (dd, J=5.0 Hz J=1.2 Hz, 1H), 7.06 (dd, J=5.0 Hz J=3.7 Hz, 1H), 4.44 (m, 1H), 3.87 (m, 1H), 3.17 (m, 2H), 2.88 (m, 1H), 2.17 (d, J=6.7 Hz, 2H), 2.09 (m, J=6.7 Hz J=2.7 Hz, 3H), 1.59-1.83 (m, 12H).

$^{13}$C NMR (CDCl$_3$): δ=180.84, 171.29, 164.24, 129.60, 129.34, 128.07, 127.95, 45.06, 41.97, 40.67, 35.17, 34.25, 33.30, 32.95, 29.64, 28.96, 26.03.

2-cyclopent-2-enyl-1-[4-(3-thiophen-2-yl[1,2,4]oxadiazol-5-yl)piperid-1-yl]-ethanone (Compound 36)

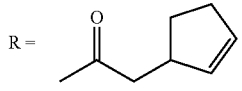

MS: m/z 344 (M+H$^+$)

$^1$H NMR (CDCl$_3$): δ=7.71 (dd, J=3.7 Hz J=1.1 Hz, 1H), 7.43 (dd, J=5.0 Hz J=1.1 Hz, 1H), 7.08 (dd, J=5.0 Hz J=3.7 Hz, 1H), 5.69 (m, 1H), 5.63 (m, 1H), 4.47 (m, 1H), 3.87 (m, 1H), 3.16 (m, 2H), 3.07 (m, 1H), 2.84 (m, 1H), 2.30 (m, 4H), 2.09 (m, 3H), 1.81 (m, 2H), 1.39 (m, 1H).

$^{13}$C NMR (CDCl$_3$): δ=180.87, 170.73, 164.28, 134.23, 131.27, 129.59, 129.33, 128.16, 127.97, 44.73, 42.12, 40.66, 39.23, 34.32, 31.79, 29.94, 29.61, 28.97.

2-(4-methylcyclohexyl)-1-[4-(3-thiophen-2-yl[1,2,4] oxadiazol-5-yl)piperid-1-yl]ethanone (Compound 39)

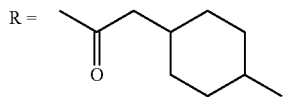

MS: m/z 374 (M+H$^+$)

$^1$H NMR (CDCl$_3$): δ=7.70 (dd, J=3.7 Hz J=1.2 Hz, 1H), 7.42 (dd, J=5.1 Hz J=1.2 Hz, 1H), 7.07 (dd, J=5.1 Hz J=3.7 Hz, 1H), 4.45 (m, 1H), 3.88 (m, 1H), 3.17 (m, 2H), 2.86 (m, 1H), 2.26 (d, J=7.2 Hz, 2H), 1.18-2.17 (m, 16H).

3-tert-butoxy-1-[4-(3-thiophen-2-YL[1,2,4]oxadiazol-5-YL)piperid-1-Yl]propan-1-one (Compound 30)

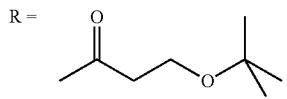

MS: m/z 364 (M+H$^+$)

$^1$H NMR (CDCl$_3$): δ 7.70 (dd, J=3.7 Hz J=1.2 Hz, 1H), 7.43 (dd, J=5.0 Hz J=1.2 Hz, 1H), 7.07 (dd, J=5.0 Hz J=3.7 Hz, 1H), 4.45 (m, 1H), 3.94 (m, 1H), 3.62 (t, J=6.8 Hz, 2H), 3.17 (m, 2H), 2.87 (m, 1H), 2.53 (q, J=6.8 Hz, 2H), 2.07 (m, 2H), 1.81 (m, 2H), 1.12 (s, 9H).

$^{13}$C NMR (CDCl$_3$): δ=180.90, 170.18, 164.27, 129.54, 129.29, 128.20, 127.94, 73.10, 58.50, 44.96, 40.71, 34.29, 34.29, 29.56, 28.95, 27.47.

2-cyclopentyl-1-[4-(3-thiophen-2-yl[1,2,4]oxadiazol-5-yl)piperid-1-yl]ethanone (Compound 35)

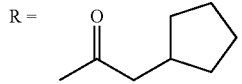

MS: m/z 346 (M+H$^+$)

$^1$H NMR (CDCl$_3$): δ=7.70 (dd, J=3.6 Hz J=1.2 Hz, 1H), 7.43 (dd, J=5.0 Hz J=1.2 Hz, 1H), 7.08 (dd, J=5.0 Hz J=3.6 Hz, 1H), 4.47 (m, 1H), 3.89 (m, 1H), 3.17 (m, 2H), 2.86 (m, 1H), 2.32 (d, J=7.5 Hz, 2H), 2.10 (m, 2H), 1.80 (m, 4H), 1.54 (m, 4H), 1.11 (m, 2H).

$^{13}$C NMR (CDCl$_3$): δ=180.96, 171.36, 164.34, 129.63, 129.37, 128.26, 128.02, 44.88, 40.70, 39.25, 36.79, 34.41, 32.75, 29.71, 29.06, 25.00.

4,4,4-trifluoro-1-[4-(3-thiophen-2-yl[1,2,4]oxadiazol-5-yl)piperid-1-yl]butan-1-one (Compound 27)

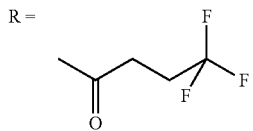

MS: m/z 346 (M+H$^+$)

$^1$H NMR (CDCl$_3$): δ=7.74 (dd, J=3.7 Hz J=1.1 Hz, 1H), 7.47 (dd, J=5.0 Hz J=1.1 Hz, 1H), 7.11 (dd, J=5.0 Hz J=3.7 Hz, 1H), 4.45 (m, 1H), 3.86 (m, 1H), 3.23 (m, 2H), 2.96 (m, 1H), 2.52 (m, 4H), 2.13 (m, 2H), 1.88 (m, 2H).

$^{13}$C NMR (CDCl$_3$): δ=180.66, 168.07, 164.34, 129.63, 129.36, 128.89, 125.24, 44.38, 40.98, 34.15, 29.74, 29.38, 28.81, 25.87.

1-[4-(3-thiophen-2-yl[1,2,4]oxadiazol-5-yl)piperid-1-yl]pent-4-en-1-one (Compound 20)

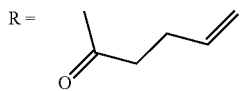

MS: m/z 318 (M+H$^+$)

$^1$H NMR (CDCl$_3$): δ 7.74 (dd, J=3.7 Hz J=1.1 Hz, 1H), 7.47 (dd, J=5.0 Hz J=1.1 Hz, 1H), 7.12 (dd, J=5.0 Hz J=3.7 Hz, 1H), 5.80 (m, 1H), 5.00 (m, 2H), 4.50 (m, 1H), 3.90 (m, 1H), 3.23 (m, 2H), 2.92 (m, 1H), 2.42 (m, 4H), 2.13 (m, 2H), 1.87 (m, 2H).

$^{13}$C NMR (CDCl$_3$): δ=180.84, 170.69, 164.35, 137.38, 129.60, 129.33, 128.22, 127.99, 115.35, 44.63, 40.75, 34.35, 32.53, 29.61, 29.29, 28.98

1-[4-(3-thiophen-2-yl[1,2,4]oxadiazol-5-yl)piperid-1-yl]pent-4-yn-1-one (Compound 21)

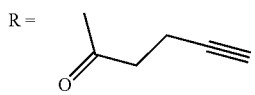

MS: m/z 346 (M+H$^+$)

$^1$H NMR (CD$_2$Cl$_2$): δ=7.80 (dd, J=3.7 Hz J=1.2 Hz, 1H), 7.57 (dd, J=4.8 Hz J=1.2 Hz, 1H), 7.20 (dd, J=4.8 Hz J=3.7 Hz, 1H), 4.52 (m, 1H), 3.95 (m, 1H), 3.26 (m, 2H), 2.95 (m, 1H), 2.60 (m, 4H), 2.19 (m, 2H), 2.04 (m, 1H), 1.93 (m, 2H).

3-oxo-3-[4-(3-thiophen-2-YL[1,2,4]oxadiazol-5-yl)piperid-1-yl]propionitrile (Compound 22)

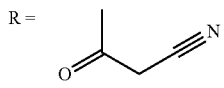

MS: m/z 303 (M+H$^+$)

$^1$H NMR (CD$_2$Cl$_2$): δ=7.81 (dd, J=3.6 Hz J=1.2 Hz, 1H), 7.58 (dd, J=4.8 Hz J=1.2 Hz, 1H), 7.21 (dd, J=4.8 Hz J=3.6 Hz, 1H), 4.46 (m, 1H), 3.79 (m, 1H), 3.58 (s, 2H), 3.30 (m, 2H), 3.09 (m, 1H), 2.25 (m, 2H), 2.00 (m, 2H).

2-methoxy-1-[4-(3-thiophen-2-yl[1,2,4]oxadiazol-5-yl)piperid-1-yl]ethanone (Compound 28)

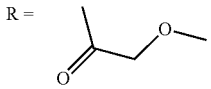

MS: m/z 308 (M+H$^+$)

$^1$H NMR (CD$_2$Cl$_2$): δ=7.81 (dd, J=3.9 Hz J=1.2 Hz, 1H), 7.57 (dd, J=4.8 Hz J=1.2 Hz, 1H), 7.21 (dd, J=4.8 Hz J=3.9 Hz, 1H), 4.48 (m, 1H), 4.12 (s, 2H), 3.95 (m, 1H), 3.43 (s, 3H), 3.29 (m, 2H), 2.97 (m, 1H), 2.19 (m, 2H), 1.89 (m, 2H).

3-methoxy-1-[4-(3-thiophen-2-yl[1,2,4]oxadiazol-5-yl)piperid-1-yl]propan-1-one (Compound 29)

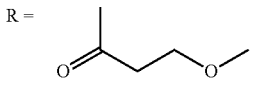

MS: m/z 322 (M+H$^+$)

Example 10

Synthesis of 1-[4-(3-thiophen-2-yl[1,2,4]oxadiazol-5-yl)-piperid-1-yl]ethanone (Compound 17)

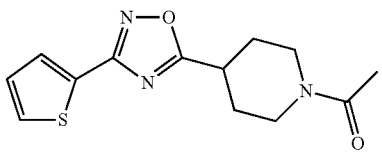

(17)

50 mg (1 eq.) of 4-(3-thiophen-2-yl[1,2,4]oxadiazol-5-yl)-piperidinium hydrochloride and 77 μl (3 eq.) of diisopropylethylamine were dissolved in 1 ml of dichloromethane. 39 μl (1.2 eq.) of acetic anhydride were added dropwise and the reaction medium was stirred for 2 hours at room temperature. The reaction medium was evaporated and the residue was taken up in 15 ml of ethyl acetate. The organic phase was washed with aqueous 1N sodium hydroxide solution (3×30 ml), with aqueous 1N hydrochloric acid solution (3×30 ml) and with saturated aqueous NaCl solution (30 ml), dried over MgSO$_4$ and concentrated under reduced pressure to give 41 mg (98%) of the expected compound.

$^1$H NMR (CDCl$_3$): δ=7.76 (dd, J=3.7 Hz J=1.1 Hz, 1H), 7.48 (dd, J=5.0 Hz J=1.1 Hz, 1H), 7.13 (dd, J=5.0 Hz J=3.7 Hz, 1H), 4.48 (m, 1H), 3.93 (m, 1H), 3.23 (m, 2H), 2.94 (m, 1H), 2.12 (m, 5H), 1.90 (m, 2H)

$^{13}$C NMR (CDCl$_3$): δ 180.79, 169.09, 164.37, 129.61, 129.35, 128.21, 128.00, 34.25, 29.70, 21.37

MS: m/z 278 (M+H$^+$)

The following compounds, for which the various meanings of R are indicated, were synthesized according to the same protocol:

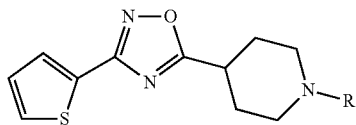

4-oxo-4-[4-(3-thiophen-2-YL[1,2,4]oxadiazol-5-YL)piperid-1-yl]butyric acid (Compound 31)

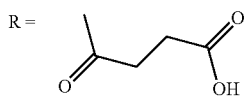

MS: m/z 336 (M+H⁺)
¹H NMR (CDCl₃): δ=7.77 (d, J=3.6 Hz, 1H), 7.50 (d, J=4.9 Hz, 1H), 7.15 (dd, J=4.9 Hz J=3.6 Hz, 1H), 4.48 (m, 1H), 3.95 (m, 1H), 3.27 (m, 2H), 3.02 (m, 1H), 2.72 (s, 4H), 2.17 (m, 2H), 1.96 (m, 2H).
¹³C NMR (CDCl₃): δ 180.77, 176.86, 170.22, 164.40, 129.68, 129.39, 128.15, 128.02, 34.19, 29.48, 27.97.

5-oxo-5-[4-(3-thiophen-2-yl[1,2,4]oxadiazol-5-yl)piperid-1-yl]pentanoic acid (Compound 32)

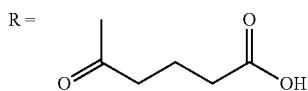

MS: m/z 350 (M+H⁺)
¹H NMR (CDCl₃): δ=7.78 (dd, J=3.7 Hz J=1.1 Hz, 1H), δ 7.50 (dd, J=5.0 Hz J=1.1 Hz, 1H), δ 7.15 (dd, J=5.0 Hz J=3.7 Hz, 1H), δ 4.51 (m, 1H), δ 3.93 (m, 1H), δ 3.26 (m, 2H), δ 2.97 (m, 1H), δ 2.48 (m, J=7 Hz, 4H), δ 2.18 (m, 2H), δ 1.95 (m, 4H).
¹³C NMR (CDCl₃): δ 180.76, 177.70, 171.12, 164.35, 129.66, 129.38, 128.16, 128.01, 34.24, 33.18, 32.14, 20.26.

Example 11

Synthesis of 4-(3-thiophen-2-yl[1,2,4]oxadiazol-5-yl)-piperidine-1-carboxylic acid phenylamide (Compound 48)

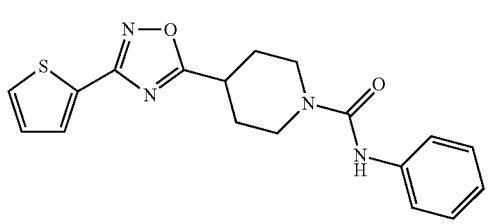

40 µl (1 eq.) of phenyl isocyanate were added to a solution of 100 mg (1 eq.) of 4-(3-thiophen-2-yl[1,2,4]oxadiazol-5-yl)piperidinium hydrochloride in 0.6 ml of pyridine. The reaction medium was stirred at room temperature overnight and then evaporated under reduced pressure. The residue obtained was chromatograph on a thick layer of silica (eluent: CH₂Cl₂/MeOH (95/5; v/v)). After evaporating off the solvent, 48 mg (37%) of the expected compound were obtained.
¹H NMR (CD₂Cl₂): δ=7.80 (dd, 1H, J=3.69 Hz, J=1.21 Hz), 7.56 (dd, 1H, J=5.04 Hz, J=1.21 Hz), 7.32 (m, 4H), 7.19 (dd, 1H, J=5.04 Hz, J=3.68 Hz), 7.04 (m, 1H), 4.08 (m, 2H), 3.14 (m, 3H), 2.21 (m, 2H), 2.02 (m, 2H).
MS: m/z 355 (M+H⁺)

The following compounds were synthesized according to the same protocol, starting with the corresponding isocyanate or isothiocyanate:

4-(3-thiophen-2-yl[1,2,4]oxadiazol-5-yl)piperidine-1-carbothioic acid phenylamide (Compound 49)

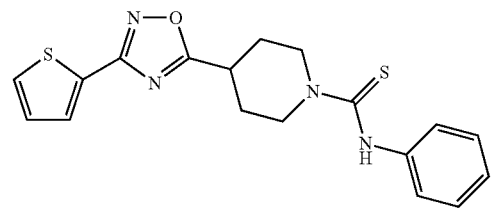

MS: m/z 371 (M+H⁺)
¹H NMR (CD₂Cl₂): δ 7.76 (dd, 1H, J=3.68 Hz, J=1.21 Hz), 7.74-7.79 (m, 1H), 7.56 (dd, 1H, J=5.04 Hz, J=1.21 Hz), 7.34 (m, 2H), 7.16 (m, 4H), 4.51 (m, 2H), 3.31 (m, 3H), 2.15 (m, 2H), 1.95 (m, 2H).

4-(3-thiophen-2-yl[1,2,4]oxadiazol-5-yl)piperidine-1-carboxylic acid thiophen-2-ylamide (Compound 50)

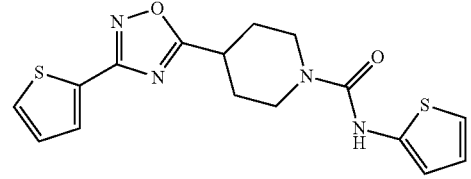

MS: m/z 361 (M+H⁺)
¹H NMR (CD₂Cl₂): δ 7.79 (dd, 1H, J=3.61 Hz, J=1.21 Hz), 7.55 (dd, 1H, J=5.02 Hz, J=1.21 Hz), 7.18 (dd, 2H, J=5.07 Hz, J=3.67 Hz), 7.15-7.18 (m, 1H), 4.05 (m, 2H), 3.14 (m, 3H), 2.20 (m, 2H), 1.92 (m, 2H).

4-(3-thiophen-2-yl[1,2,4]oxadiazol-5-yl)piperidine-1-carbothioic acid cyclopropylamide (Compound 52)

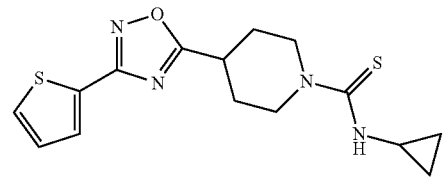

MS: m/z 335 (M+H⁺)

¹H NMR (MeOD): δ 7.78 (dd, 1H, J=3.71 Hz, J=1.17 Hz), 7.66 (dd, 1H, J=5.04 Hz, J=1.17 Hz), 7.18 (dd, 1H, J=4.99 Hz, J=3.63 Hz), 4.61 (m, 2H), 3.27 (m, 3H), 2.96 (m, 1H), 2.13 (m, 2H), 1.81 (m, 2H), 0.76 (m, 2H), 0.60 (m, 2H).

Example 12

Synthesis of 4-(3-thiophen-2-yl[1,2,4]oxadiazol-5-yl)piperidine-1-carboxylic acid cyclopropylamide (Compound 51)

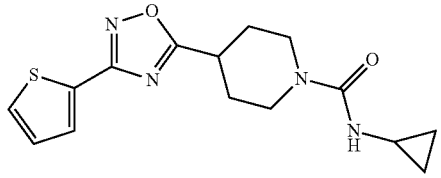

(51)

54.60 mg (1 eq.) of triphosgene were added to a suspension of 150 mg (3 eq.) of 4-(3-thiophen-2-yl[1,2,4]oxadiazol-5-yl)piperidinium hydrochloride and 102.63 μl (4 eq.) of triethylamine in 2 ml of toluene. The reaction medium was stirred overnight at room temperature and then filtered. The filtrate thus collected was concentrated under reduced pressure. The residue obtained was taken up in 2 ml of dichloromethane, followed by addition of 77 μL (1 eq.) of triethylamine and 77.44 μl (2 eq.) of cyclopropylamine. The reaction medium was stirred for 20 hours at room temperature and then concentrated to dryness. The residue was chromatograph on a thick layer of silica (eluent: CH₂Cl₂/MeOH (95/5; v/v)) to give 80 mg (45%) of the expected product.

¹H NMR (MeOD, δ): 7.76 (dd, 1H, J=3.67 Hz, J=1.05 Hz), 7.64 (dd, 1H, J=5.09 Hz, J=1.01 Hz), 7.16 (dd, 1H, J=4.98 Hz, J=3.77 Hz), 3.98 (m, 2H), 3.22 (m, 1H), 2.96 (m, 2H), 2.50 (m, 1H), 2.07 (m, 2H), 1.76 (m, 2H), 0.63 (m, 2H), 0.44 (m, 2H).

MS: m/z 319 (M+H⁺)

Example 13

Synthesis of 1-phenylmethanesulfonyl-4-(3-thiophen-2-yl[1,2,4]oxadiazol-5-yl)piperidine (Compound 53)

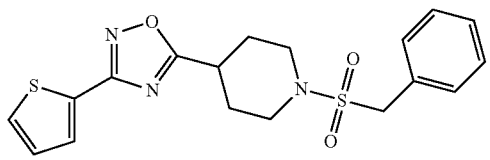

(53)

140.30 mg (2 eq.) of benzenesulfonyl chloride were added to a solution of 100 mg (1 eq.) of 4-(3-thiophen-2-yl[1,2,4]oxadiazol-5-yl)-piperidinium hydrochloride and 102.63 μl (2 eq.) of triethylamine in 1.5 ml of dichloroethane. The mixture was stirred overnight at room temperature and then evaporated under reduced pressure. The residue was chromatograph on a thick layer of silica (eluent: CH₂Cl₂) to give, after evaporating off the solvent, 74 mg (52%) of the expected product.

¹H NMR (CD₂Cl₂ δ): 7.78 (dd, 1H, J=3.7 Hz, J=1.17 Hz), 7.56 (dd, 1H, J=5.04 Hz, J=1.15 Hz), 7.40 (m, 5H), 7.17 (dd, 1H, J=5.01 Hz, J=3.67 Hz), 4.26 (s, 2H), 3.60 (m, 2H), 3.06 (m, 1H), 2.86 (m, 2H), 2.09 (m, 2H), 1.84 (m, 2H).

MS: m/z 390 (M+H⁺)

The following compound was synthesized according to the same protocol:

1-(Thiophene-3-sulfonyl)-4-(3-thiophen-2-yl[1,2,4]oxadiazol-5-yl)piperidine

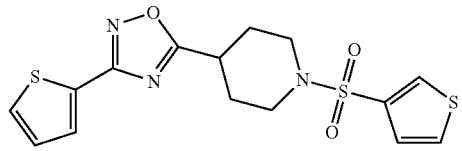

MS: m/z 382 (M+H⁺)

Example 14

Synthesis of phenyl[4-(3-thiophen-2-yl[1,2,4]oxadiazol-5-yl)piperid-1-yl]methanone (Compound 54)

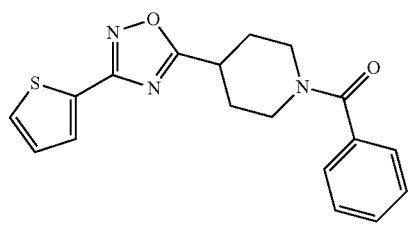

(54)

67.40 mg (1 eq.) of benzoic acid, 106 mg (1 eq.) of EDCI and 165 μl (2 eq.) of triethylamine were dissolved in 2 ml of dichloromethane. 150 mg (1 eq.) of 4-(3-thiophen-2-yl[1,2,4]oxadiazol-5-yl)piperidinium hydrochloride dissolved in 2 ml of dichloromethane and 165 μl (2 eq.) of triethylamine were added to the reaction medium, which was stirred at room temperature overnight. The reaction medium was evaporated under reduced pressure and the residue was chromatographed on a thick layer (eluent: CH₂Cl₂/MeOH (98/2: v/v)) to give 98 mg (52%) of the expected product.

¹H NMR (CD₂Cl₂, δ): 7.76 (dd, 1H, J=3.40 Hz, J=1.10 Hz), 7.52 (dd, 1H, J=4.88 Hz, J=1.09 Hz), 7.40 (m, 5H), 7.15 (dd, 1H, J=5.34 Hz, J=3.86 Hz), 4.55-4.65 (m, 1H), 3.80-3.90 (m, 1H), 3.24 (m, 1H), 3.10 (m, 2H), 2.05-2.30 (m, 2H), 1.80-2.00 (m, 2H).

MS: m/z 340 (M+H⁺)

The following compounds were synthesized according to the same protocol:

2-thiophen-3-yl-1-[4-(3-thiophen-2-yl[1,2,4]oxadiazol-5-yl)piperid-1-yl]ethanone (Compound 60)

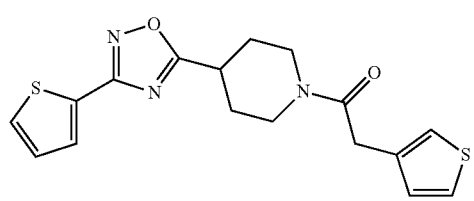

(60)

¹H NMR (MeOD, δ): 7.77 (dd, 1H, J=3.7 Hz, J=1.21 Hz), 7.65 (dd, 1H, J=5.06 Hz, J=1.21 Hz), 7.39 (dd, 1H, J=4.96 Hz, J=2.96 Hz), 7.18 (m, 2H), 7.03 (dd, 1H, J=4.96 Hz, J=1.30 Hz), 3.82 (s, 2H), 3.25-3.35 (m, 2H), 2.95 (m, 1H), 2.02 (m, 2H), 1.60 (m, 2H).
MS: m/z 360 (M+H⁺)

2-(2-aminothiazol-4-yl)-1-[4-(3-thiophen-2-yl[1,2,4]oxadiazol-5-yl)piperid-1-yl]ethanone

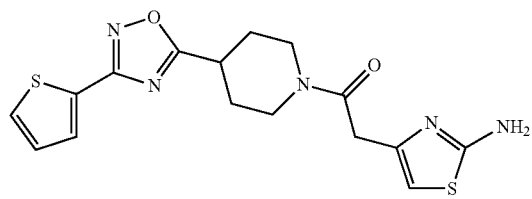

MS: m/z 376 (M+H⁺)

Example 15

Synthesis of 1-{4-[3-(2-aminothiazol-5-yl)[1,2,4]oxadiazol-5-yl]piperid-1-yl}-2-cyclopropylethanone

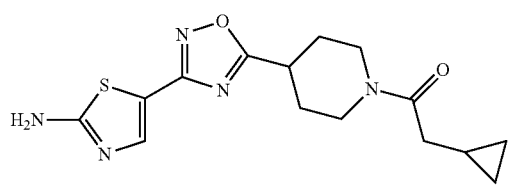

1) First Step: Synthesis of 2-aminothiazole-5-carbonitrile

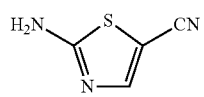

6.17 ml (1 eq.) of dibromine were added to a solution of 10.10 ml (1 eq.) of 3-methoxyacrylonitrile in 35 ml of cold acetonitrile at a temperature of 0° C. The medium was stirred for 20 minutes and then 80 ml of distilled water, cooled to 5° C., were added thereto. The mixture was stirred vigorously for 1 hour, and 8.88 g (0.9 eq.) of sodium acetate were then added. After stirring for 15 minutes, 10.07 g (1.1 eq.) of thiourea were added and the reaction medium was stirred at a temperature of between 0° C. and 10° C. for 2 hours. 5.92 g (0.6 eq.) of sodium acetate were then added and the reaction medium was maintained at 60° C. for 3 hours. The temperature of the medium was lowered to 10° C. and sodium hydroxide (10N) was added thereto until a pH of 4 was obtained. The precipitate formed was filtered off by suction, washed with water and purified using charcoal in acetone at 50° C. (1 hour 30 minutes). The mixture was filtered while hot and the collected filtrate was concentrated under reduced pressure. The residue obtained was washed with heptane and then with a heptane/acetone mixture (2/1; v/v) to give 12.5 g (83%) of the expected product.

¹H NMR (DMSO-d₆, δ): 7.82 (s, 1H), 8.05-8.20 (m, 2H).
MS: m/z 126 (M⁺+1).

2) Second Step: Synthesis of 2-amino-N-hydroxythiazole-5-carboxamidine

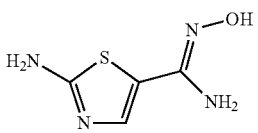

4.42 ml (1.6 eq.) of DIEA and then 1.66 g (1.5 eq.) of hydroxylamine hydrochloride were added to a solution of 2 g (1 eq.) of the carbonitrile, obtained above in the preceding step, in 26.5 ml of ethanol. The medium was refluxed for 4 hours and then concentrated to dryness. The residue obtained was taken up in water and the aqueous phase was extracted twice with ethyl acetate. The combined organic phases were dried over MgSO₄ and concentrated to dryness to give 1.77 g (70%) of the expected product.

¹H NMR (DMSO-d₆, δ): 5.70-5.90 (m, 2H), 7.00-7.20 (m, 2H), 7.35 (s, 1H), 9.41 (s, 1H).
MS: m/z 159 (M⁺+1).

The following compound was also synthesized according to the same protocol:

3-dibenzylamino-N-hydroxybenzamidine

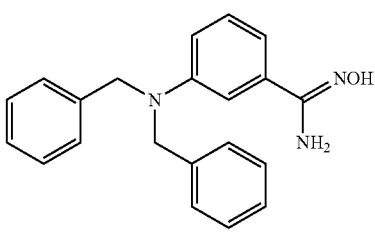

¹H NMR (MeOD, δ): 6.75 (m, 14H), 4.69 (m, 4H).
MS m/z: 332 (M⁺+1).

3) Third Step: Synthesis of the tert-butyl ester of 4-[3-(2-aminothiazol-5-yl)-[1,2,4]oxadiazol-5-yl]piperidine-1-carboxylic acid

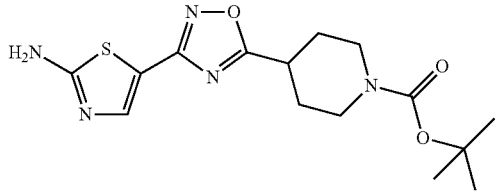

0.725 g (1 eq.) of the mono-tert-butyl ester of piperidine-1,4-dicarboxylic acid, 1.20 g (1 eq.) of O-benzotriazol-1-yl-N,N,N',N'-tetramethyl-uronium hexafluorophosphate (HBTU), 0.097 g (0.2 eq.) of 1-hydroxy-benzotriazole hydrate (HOBT) and 2.75 ml (5 eq.) of ethyldiisopropylamine in 50 ml of dimethylformamide (DMF) were stirred for 1 minute. 0.500 g (1 eq.) of 2-amino-N-hydroxythiazole-5-carboxamidine was then added to the suspension. The resulting mixture was stirred at room temperature overnight. The mixture was then concentrated to dryness and the residue obtained was taken up in ethyl acetate and then washed successively with water, with saturated aqueous NaCl solution and with saturated NaHCO$_3$ solution. The combined organic phases were dried over MgSO$_4$ and concentrated to dryness. The residue obtained was taken up in 15 ml of DMF and stirred at reflux for 2 hours. The medium was concentrated to dryness. The residue was taken up in ethyl acetate and washed with 5% NaHCO$_3$ solution, and then with saturated aqueous NaCl solution. The combined organic phases were dried over MgSO$_4$ and evaporated under reduced pressure. The residue was chromatographed on a thick layer (eluent: CH$_2$Cl$_2$/MeOH (95/5 v/v)) to give 80 mg (7%) of the expected product.

$^1$H NMR (CD$_2$Cl$_2$, δ): 7.75 (s, 1H), 5.50-5.70 (m, 2H), 4.09 (m, 2H), 3.09 (m, 1H), 2.92 (m, 2H), 2.06 (m, 2H), 1.47 (m, 2H), 1.47 (s, 9H).

MS m/z: 352 (M$^+$+1).

The following compound was also synthesized according to the same protocol:

tert-Butyl ester of 4-[3-(3-dibenzylaminophenyl)[1,2,4]oxadiazol-5-yl]piperidine-1-carboxylic acid

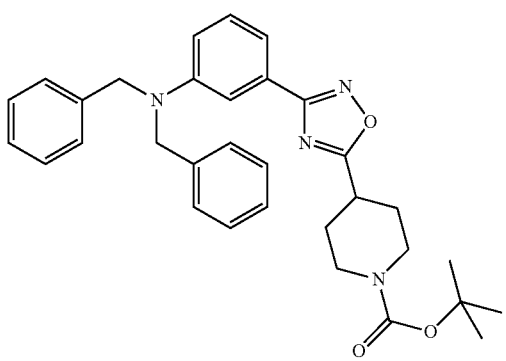

$^1$H NMR (CD$_2$Cl$_2$, δ): 7.47 (m, 1H), 7.25 (m, 10H), 6.86 (m, 1H), 4.76 (s, 4H), 4.08 (m, 2H), 3.12 (m, 1H), 2.94 (m, 2H), 2.05 (m, 2H), 1.77 (m, 2H), 1.48 (s, 9H).

MS m/z: 525 (M$^+$+1).

4) Fourth Step: Synthesis of 5-(5-piperid-4-yl[1,2,4]oxadiazol-3-yl)thiazol-2-yl-amine dihydrochloride

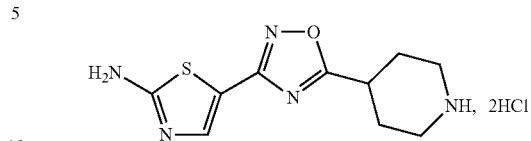

80 mg (1 eq.) of the tert-butyl ester of 4-[3-(2-aminothiazol-5-yl)[1,2,4]oxadiazol-5-yl]piperidine-1-carboxylic were dissolved in 2 ml of absolute ethanol. A 4N solution of hydrogen chloride in dioxane (0.57 ml) was added thereto. The reaction medium was stirred overnight at room temperature and then concentrated to dryness to give 70 mg (95%) of the expected product.

$^1$H NMR (MeOD, δ): 7.98 (s, 1H), 3.48 (m, 3H), 3.19 (m, 2H), 2.39 (m, 2H), 2.07 (m, 2H).

$^{13}$C NMR (MeOD, δ): 181.13, 171.01, 161.23, 129.29, 110.57, 42.54, 42.53, 31.45, 25.53, 25.52.

MS m/z: 252 (M$^+$+1).

The following compound was also synthesized according to the same protocol:

Dibenzyl[3-(5-piperid-4-yl[1,2,4]oxadiazol-3-yl)phenyl]amine hydrochloride

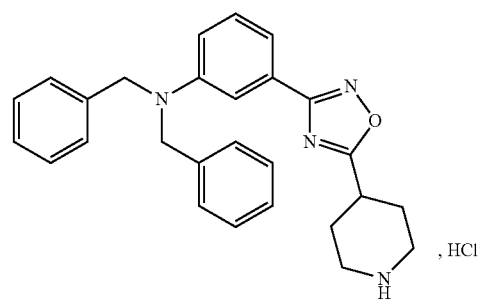

$^1$H NMR (MeOD, δ): 7.93 (m, 2H), 7.52 (m, 2H), 7.27 (m, 10H), 5.03 (s, 4H), 3.48 (m, 3H), 3.19 (m, 2H), 2.37 (m, 2H), 2.11 (m, 2H).

MS m/z: 426 (M$^+$+1).

5) Fifth Step: Synthesis of 1-{4-[3-(2-aminothiazol-5-yl)[1,2,4]oxadiazol-5-yl]-piperid-1-yl}-2-cyclopropylethanone

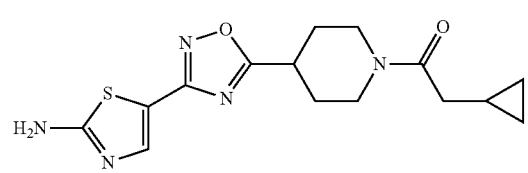

18.52 mg (1 eq.) of cyclopropylacetic acid, 35.47 mg (1 eq.) of EDCI and 26 μl (1 eq.) of triethylamine were dissolved in 200 μl of dichloromethane. The mixture was stirred for 10 minutes, and the 5-(5-piperid-4-yl[1,2,4]oxadiazol-3-yl)thiazol-2-ylamine hydrochloride, obtained above in the preceding step, was dissolved in 2 ml of $CH_2Cl_2$, and 52 µl (2 eq.) of $Et_3N$ were then added. The reaction medium was stirred at room temperature overnight and then concentrated to dryness. The residue obtained was chromatographed on a thick layer of silica (eluent: $CH_2Cl_2$/MeOH (95/5 v/v)) to give 47 mg (76%) of the expected product.

$^1$H NMR (MeOD, δ): 7.68 (s, 1H), 4.47 (m, 1H), 3.99 (m, 1H), 3.32 (m, 2H), 2.99 (m, 1H), 2.36 (d, 2H, J=6.87 Hz), 2.15 (m, 2H), 1.74 (m, 2H), 0.98 (m, 1H), 0.57 (m, 2H), 0.19 (m, 2H).

$^{13}$C NMR (MeOD, δ): 180.96, 172.27, 162.86, 142.02, 128.55, 127.83, 44.79, 40.59, 37.83, 33.88, 29.44, 28.68, 6.90, 3.70, 3.59.

MS m/z: 334 ($M^+$+1).

The following compound was also synthesized according to the same protocol:

2-cyclopropyl-1-{4-[3-(3-dibenzylaminophenyl)[1,2,4]oxadiazol-5-yl]piperid-1-yl}ethanone (compound 57)

(57)

$^1$H NMR ($CD_2Cl_2$, δ): 6.88 (m, 1H), 7.24 (m, 12H), 7.48 (m, 1H), 4.75 (s, 2H), 4.46 (m, 1H), 3.87 (m, 1H), 3.21 (m, 1H), 2.93 (m, 1H), 2.28 (d, 2H, J=6.68 Hz), 2.13 (m, 2H), 1.80 (m, 1H), 0.86 (m, 1H), 0.53 (m, 2H), 018 (m, 2H).

MS m/z: 507 ($M^+$+1).

Example 16

Demonstration of the Potentiating Effect on ETH Activity by the Compound of Formula (I-3)

The aim of this example is to demonstrate the increase in sensitivity to ETH of *Mycobacterium tuberculosis* bacteria, when this antibiotic is combined with a compound of formula (I). In this example, the compound of formula (I-3) as prepared above in Example 1 was used.

1) Materials and Methods

The ability of the compound of formula (I-3) to increase the sensitivity to ETH of the test strain was studied after preparation of an agar gel inoculated, in supercooled state, with about $10^8$ *Mycobacterium tuberculosis* bacilli (strain H37RV), followed by pouring into Petri dishes.

Holes were made in the thickness of the cooled gel using a sample punch, in order to form wells capable of receiving the antibiotic ETH and/or the compound of formula (I-3), into the bottom of which wells a small thickness of sterile gel is poured beforehand so as to avoid any contact of the test compounds with the plastic base of the Petri dish.

The test compounds are then placed in the bottom of the wells.

Three Petri dishes A, B and C were thus prepared:
Dish A: Hole A1: no product (control)
    Hole A2: 20 nmol of compound of formula (I-3)
Dish B: Hole B1: 2 µg of ETH
    Hole B2: 4 µg of ETH
Dish C: Hole C1: 2 µg of ETH+20 nmol of compound of formula (I-3)
    Hole C2: 4 µg of ETH+20 nmol of compound of formula (I-3)

Dishes A, B and C were then left for three weeks in an oven at a temperature of 37° C., and the regions of inhibition of mycobacterial growth around the wells were then observed.

2) Results

The results obtained are given in the attached FIG. 1.

In this figure, it is seen that, at the test doses, the compound of formula (I-3) does not show any bacterial toxicity (no inhibition of growth around well A2). Dish B shows that the deposition of 2 µg (hole B1) or 4 µg (hole B2) of ETH into the wells is insufficient to lead to inhibition of growth at the periphery, which means that the minimum inhibitory concentration is not reached with these doses. On the other hand, these doses of ETH strongly inhibit the mycobacterial growth when they are used in combination with 20 nmol of compounds of formula (I-3) (holes C1 and C2).

These results consequently demonstrate that the compounds of formula (I) in accordance with the invention make it possible to potentiate the bactericidal activity of ETH with respect to *M. tuberculosis*.

Example 17

In Vitro Demonstration of the Activity of the Compounds of the Invention

1) Materials and Methods a) Measurement of the Activity of the Compounds on the Inhibition of Interaction of EthR with its Target DNA Sequence The in vitro measurements of inhibition of binding of the EthR protein to its target DNA sequence were performed on a machine of BIAcore®2000 type (AB, Uppsala, Sweden).

The chips used are CM5 chips sold by the company GE Healthcare. Both the channels of a chip were activated with a solution containing 200 mM of EDC(N-ethyl-N'-(3-diethylaminopropyl)carbodiimide) and 50 mM of NHS (N-hydroxysuccinimide). Next, streptavidin (500 ng/µl in a solution containing 10 mM of sodium acetate (pH 3.5) was injected over 12 minutes at a flow rate of 10 µl/minute. The 106-base-pair biotinylated DNA fragment corresponding to the ethA-R intergene region was deposited on one of the two channels of the chip at a rate of 200 ng/ml in order to obtain stable binding of streptavidin corresponding to 50 RU (resonance units). This DNA fragment was obtained by PCR using the chromosomal DNA of *M. tuberculosis* H37Rv as matrix and O-270: 5'-CGGTCATGGATCCACGCTATCAAC-3' (SEQ ID: No. 1) and O-271: 5'-biotin-CTGACTGGCCGCGGAGGTGGT-3' (SEQ ID: No. 2). The second channel was functionalized with a 113-base-pair biotinylated DNA fragment (fragment +14 to +127 of the bla gene of *E. coli* PCR-amplified using the following oligonucleotides: O-343: 5'-TTTCCGTGTCGC- CCTTATTCC-3' (SEQ ID: No. 3) and O-344: 5'-biotin-CCACTCGTGCACCCAACTGAT-3' (SEQ ID: No. 4).

Measurement of the binding of the EthR protein to the immobilized DNA was performed at 37° C. in a reference buffer containing 10 mM of Tris-HCl (pH=7.5), 200 mM of NaCl, 0.1 mM of EDTA, 1 mM of DTT and 1% of DMSO at a flow rate of 20 μl/minute. The specific interaction (SI) of EthR with the 106-base-pair double-stranded DNA sequence, expressed in resonance units, corresponds to the difference in signal observed between the two channels.

For each inhibition measurement, the compounds of the invention are dissolved in the reference buffer at a concentration of 3 μM. The compounds of the invention are then incubated in the presence of the protein (540 nM) at 37° C. for 5 minutes, and each solution is then injected onto the two channels of the chip for 3 minutes at a flow rate of 20 μl/minute. The inhibition values are calculated at the end of the injection according to the following equation:

$$\% \text{ inhibition} = 100 \times \frac{SI_{EthR} - SI_{EthR+ligand}}{SI_{EthR}}$$

in which $SI_{EthR}$ corresponds to the value measured without ligand and $SI_{EthR+ligand}$ corresponds to the value measured in the presence of to ligand.

b) In Vitro Measurement of the $IC_{50}$ of the Compounds of the Invention.

The $IC_{50}$ is the concentration needed to obtain 50% inhibition of the interaction of the EthR protein on the target DNA sequence. The in vitro measurement of this datum was performed according to the same principle as for the measurement of inhibition of the EthR/DNA binding using the BIAcore technique.

The specific interaction between EthR and the specific 106-bp DNA fragment was measured on a range of six concentrations of the compounds of the invention, this range extending from 0.11 μM to 27 μM. The $IC_{50}$ values are then extrapolated from the sigmoid curves obtained.

In Vitro Measurement of the $MIC_{ETH}$ of the Compounds of the Invention on *M. bovis* BCG The MIC is the minimum inhibitory concentration in µM of ethionamide (ETH) needed to inhibit the growth of mycobacteria. In the absence of the compounds of the invention, the concentration of ethionamide needed to prevent the growth of the mycobacteria is 6 µM. The minimum inhibitory concentration of ETH ($MIC_{ETH}$*) in the presence of a fixed concentration of compounds according to the invention (25 µM) makes it possible to evaluate the percentage of potentiation that corresponds to the following equation:

$$\%\ \text{potentiaton} = 100 \times \frac{6}{MIC^{*}_{ETH}}$$

BCG 1173P2 was cultured for 10 days in Sauton medium in a cell culture flask without agitation. The culture was then diluted in fresh Sauton medium to obtain an optical density (OD) of 0.1. The culture was again diluted tenfold to obtain the working stock. Each ligand dissolved in DMSO was diluted in the inoculated culture medium to obtain a final concentration of 25 µM (DMSO 0.5% final). These solutions were then used to inoculate the BCG cultures in the presence of ethionamide solutions of increasing concentrations ranging from 0.04 µg/ml to 5 µg/mL. The tubes were then incubated with agitation at 37° C. The OD of the tubes was taken each day for 10 days by reading through the tube. The MIC corresponds to the minimum concentration of ethionamide that enables the bacterial growth to be inhibited and thus for which the OD remains unchanged.

d) Potentiating Effect of the Compounds of the Invention on *M. tuberculosis H*37Rv The ethionamide-potentiating effect of certain compounds of the invention was evaluated using:

- either the RIA detection method in liquid medium on a Bactec® 460 robot in 12 B medium,
- or the fluorimetric detection method in liquid medium on a Bactec® MG IT 960 robot.

i) RIA detection method on Bactec® 460.

The Bactec® system (Becton Dickinson) is based on a radiometric respirometry method. It consists in assessing the growth of the mycobacteria by measuring the amount of $^{14}CO_2$ released by the mycobacteria during their growth in a culture medium containing $^{14}C$-labeled palmitic acid as sole carbon source. The machine enables measurement of the amount of $^{14}CO_2$ in the gaseous atmosphere of the flask and to express it according to a graduation known as the GI (Growth Index) ranging from 0 (absence of $^{14}CO_2$) to 999, corresponding to the maximum amount of growth that can be detected by the robot.

The reference strain *M. tuberculosis* H37Rv was maintained in Jensen medium. A suspension in sterile distilled water served to inject 12B medium, and incubated in the Bactec® 460 system until a GI=500 was obtained. A hundred-fold dilution was performed and 100 µl were injected into the Bactec® 12B flasks. When the flask reached a growth index of greater than 300, the compounds of the invention were added at a final concentration of 25 or 100 mM against a concentration range of ethionamide extending from 6 to 0.06 mM. A control series containing ethionamide alone, or the compounds of the invention alone, was prepared. The flasks were incubated at 37° C. and a respirometric reading was taken once a day from D+1 up to D+9.

The GI value measurements were used to determine the potentiating effect of the compounds according to the invention. Only the maximum concentration value of the compounds of the invention (25 or 100 µM) not affecting the value of GI in the absence of ETH was considered to determine the potentiating effect. Potentiation is acknowledged if the minimum inhibitory concentration of ETH is reduced at least twofold by the presence of a compound of the invention, and if said compound has no effect alone on the growth at that same concentration.

ii) Fluorimetric detection method in liquid medium on the Bactec° MG IT 960 robot.

This method uses a ruthenium salt, this substance emitting fluorescence that is proportionately stronger the lower the partial pressure of oxygen. The metabolism of the mycobacteria causes a depletion of oxygen and results in the appearance of fluorescence whose intensity is proportional to the level of reduction of the medium.

The *M. tuberculosis* H37RV mycobacterial strain was prepared as described previously and inoculated in MGIT tubes. An ethionamide concentration range extending from 6 to 0.6 mM was added to a series of tubes containing the test compounds of the invention (either 25 or 100 µM) and to a series containing no compound. The positive control comprised only the mycobacteria inoculated in the medium. The fluorescence readings were taken daily up to a maximum of nine days.

The fluorescence value measurements were used to determine the potentiating effect of the compounds according to the invention. Only the maximum concentration value of the compounds of the invention (25 or 100 µM) not affecting the fluorescence value in the absence of ETH was considered to determine the potentiating effect. Potentiation is acknowledged if the minimum inhibitory concentration of ETH is reduced at least twofold by the presence of a compound of the invention, and if said compound has no effect alone on the growth at that same concentration.

e) Measurement of the Solubility of the Compounds of the Invention

40 µl of a solution containing a compound of the invention at a concentration of 10 mM in DMSO were diluted in 1.960 ml of methanol, and another 40 µl were diluted in 1.960 ml of a PBS solution containing 675 mM of NaCl, 13.5 mM of KCl, 50 mM of $Na_2HPO_4.2H_2O$ and 10 mM of $KH_2PO_4$ at a pH of 7.4. The two solutions were stirred for 24 hours at room temperature, and then centrifuged for 5 minutes and filtered through 0.45 µm filters. 20 µl of each solution were then diluted in 118 µl of methanol and analyzed by liquid chromatography coupled to mass spectrometry (LC/MS). The solubility was determined by the ratio of the areas under the curve of the mass signal for the compound of the invention, according to the following equation:

$$\text{solubility} = \frac{Area_{PBS}}{Area_{methanol}}$$

2) Results

The results obtained as regards the inhibition of interaction of EthR with its target DNA sequence, the $IC_{50}$, the $MIC_{ETH}$ and the potentiating effect of the compounds of the invention on ethionamide activity are collated in Table I below:

TABLE I

| Compound No. | Inhibition % | $IC_{50}$ (µM) | $MIC_{ETH}$ (µM) | Potentiation % |
|---|---|---|---|---|
| I-1 | 33 | 1.54 | 0.24 | 2500 |
| 3 | 14 | ND | 1.20 | 500 |
| 4 | 15 | ND | 1.20 | 500 |
| 5 | 15 | ND | ND | ND |
| 12 | 19 | ND | 1.20 | ND |
| 15 | 94 | 1.56 | ND | ND |
| 16 | 15[a] | 38.0[b] | 1.20 | 500 |
| 19 | 15 | ND | ND | ND |
| 20 | 53 | 1 | 0.24 | 2500 |
| 21 | 20 | ND | 1.2 | 500 |
| 22 | 28 | 3.33 | 0.24 | 2500 |
| 25 | 70 | 0.91 | 1.2 | 500 |
| 27 | 96 | 1.57 | 1.2 | 500 |
| 33 | 71 | 1.12 | 0.24 | 2500 |
| 34 | 48 | ND | ND | ND |
| 35 | 52 | 1.49 | 0.24 | 2500 |
| 36 | 78 | 1 | 1.2 | 500 |
| 37 | 76 | 3.49 | ND | ND |
| 40 | 59 | ND | ND | ND |
| 41 | 45 | ND | 0.24 | ND |
| 43 | 93 | 0.52 | 0.24 | 2500 |
| 44 | 96 | 0.95 | ND | ND |
| 45 | 75 | 1.5 | 0.24 | 2500 |
| 46 | 100[a], 52[c] | 1.79 | 1.20 | 500 |
| 47 | 100[a], 28[c] | 15.2 | ND | ND |
| 48 | 56 | 1.14 | ND | ND |
| 49 | 86 | 1.34 | ND | ND |
| 50 | 96 | 0.44 | ND | ND |
| 51 | 13 | ND | ND | ND |
| 52 | 61 | ND | ND | ND |
| 53 | 34 | ND | ND | ND |

TABLE I-continued

| Compound No. | Inhibition % | $IC_{50}$ (µM) | $MIC_{ETH}$ (µM) | Potentiation % |
|---|---|---|---|---|
| 54 | 5 | ND | ND | ND |
| 55 | 100 | 0.908 | 1.20 | 500 |
| 56 | 100 | 0.944 | 0.24 | 2500 |
| 57 | 46 | ND | ND | ND |
| 58 | 34 | ND | ND | ND |
| 59 | 77 | 0.39 | ND | ND |

[a]DNA test conditions: 20 RU, EthR: 200 nM, compound: 25 µM.

[b]DNA test conditions: 20 RU, EthR: 350 nM

[c]DNA test conditions: 20 RU, EthR: 200 nM, compound: 1 µM. under these conditions, the reference compound (I-1) had a percentage of inhibition equal to 45%.

Figure 2:
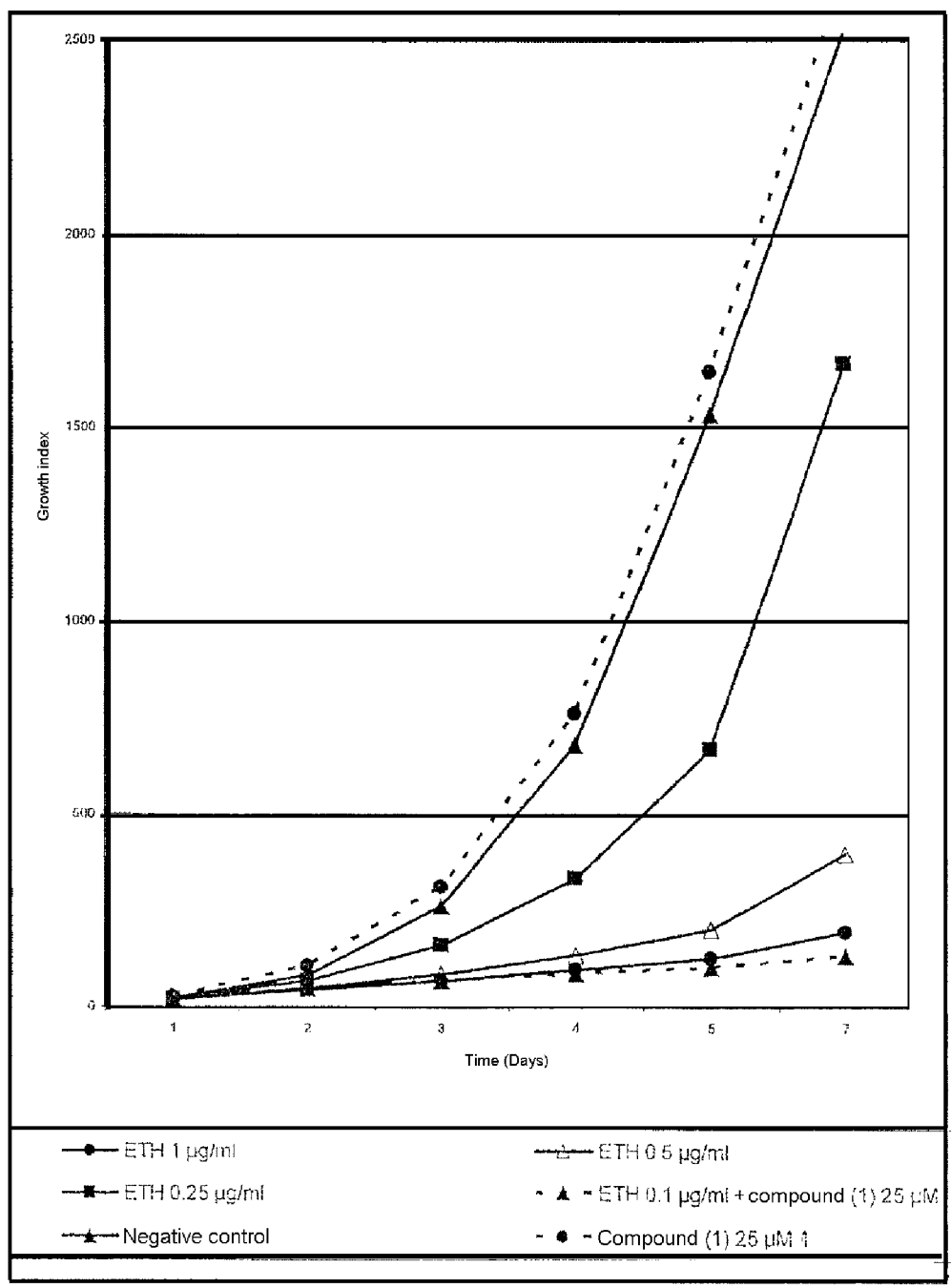

The ethionamide-potentiating effect of compound (I-1) evaluated according to the RIA detection method in liquid medium on the Bactec® 460 robot in 12 B medium is shown in the attached FIG. 2, in which the growth index (arbitrary units) is presented as a function of the time in days. The key to this figure is as follows:

broken line, filled circles: compound (I-1) alone 25 µM;

continuous line, empty triangles: ETH 0.5 µg/ml;

broken line, filled triangles: ETH 0.1 µg/ml+compound (I-1) 25 µM;

continuous line, filled circles: ETH 1 µg/ml;

continuous line, filled squares: ETH 0.25 µg/ml;

continuous line, filled triangles: negative control without any chemical compound.

The results presented in this figure indicate that the MIC for ETH under these experimental conditions is 1 µg/ml (6 µM) (curve with the filled squares). The same growth-inhibiting effect is obtained by placing in contact 0.1 µg/ml (0.6 µM) of ETH and 25 µM of compound (I-1). The potentiating effect of compound (I-1) of the invention is thus at least equal to a factor of 10.

The activity of compounds 33 and 43 of the invention was also evaluated in vitro at 25 µM on the Bactec® 960 machine

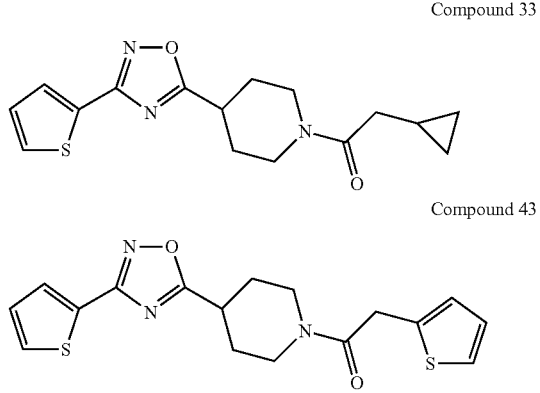

Compound 33

Compound 43

Compounds 33 and 43 were tested as regards their capacity to potentiate ethionamide (ETH) with the Bactec® MGIT 960 machine, according to the procedure described above.

The results obtained are presented in Table II below:

TABLE II

| Tube | Strain | [ETH] (μg/mL) | Ligand 25 μM | D + 0 | D + 1 | D + 5 | D + 5 | D + 6 | D + 7 | D + 7 | J + 8 | State |
|---|---|---|---|---|---|---|---|---|---|---|---|---|
| A1 | 1% | 0 | 0 | 0 | 0 | 0 | 0 | 0 | 78 | 151 | 400 | C |
| A2 | 1% | solvent | 0 | 0 | 0 | 0 | 0 | 0 | 110 | 199 | 400 | R |
| A3 | 1% | 0 | Compound 33 | 0 | 0 | 0 | 0 | 1 | 180 | 319 | 400 | R |
| A4 | 100% | solvent | 0 | 0 | 0 | 400 | 400 | 400 | 400 | 400 | 400 | R |
| A5 | 100% | 0 | Compound 33 | 0 | 0 | 400 | 400 | 400 | 400 | 400 | 400 | R |
| B1 | 1% | 0 | 0 | 0 | 0 | 0 | 0 | 0 | 149 | 262 | 400 | C |
| B2 | 100% | 2 | 0 | 0 | 0 | 0 | 0 | 0 | 0 | 0 | 0 | S |
| B3 | 100% | 1 | 0 | 0 | 0 | 0 | 0 | 0 | 0 | 0 | 0 | S |
| B4 | 100% | 0.5 | 0 | 0 | 0 | 0 | 0 | 0 | 6 | 16 | 23 | S |
| B5 | 100% | 0.25 | 0 | 0 | 0 | 14 | 36 | 125 | 400 | 400 | 400 | R |
| C1 | 1% | 0 | 0 | 0 | 0 | 0 | 0 | 0 | 194 | 329 | 400 | C |
| C2 | 100% | 0.25 | Compound 33 | 0 | 0 | 0 | 0 | 0 | 0 | 0 | 0 | S |
| C3 | 100% | 0.1 | Compound 33 | 0 | 0 | 0 | 0 | 0 | 0 | 0 | 0 | S |
| C4 | 100% | 0.05 | Compound 33 | 0 | 0 | 0 | 0 | 0 | 0 | 0 | 0 | S |
| C5 | 100% | 0.025 | Compound 33 | 0 | 0 | 200 | 353 | 400 | 400 | 400 | 400 | R |
| D1 | 1% | 0 | 0 | 0 | 0 | 0 | 0 | 0 | 42 | 96 | 400 | C |
| D2 | 1% | 0 | Compound 43 | 0 | 0 | 0 | 0 | 0 | 168 | 292 | 400 | R |
| D3 | 100% | 0 | Compound 43 | 0 | 0 | 400 | 400 | 400 | 400 | 400 | 400 | R |
| E1 | 1% | 0 | 0 | 0 | 0 | 0 | 0 | 0 | 80 | 150 | 400 | C |
| E2 | 100% | 0.25 | Compound 43 | 0 | 0 | 0 | 0 | 0 | 0 | 0 | 0 | S |
| E3 | 100% | 0.1 | Compound 43 | 0 | 0 | 0 | 0 | 0 | 0 | 0 | 0 | S |
| E4 | 100% | 0.05 | Compound 43 | 0 | 0 | 0 | 0 | 0 | 0 | 0 | 0 | S |
| E5 | 100% | 0.025 | Compound 43 | 0 | 0 | 0 | 0 | 0 | 0 | 0 | 0 | S |

Key: C = control; S = sensitive (total inhibition of bacterial growth); R = resistant (appearance of bacterial growth)

It may be observed that the measurements performed in the presence of compounds 33 and 43 reveal the absence of bacterial growth-inhibiting properties of these compounds at 25 μM (Table II: lines A5 and D3).

This table also gives information regarding the MIC of ethionamide used as sole growth inhibitor (lines B1 to B5). This is equal to 1 μg/ml (6 μM) under the experimental conditions. The ETH-potentiating effect of compound 33 is illustrated by the measurements taken at C1 to C5, which indicate that, in the presence of compound 33 of the invention, the MIC for ETH falls to 0.05 μg/ml (0.3 μM), i.e. a factor of 20. As regards compound 43 of the invention, lines E1 to E5 reveal that the MIC for ETH in the presence of this compound is less than 0.025 μg/mL (0.15 μM). Compound 43 of the invention allows potentiation of the ethionamide activity by a factor at least equal to 40.

Compounds 20 and 22 showed ETH-activity potentiation of a factor of about 20 and 10, respectively, in this same test.

Solubility Results for Certain Compounds of the Invention:

The solubility of certain compounds of the invention tested under the conditions detailed above is given in Table III below:

TABLE III

| Compound No. | Solubility (μg/mL) |
|---|---|
| 1 | 9.5 |
| 5 | 9 |
| 12 | 71 |
| 17 | 55.5 |
| 20 | 63.5 |
| 22 | 60.4 |
| 28 | 61.5 |
| 31 | 67.1 |
| 33 | 63.5 |
| 43 | 26.9 |
| 44 | 16.3 |
| 46 | 53.7 |
| 48 | 0.86 |
| 50 | 2.9 |
| 51 | 271.73 |
| 54 | 38.7 |

The inventon claimed is:

1. A pharmaceutical composition comprising as active principle at least one compound of formula (I-e), at least one pharmaceutically acceptable excipient and at least one antibiotic that is activatable via the EthA enzymatic pathway, wherein the compounds corresponding to formula (I-e) are as follows:

(I-e)

in which $X_2$ is chosen from the groups ($X_2$-1) to ($X_2$-23) below:

($X_2$-1)

($X_2$-2)

($X_2$-3)

($X_2$-4)

($X_2$-5)

($X_2$-6)

($X_2$-7)

($X_2$-8)

($X_2$-9)

($X_2$-10)

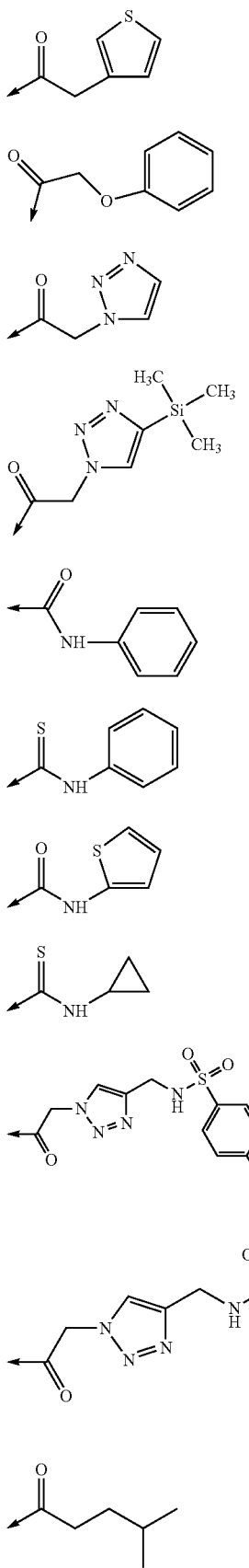

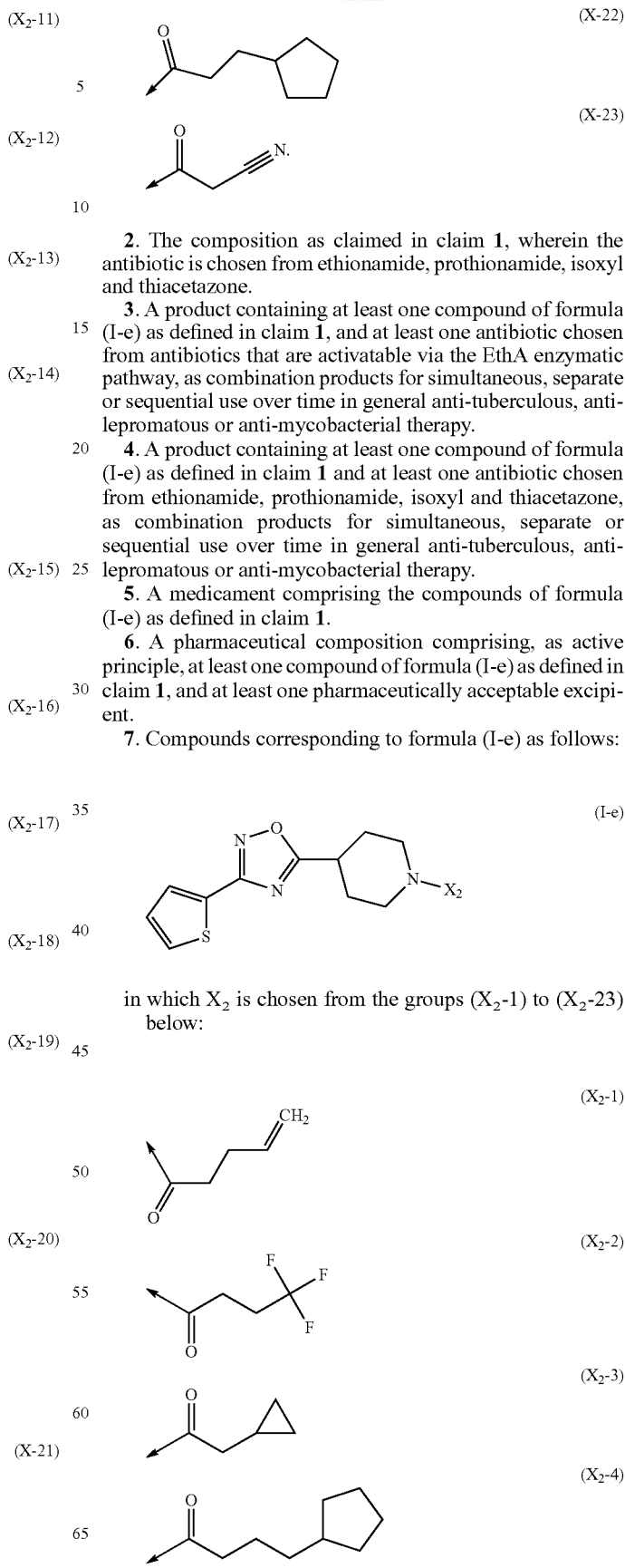

2. The composition as claimed in claim 1, wherein the antibiotic is chosen from ethionamide, prothionamide, isoxyl and thiacetazone.

3. A product containing at least one compound of formula (I-e) as defined in claim 1, and at least one antibiotic chosen from antibiotics that are activatable via the EthA enzymatic pathway, as combination products for simultaneous, separate or sequential use over time in general anti-tuberculous, anti-lepromatous or anti-mycobacterial therapy.

4. A product containing at least one compound of formula (I-e) as defined in claim 1 and at least one antibiotic chosen from ethionamide, prothionamide, isoxyl and thiacetazone, as combination products for simultaneous, separate or sequential use over time in general anti-tuberculous, anti-lepromatous or anti-mycobacterial therapy.

5. A medicament comprising the compounds of formula (I-e) as defined in claim 1.

6. A pharmaceutical composition comprising, as active principle, at least one compound of formula (I-e) as defined in claim 1, and at least one pharmaceutically acceptable excipient.

7. Compounds corresponding to formula (I-e) as follows:

in which $X_2$ is chosen from the groups ($X_2$-1) to ($X_2$-23) below:

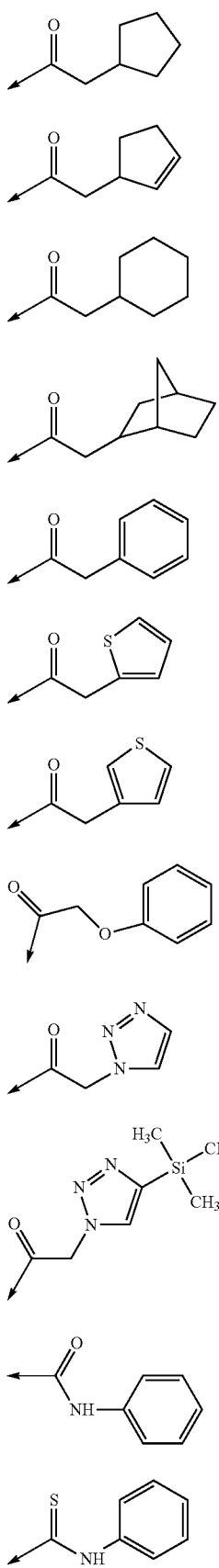
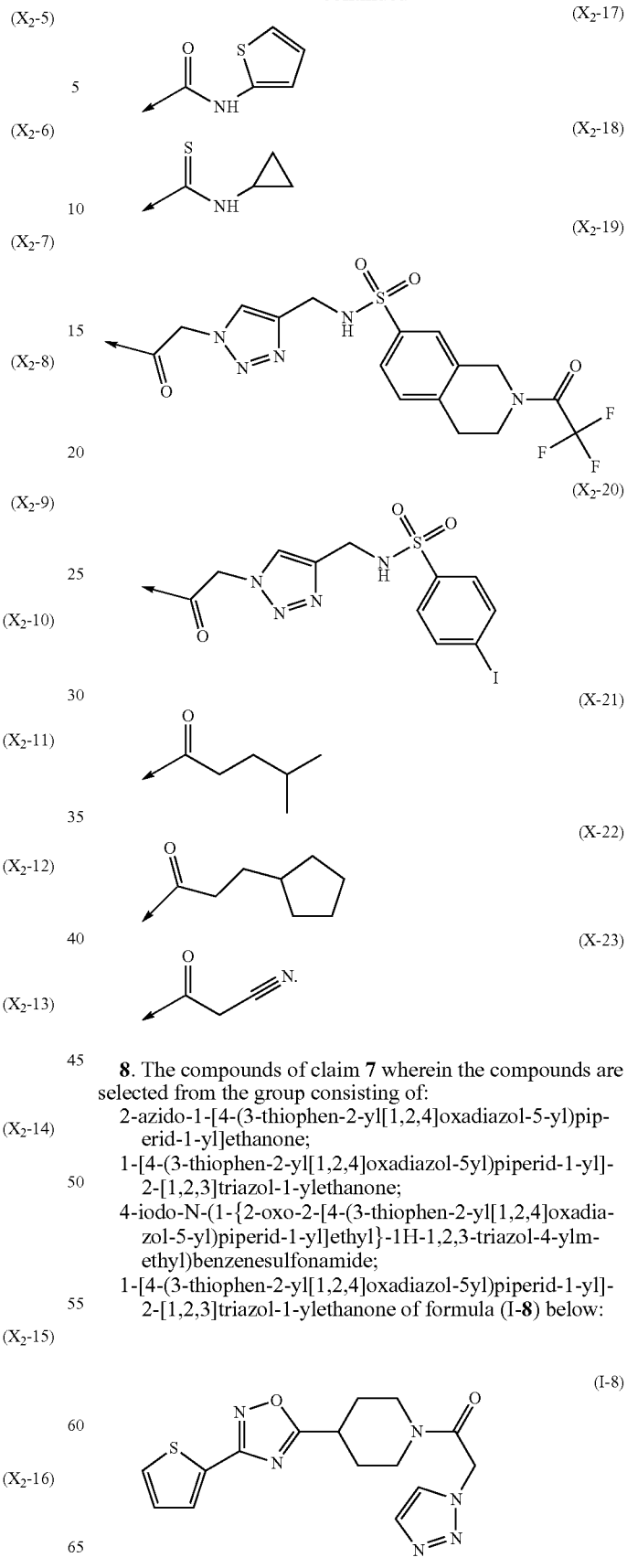

8. The compounds of claim 7 wherein the compounds are selected from the group consisting of:
2-azido-1-[4-(3-thiophen-2-yl[1,2,4]oxadiazol-5-yl)piperid-1-yl]ethanone;
1-[4-(3-thiophen-2-yl[1,2,4]oxadiazol-5yl)piperid-1-yl]-2-[1,2,3]triazol-1-ylethanone;
4-iodo-N-(1-{2-oxo-2-[4-(3-thiophen-2-yl[1,2,4]oxadiazol-5-yl)piperid-1-yl]ethyl}-1H-1,2,3-triazol-4-ylmethyl)benzenesulfonamide;
1-[4-(3-thiophen-2-yl[1,2,4]oxadiazol-5yl)piperid-1-yl]-2-[1,2,3]triazol-1-ylethanone of formula (I-8) below:

2-(2,2,2-trifluoroacetyl)-1,2,3,4-tetrahydroisoquinoline-7-sulfonic acid (1-{2-oxo-2-[4-(3-thiophen-2-yl[1,2,4]oxadiazol-5-yl)piperid-1-yl]ethyl}-1H-[1,2,3]triazol-4-ylmethyl)amide of formula (I-9) below:

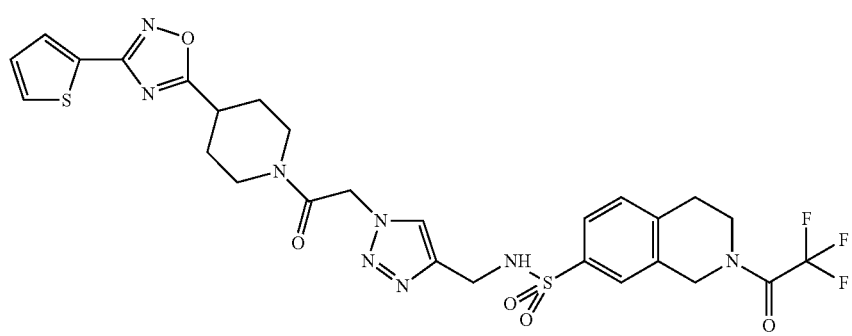

(I-9)

2-phenoxy-1-[4-(3-thiophen-2-yl[1,2,4]oxadiazol-5-yl)piperid-1-yl]ethanone;
3-cyclopentyl-1-[4-(3-thiophen-2-yl[1,2,4]oxadiazol-5-yl)piperid-1-yl]propan-1-one;
2-thiophen-2-yl-1-[4-(3-thiophen-2-yl[1,2,4]oxadiazol-5-yl)piperid-1-yl]ethanone;
4-methyl-1-[4-(3-thiophen-2-yl[1,2,4]oxadiazol-5-yl)piperid-1-yl]pentan-1-one;
2-bicyclo[2.2.1]hept-2-yl-1-[4-(3-thiophen-2-yl[1,2,4]oxadiazol-5-yl)piperid-1-yl]ethanone;
-2-cyclopropyl-1-[4-(3-thiophen-2-yl[1,2,4]oxadiazol-5-yl)piperid-1-yl]ethanone; and
2-phenyl-1-[4-(3-thiophen-2-yl[1,2,4]oxadiazol-5-yl)piperid-1-yl]ethanone.

9. The compounds of claim 7 wherein the compounds are selected from the group consisting of:
2-cyclohexyl-1-[4-(3-thiophen-2-yl[1,2,4]oxadiazol-5-yl)piperid-1-yl]ethanone;
2-cyclopent-2-enyl-1-[4-(3-thiophen-2-yl[1,2,4]oxadiazol-5-yl)piperid-1-yl]ethanone;
2-cyclopentyl-1-[4-(3-thiophen-2-yl[1,2,4]oxadiazol-5-yl)piperid-1-yl]ethanone;
4,4,4-trifluoro-1-[4-(3-thiophen-2-yl[1,2,4]oxadiazol-5-yl)piperid-1-yl]butan-1-one;
1-[4-(3-thiophen-2-yl[1,2,4]oxadiazol-5-yl)piperid-1-yl]pent-4-yn-1-one;
3-oxo-3-[4-(3-thiophen-2-yl[1,2,4]oxadiazol-5-yl)piperid-1-yl]propionitrile;
2-thiophen-3-yl-1-[4-(3-thiophen-2-yl[1,2,4]oxadiozal-5-yl)piperid-1-yl]ethanone;
2-(2-aminothiazol-4-yl)-1-[4-(3-thiophen-2-yl[1,2,4]oxadiazol-5-yl)piperid-1-yl]ethanone; and
2-(1H-tetrazol-5-yl)-1-[4-(3-thiophen-2-yl[1,2,4]oxadiazol-5-yl)piperid-1-yl]ethanone.

* * * * *